United States Patent
Tanabe et al.

(10) Patent No.: US 11,124,492 B2
(45) Date of Patent: *Sep. 21, 2021

(54) HETEROCYCLIC COMPOUND

(71) Applicant: Sumitomo Chemical Company, Limited, Tokyo (JP)

(72) Inventors: Takamasa Tanabe, Takarazuka (JP); Yoshihiko Nokura, Takarazuka (JP); Kohei Orimoto, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/079,348

(22) PCT Filed: Feb. 17, 2017

(86) PCT No.: PCT/JP2017/005837
§ 371 (c)(1),
(2) Date: Aug. 23, 2018

(87) PCT Pub. No.: WO2017/150209
PCT Pub. Date: Sep. 8, 2017

(65) Prior Publication Data
US 2019/0040038 A1   Feb. 7, 2019

(30) Foreign Application Priority Data
Feb. 29, 2016   (JP) ............... JP2016-036956

(51) Int. Cl.
*C07D 401/04* (2006.01)
*A01N 43/40* (2006.01)
(Continued)

(52) U.S. Cl.
CPC ........... *C07D 401/04* (2013.01); *A01N 43/40* (2013.01); *A01N 43/54* (2013.01); *A01N 43/58* (2013.01);
(Continued)

(58) Field of Classification Search
None
See application file for complete search history.

(56) References Cited

U.S. PATENT DOCUMENTS

| 6,271,179 B1 | 8/2001 | Rheinheimer et al. |
| 2017/0295787 A1 | 10/2017 | Tanabe et al. |
| 2018/0009778 A1 | 1/2018 | Tanabe et al. |

FOREIGN PATENT DOCUMENTS

| CN | 104621100 A | 5/2015 |
| JP | 200026421 A | 1/2000 |

(Continued)

OTHER PUBLICATIONS

Xu, et al., "Palladium-Catalyzed Trifluoromethylthiolation of Aryl C—H Bonds", Organic Letters, vol. 16, No. 7, pp. 2046-2049, (Mar. 2014).

(Continued)

*Primary Examiner* — John Pak
*Assistant Examiner* — Daniel L Branson
(74) *Attorney, Agent, or Firm* — Panitch Schwarze Belisario & Nadel LLP

(57) ABSTRACT

A compound represented by formula (I)

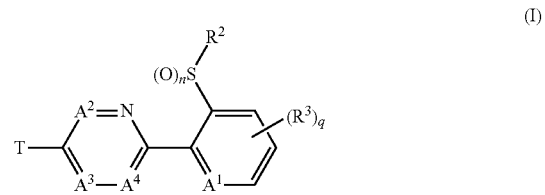

or an N-oxide compound thereof is provided with excellent control efficacies against harmful arthropods, wherein
$A^1$ represents a nitrogen atom or a $CR^4$;
$R^4$ represents a hydrogen atom, a $OR^{27}$, a $NR^{27}R^{28}$, a cyano group, a nitro group, or a halogen atom;

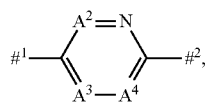

hereinafter referred to as "Het", represents Het-1, Het-2, Het-3, or Het-4:

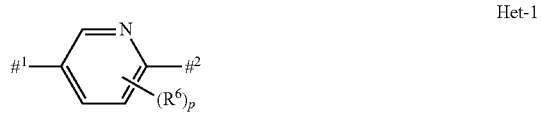

Het-1

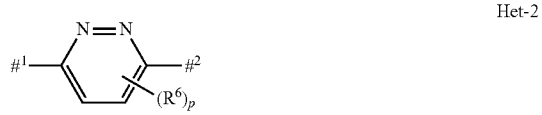

Het-2

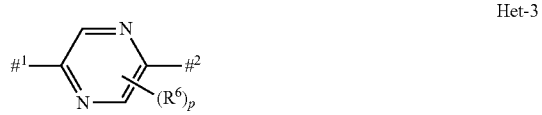

Het-3

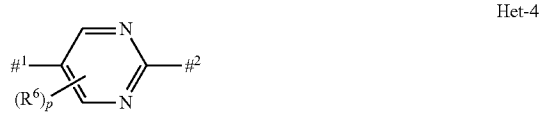

Het-4

(Continued)

wherein #¹ represents the binding position of Het and T, and #² represents the binding position of Het and

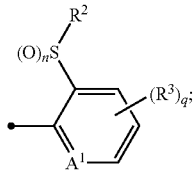

T represents T-1, T-2, T-3, T-4, T-5, T-6, or T-7:

T-1

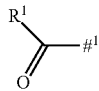

T-2

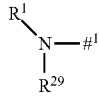

T-3

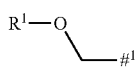

T-4

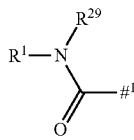

T-5

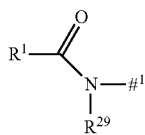

T-6

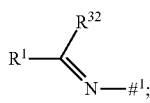

T-7

$R^1$ represents a C1-C10 chain hydrocarbon group having one or more halogen atoms or the like; and $R^2$ represents a C1-C6 alkyl group optionally having one or more halogen atoms or the like.

10 Claims, No Drawings

(51) Int. Cl.
    *A01N 43/58* (2006.01)
    *A01N 43/60* (2006.01)
    *C07D 213/34* (2006.01)
    *C07D 213/70* (2006.01)
    *C07D 213/32* (2006.01)
    *C07D 213/75* (2006.01)
    *C07D 213/82* (2006.01)
    *C07D 213/71* (2006.01)
    *C07D 213/74* (2006.01)
    *C07D 213/38* (2006.01)
    *A01N 43/54* (2006.01)
    *C07D 213/61* (2006.01)

(52) U.S. Cl.
    CPC ........... *A01N 43/60* (2013.01); *C07D 213/32* (2013.01); *C07D 213/34* (2013.01); *C07D 213/38* (2013.01); *C07D 213/61* (2013.01); *C07D 213/70* (2013.01); *C07D 213/71* (2013.01); *C07D 213/74* (2013.01); *C07D 213/75* (2013.01); *C07D 213/82* (2013.01)

(56) References Cited

FOREIGN PATENT DOCUMENTS

| | | | |
|---|---|---|---|
| JP | 2001524471 A | 12/2001 | |
| JP | WO2010064711 A1 | 5/2012 | |
| WO | 9746530 A1 | 12/1997 | |
| WO | 2010064711 A1 | 6/2010 | |
| WO | WO-2010064711 A1 * | 6/2010 | ............ A01N 43/40 |
| WO | 2016052455 A1 | 4/2016 | |
| WO | 2016121969 A1 | 8/2016 | |
| WO | 2016121970 A1 | 8/2016 | |

OTHER PUBLICATIONS

Niu, et al., "Functionalizations of Aryl C—H Bonds in 2-Arylphyridines via Sequential Borylation and Copper Catalysis", Advanced Synthesis and Catalysis, vol. 354, No. 11-12, pp. 2211-2217, (Aug. 2012).
XP_002791801, Database Registry, Chemical Abstracts Service, Database accession No. 1609850-26-1, (Jun. 2014).
XP-002791802, Database Registry, Chemical Abstracts Service, Database accession No. 1609760-92-0, (Jun. 2014).
Extended European Search Report issued in European Patent App. No. 17759679.8 dated Jul. 12, 2019.
International Search Report dated Apr. 17, 2017 in International Application No. PCT/JP2017/005837 (English Translation).
International Preliminary Report on Patentability dated Sep. 4, 2018 in International Application No. PCT/JP2017/005837 (English Translation).
Office Action and Search Report dated Nov. 30, 2020 in CN Application No. 201780013711.4.
Office Action dated Sep. 30, 2020 in IN Application No. 201847035081.
Office Action dated Sep. 29, 2020 in JP Application No. 2018503026.

* cited by examiner

HETEROCYCLIC COMPOUND

CROSS-REFERENCE TO RELATED APPLICATION

This application is a Section 371 of International Application No. PCT/JP2017/005837, filed Feb. 17, 2017, which was published in the Japanese language on Sep. 8, 2017, under International Publication No. WO 2017/150209 A1, which claims priority under 35 U.S.C. § 119(b) to Japanese Application No. 2016-036956, filed Feb. 29, 2016, the disclosures of which are incorporated herein by reference in their entirety.

TECHNICAL FIELD

The present invention relates to a heterocyclic compound and an agent for controlling harmful arthropods comprising the same.

BACKGROUND ART

To date, various compounds for controlling harmful arthropods have been studied and come into practical use (for example, see Patent Document 1).

CITATION LIST

Patent Document

Patent Document 1: JP 2000-26421 A

SUMMARY OF THE INVENTION

Problems to be Solved by Invention

An object of the present invention is to provide a compound having excellent control efficacies against harmful arthropods.

Means to Solve Problems

The present invention provides the followings.
[1] A compound represented by formula (I)

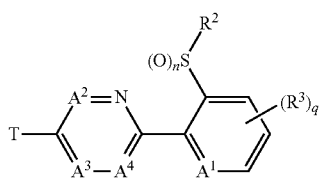

[wherein:
$A^1$ represents a nitrogen atom or a $CR^4$;
$R^4$ represents a hydrogen atom, a $OR^{27}$, a $NR^{27}R^{28}$, a cyano group, a nitro group, or a halogen atom;

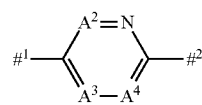

(hereinafter referred to as "Het") represents Het-1, Het-2, Het-3, or Het-4:

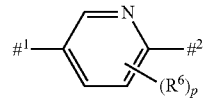

Het-1

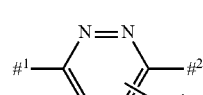

Het-2

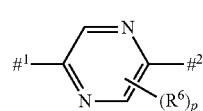

Het-3

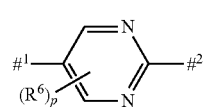

Het-4

(provided that $\#^1$ represents the binding position of Het and T, and $\#^2$ represents the binding position of Het and

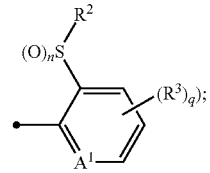

T represents T-1, T-2, T-3, T-4, T-5, T-6, or T-7:

T-1

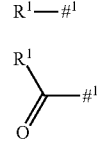

T-2

T-3

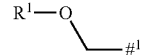

T-4

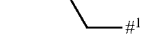

T-5

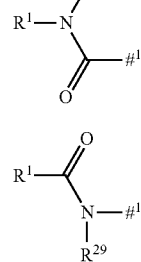

T-6

-continued

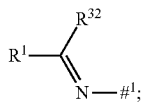
T-7

R¹ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

R² represents a C1-C6 alkyl group optionally having one or more halogen atoms, a cyclopropylmethyl group, or a cyclopropyl group;

q represents 0, 1, 2, or 3;

R³ represents a C1-C6 chain hydrocarbon group optionally having one or more substituents selected from Group B, a phenyl group optionally having one or more substituents selected from Group D, a 5 or 6 membered aromatic heterocyclic group optionally having one or more substituents selected from Group D, a $OR^{12}$, a $NR^{11}R^{12}$, a $NR^{11a}R^{12a}$, a $NR^{24}NR^{11}R^{12}$, a $NR^{24}OR^{11}$, a $NR^{11}C(O)R^{13}$, a $NR^{24}NR^{11}C(O)R^{13}$, a $NR^{11}C(O)$ $OR^{14}$, a $NR^{24}NR^{11}C(O)$ $OR^{14}$, a $NR^{11}C(O)NR^{15}R^{16}$, a $NR^{24}NR^{11}C(O)$ $NR^{15}R^{16}$, a $N=CHNR^{15}R^{16}$, a $N=S(O)_xR^{15}R^{16}$, a $S(O)_yR^{15}$, a $C(O)$ $OR^{17}$, a $C(O)NR^{11}R^{12}$, a cyano group, a nitro group, or a halogen atom, wherein when q represents 2 or 3, two or three R³ may be identical to or different from each other;

p represents 0, 1, or 2;

R⁶ represents a C1-C6 alkyl group optionally having one or more halogen atoms, a $OR^8$, a $NR^{18}R^{19}$, a cyano group, a nitro group, or a halogen atom, wherein when p represents 2, two R⁶ may be identical to or different from each other;

$R^{11}$, $R^{17}$, $R^8$, $R^9$, $R^{24}$, and $R^{29}$ represent each independently a hydrogen atom or a C1-C6 chain hydrocarbon group optionally having one or more halogen atoms;

$R^{32}$ represents a hydrogen atom, a halogen atom, a $OR^{33}$, a $NR^{34}R^{35}$, or a C1-C6 chain hydrocarbon group optionally having one or more halogen atoms;

$R^{33}$ represents a C1-C6 chain hydrocarbon group optionally having one or more halogen atoms;

$R^{34}$ and $R^{35}$ represent each independently a hydrogen atom or a C1-C6 chain hydrocarbon group optionally having one or more halogen atoms;

$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;

$R^{23}$ represents a C1-C6 chain hydrocarbon group optionally having one or more halogen atoms or a phenyl group optionally having one or more substituents selected from Group D;

$R^{11a}$ and $R^{12a}$ are combined with the nitrogen atom to which they are attached to represent a 3-7 membered nonaromatic heterocyclic group optionally having one or more substituents selected from Group E {wherein said 3-7 membered nonaromatic heterocyclic group represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring};

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {wherein the phenyl moiety in the phenyl C1-C3 alkyl group may optionally have one or more substituents selected from Group D};

$R^{15}$ and $R^{16}$ represent each independently a C1-C6 alkyl group optionally having one or more halogen atoms;

$R^{27}$ and $R^{28}$ represent each independently a hydrogen atom or a C1-C6 alkyl group optionally having one or more halogen atoms;

n and y represent each independently 0, 1, or 2; and x represents 0 or 1;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$ group, a $OC(O)R^{21}$ group, a $C(O)OR^{21}$ group, a cyano group, a nitro group, and a halogen atom {wherein $R^{21}$ and $R^{22}$ represent each independently a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3-7 membered nonaromatic heterocyclic group optionally having one or more substituents selected from Group C;

Group G: a group consisting of a halogen atom and a C1-C6 haloalkyl group]

or an N-oxide compound thereof (hereinafter a compound represented by formula (I) or an N-oxide compound thereof is referred to as "compound of the present invention" or "Present compound").

[2] The compound according to [1], wherein

T represents T-1, T-3, or T-4; and $R^1$ represents a C1-C10 chain hydrocarbon group having one or more halogen atoms or a (C1-C5 alkoxy)C2-C5 alkyl group having one or more halogen atoms.

[3] The compound according to [1] or [2], wherein $R^2$ represents an ethyl group.

[4] The compound according to any one of [1] to [3], wherein Het represents Het-1, Het-2, or Het-3.

[5] The compound according to any one of [1] to [3], wherein Het represents Het-1.

[6] The compound according to any one of [1] to [3], wherein Het represents Het-2.

[7] The compound according to any one of [1] to [3], wherein Het represents Het-3.

[8] The compound according to any one of [1] to [3], wherein Het represents Het-4.

[9] The compound according to any one of [1] to [8], wherein $R^3$ represents a C1-C6 chain hydrocarbon group optionally having one or more halogen atoms, or a halogen atom.

[10] The compound according to any one of [4] to [8], wherein

T represents T-1, T-3, or T-4;

$R^2$ represents an ethyl group;

$R^3$ represents a C1-C6 chain hydrocarbon group optionally having one or more substituents selected from Group B, a phenyl group optionally having one or more substituents selected from Group G, a 5 membered aromatic heterocyclic group having 1 to 4 nitrogen atoms (wherein said 5 membered aromatic heterocyclic group may optionally have one or more substituents selected from the group consisting of a C1-C6 alkyl group having one or more halogen atoms, and a halogen atom), a 6 membered aromatic heterocyclic group having 1 to 2 nitrogen atoms (wherein said 6 membered aromatic heterocyclic group may optionally have one or more substituents selected from the group consisting of a C1-C6 alkyl group having one or more halogen atoms, and a halogen atom), a $NR^{11}R^{12}$, a $NR^{11a}R^{12a}$, a $NR^{24}NR^{11}R^{12}$, or a halogen atom;

q represents 0, 1, or 2, wherein when q represents 2, two $R^3$ may be identical to or different from each other;

$R^6$ represents a C1-C6 alkyl group optionally having one or more halogen atoms, or a halogen atom; and p represents 0 or 1.

[11] The compound according to any one of [4] to [8], wherein

T represents T-1;

$A^1$ represents a nitrogen atom or a CH;

$R^2$ represents an ethyl group;

$R^3$ represents a C1-C6 chain hydrocarbon group optionally having one or more halogen atoms, or a halogen atom;

q represents 0 or 1;

$R^6$ represents a C1-C6 alkyl group optionally having one or more halogen atoms, or a halogen atom; and p represents 0 or 1.

[12] The compound according to any one of [4] to [8], wherein

T represents T-3;

$A^1$ represents a nitrogen atom or a CH;

$R^2$ represents an ethyl group;

$R^3$ represents a C1-C6 chain hydrocarbon group optionally having one or more halogen atoms, or a halogen atom;

q represents 0 or 1;

$R^6$ represents a C1-C6 alkyl group optionally having one or more halogen atoms, or a halogen atom; and p represents 0 or 1.

[13] The compound according to any one of [4] to [8], wherein

T represents T-4;

$A^1$ represents a nitrogen atom or a CH;

$R^2$ represents an ethyl group;

$R^3$ represents a C1-C6 chain hydrocarbon group optionally having one or more halogen atoms, or a halogen atom;

q represents 0 or 1;

$R^6$ represents a C1-C6 alkyl group optionally having one or more halogen atoms, or a halogen atom; and p represents 0 or 1.

[14] A composition for controlling a harmful arthropod comprising the compound according to any one of [1] to [13] and an inert carrier.

[15] A method for controlling a harmful arthropod which comprises applying an effective amount of the compound according to any one of [1] to [13] to a harmful arthropod or a habitat where a harmful arthropod lives.

[16] A composition comprising one or more ingredients selected from the group consisting of Group (a), Group (b), Group (c), Group (d), and Group (e), and the compound according to any one of [1] to [13];

Group (a): a group consisting of an insecticidal active ingredient, an acaricidal active ingredient, and a nematicidal active ingredient;

Group (b): a fungicidal active ingredient;

Group (c): a plant growth regulatory ingredient;

Group (d): a phytotoxicity-reducing ingredient;

Group (e): a synergist

Effect of Invention

The Present compound has excellent control efficacies against harmful arthropods, and thus is useful as an active ingredient of an agent for controlling harmful arthropods.

MODE FOR CARRYING OUT THE INVENTION

The substituent(s) in the present invention is/are explained as follows.

When a substituent "optionally having one or more halogen atoms" has two or more halogen atoms, these halogen atom may be identical to or different from each other.

The expression of "CX-CY" as described herein means that the number of carbon atom is X to Y. For example, the expression of "C1-C6" means that the number of carbon atom is 1 to 6.

The term of "halogen atom" represents fluorine atom, chlorine atom, bromine atom, or iodine atom.

The term of "chain hydrocarbon group" represents an alkyl group, an alkenyl group, and an alkynyl group.

Examples of the term of "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, and hexyl group.

Examples of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group.

Examples of the term of "alkynyl group" include ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.

The term of "C1-C6 haloalkyl group" represents a C1-C6 alkyl group wherein one or more hydrogen atoms are substituted with one or more halogen atoms, and examples thereof include a C1-C6 fluoroalkyl group.

Examples of the term of "C1-C6 haloalkyl group" include chloroethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

The term of "C1-C6 fluoroalkyl group" represents a C1-C6 alkyl group wherein one or more hydrogen atoms are substituted with one or more fluorine atoms, and examples thereof include 2,2,2-trifluoroethyl group, 2,2,3,3-tetrafluoropropyl group, 1-methyl-2,2,3,3-tetrafluoropropyl group, and perfluorohexyl group.

The term of "(C1-C5 fluoroalkoxy)C2-C5 fluoroalkyl group" represents a group wherein a C1-C5 alkoxy group having one or more fluorine atoms is attached to a C2-C5 alkyl group having one or more fluorine atoms, and examples thereof include 1,1,2-trifluoro-2-(trifluoromethoxy)ethyl group and 2,2-difluoro-3-(2,2,2-trifluoroethoxy)propyl group.

Examples of the term of "cycloalkyl group" include cyclopropyl group, cyclobutyl group, cyclopentyl group, cyclohexyl group, and cycloheptyl group.

The term of "3-7 membered nonaromatic heterocyclic group" represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring, and examples of "3-7 membered nonaromatic heterocyclic group optionally having one or more substituents selected from Group E" include the following groups.

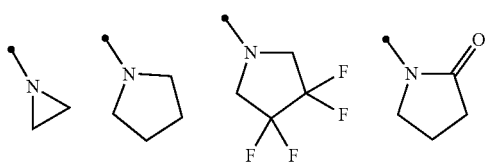

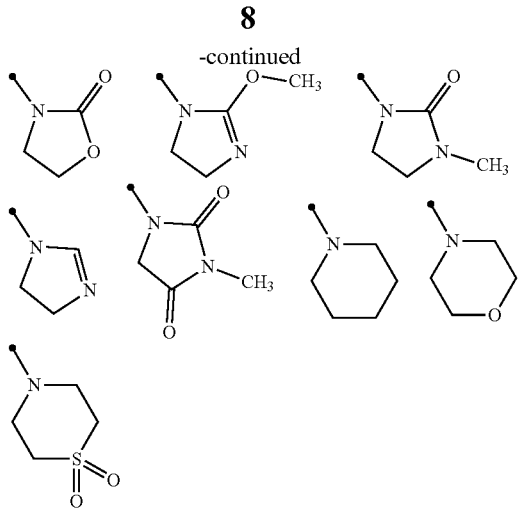

Examples of the term of "phenyl C1-C3 alkyl group {wherein the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "(C1-C5 alkoxy)C2-C5 alkyl group having one or more halogen atoms" represents a group wherein the (C1-C5 alkoxy) and/or the (C2-C5 alkyl) has one or more halogen atoms, and examples thereof include 2-(trifluoromethoxy)ethyl group, 2,2-difluoro-3-methoxypropyl, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) has one or more halogen atoms, and examples thereof include 2,2-difluoro-2-(trifluoromethylsulfanyl)ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl) has one or more halogen atoms, and examples thereof include 2,2-difluoro-2-(trifluoromethanesulfinyl)ethyl group.

The term of "(C1-C5 alkylsulfonyl)C2-C5 alkyl group having one or more halogen atoms" represents a group wherein the (C1-C5 alkylsulfonyl) and/or the (C2-C5 alkyl) has one or more halogen atoms, and examples thereof include 2,2-difluoro-2-(trifluoromethanesulfonyl)ethyl group.

The term of "(C3-C6 cycloalkyl)C1-C3 alkyl group optionally having one or more halogen atoms" represents a group wherein the (C3-C6 cycloalkyl) and/or the (C1-C3 alkyl) optionally has one or more halogen atoms, and examples thereof include (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "(C3-C7 cycloalkyl)C1-C3 alkyl group having one or more substituents selected from Group G" represents a group wherein the (C3-C7 cycloalkyl) and/or the (C1-C3 alkyl) has one or more substituents selected from Group G, and examples thereof include (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

The term of "5 or 6 membered aromatic heterocyclic group" represents a 5 membered aromatic heterocyclic group or a 6 membered aromatic heterocyclic group, and the term of "5 membered aromatic heterocyclic group" represents pyrrolyl group, furyl group, thienyl group, pyrazolyl group, imidazolyl group, triazolyl group, tetrazolyl group, oxazolyl group, isoxazolyl group, thiazolyl group, oxadiazolyl group, or thiadiazolyl group, and the term of "6 membered aromatic heterocyclic group" represents pyridyl group, pyridazinyl group, pyrimidinyl group, or pyrazinyl group.

The term of "6 membered aromatic heterocyclic group having 1 to 2 nitrogen atoms" represents pyridyl group, pyridazinyl group, pyrimidinyl group, or pyrazinyl group.

The term of "5 membered aromatic heterocyclic group having 1 to 4 nitrogen atoms" represents pyrrolyl group, pyrazolyl group, imidazolyl group, 1,2,4-triazolyl group, 1,2,3-triazolyl group, or tetrazolyl group.

The term of "N-oxide compound" represents a compound represented by formula (N-1), a compound represented by formula (N-2), a compound represented by formula (N-3), a compound represented by formula (N-4), a compound represented by formula (N-5), and a compound represented by formula (N-6).

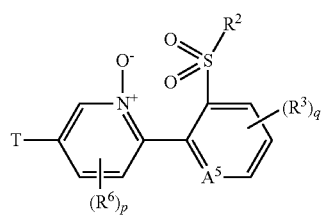
(N-1)

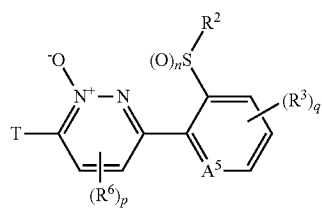
(N-2)

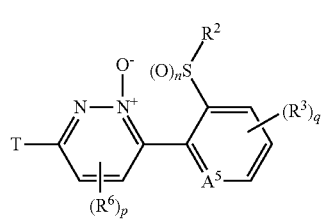
(N-3)

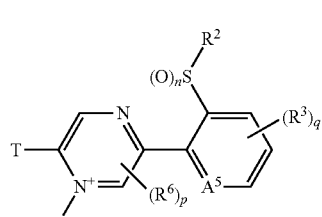
(N-4)

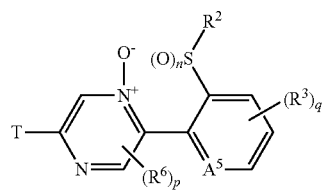
(N-5)

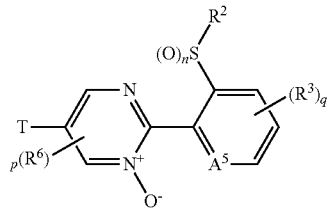
(N-6)

[wherein: $A^5$ represents a nitrogen atom, a $N^+O^-$, or a $CR^4$; and the other symbols are the same as defined above.]

Embodiments of the Present compound include the following compounds.

Embodiment 1

The Present compound, wherein $R^1$ represents a C1-C10 chain hydrocarbon group having two or more halogen atoms or a (C1-C5 fluoroalkoxy)C2-C5 fluoroalkyl group;

Embodiment 2

The Present compound, wherein $R^1$ represents a C1-C10 chain hydrocarbon group having two or more halogen atoms;

Embodiment 3

The Present compound, wherein $R^1$ represents a C1-C10 alkyl group having three or more fluorine atoms;

Embodiment 4

The Present compound, wherein $R^1$ represents a C1-C10 perfluoroalkyl group;

Embodiment 5

The Present compound, wherein $R^1$ represents a C2-C10 perfluoroalkyl group;

Embodiment 6

The Present compound, wherein $R^2$ represents a C1-C3 alkyl group optionally having one or more halogen atoms;

Embodiment 7

The Present compound, wherein $R^2$ represents a C1-C6 alkyl group;

Embodiment 8

The Present compound, wherein $R^2$ represents a C1-C3 alkyl group;

Embodiment 9

The Present compound, wherein R² represents a methyl group or an ethyl group;

Embodiment 10

The Present compound, wherein R² represents an ethyl group;

Embodiment 11

The Present compound, wherein R³ represents a C1-C6 chain hydrocarbon group optionally having one or more substituents selected from Group B, a phenyl group optionally having one or more substituents selected from Group D, a 6 membered aromatic heterocyclic group selected from Group L (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR¹², a NR¹¹R¹², a NR¹¹ᵃR¹²ᵃ, a NR²⁴NR¹¹R¹², or a halogen atom;

Group L:

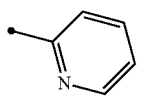
L-1

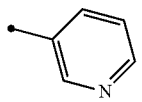
L-2

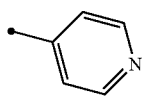
L-3

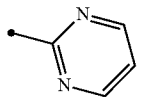
L-4

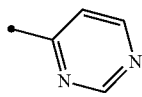
L-5

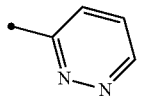
L-6

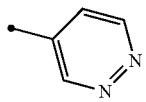
L-7

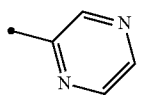
L-8

Group W:

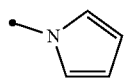
W-1

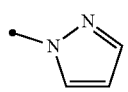
W-2

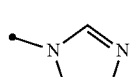
W-3

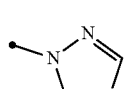
W-4

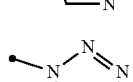
W-5

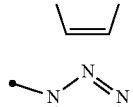
W-6

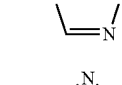
W-7

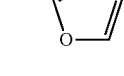
W-8

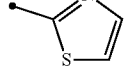
W-9

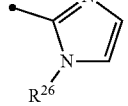
W-10

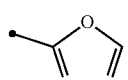
W-11

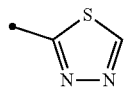
W-12

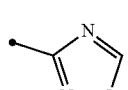
W-13

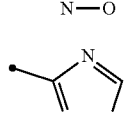
W-14

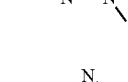
W-15

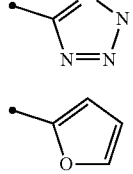

-continued

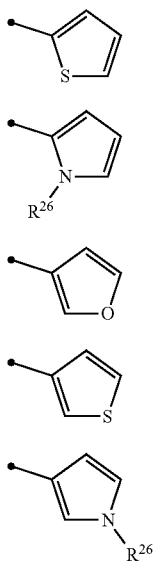

W-16

W-17

W-18

W-19

W-20

{wherein: $R^{26}$ represents a C1-C6 alkyl group optionally having one or more halogen atoms}

Embodiment 12

The Present compound, wherein
$R^3$ represents a C1-C6 alkyl group optionally having one or more halogen atoms, a phenyl group optionally having one or more substituents selected from Group G, a 6 membered aromatic heterocyclic group selected from Group V (wherein said 6 membered aromatic heterocyclic group may optionally have one or more substituents selected from Group G), a 5 membered aromatic heterocyclic group selected from W-1 to W-6 (wherein said 5 membered aromatic heterocyclic group may optionally have one or more substituents selected from Group G), a $NR^{11}R^{12}$, a $NR^{24}NR^{11}R^{12}$, or a halogen atom; and
$R^{11}$, $R^2$, and $R^{24}$ represent each independently a hydrogen atom or a C1-C3 alkyl group optionally having one or more halogen atoms;

Embodiment 13

The Present compound, wherein $R^3$ represents a C1-C6 chain hydrocarbon group optionally having one or more halogen atoms, or a halogen atom;

Embodiment 14

The Present compound, wherein $R^3$ represents a C1-C6 alkyl group having one or more halogen atoms, or a halogen atom;

Embodiment 15

The Present compound, wherein $R^6$ represents a C1-C6 alkyl group optionally having one or more halogen atoms, or a halogen atom;

Embodiment 16

The Present compound, wherein q represents 0 or 1;

Embodiment 17

The Present compound, wherein q represents 0;

Embodiment 18

The Present compound, wherein p represents 0 or 1;

Embodiment 19

The Present compound, wherein p represents 0;

Embodiment 20

The Present compound, wherein
$A^1$ represents a nitrogen atom or a $CR^4$; and
$R^4$ represents a hydrogen atom or a halogen atom;

Embodiment 21

The Present compound, wherein $A^1$ represents a nitrogen atom or a CH;

Embodiment 22

The Present compound, wherein $A^1$ represents a nitrogen atom;

Embodiment 23

The Present compound, wherein Het represents Het-1, Het-2, Het-3, or Het-4;

Embodiment 24

The Present compound, wherein Het represents Het-1, Het-2, or Het-3;

Embodiment 25

The Present compound, wherein Het represents Het-1;

Embodiment 26

The Present compound, wherein Het represents Het-2;

Embodiment 27

The Present compound, wherein Het represents Het-3;

Embodiment 28

The Present compound, wherein Het represents Het-4;

Embodiment 29

The Present compound, wherein T represents T-1, T-3, T-4, or T-5;

Embodiment 30

The Present compound, wherein T represents T-1, T-3, or T-4;

Embodiment 31

The Present compound, wherein T represents T-1 or T-3;

Embodiment 32

The Present compound, wherein T represents T-1;

Embodiment 33

The Present compound, wherein T represents T-3;

Embodiment 34

The Present compound, wherein T represents T-4;

Embodiment 35

The Present compound, wherein T represents T-5;

Embodiment 36

The Present compound, wherein T represents T-6;

Embodiment 37

The Present compound, wherein
$A^1$ represents a nitrogen atom or a $CR^4$;
$R^4$ represents a hydrogen atom or a halogen atom;
$R^1$ represents a C1-C10 chain hydrocarbon group having two or more fluorine atoms or a (C1-C5 fluoroalkoxy)C2-C5 fluoroalkyl group;
$R^2$ represents a C1-C3 alkyl group, a cyclopropyl group, or a cyclopropylmethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 38

The Present compound, wherein
$A^1$ represents a nitrogen atom or a $CR^4$;
$R^4$ represents a hydrogen atom or a halogen atom;
$R^1$ represents a C1-C10 chain hydrocarbon group having two or more halogen atoms;
$R^2$ represents a C1-C3 alkyl group, a cyclopropyl group, or a cyclopropylmethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 39

The Present compound, wherein
$A^1$ represents a nitrogen atom or a $CR^4$;
$R^4$ represents a hydrogen atom or a halogen atom;
$R^1$ represents a C1-C10 alkyl group having three or more fluorine atoms;
$R^2$ represents a C1-C3 alkyl group, a cyclopropyl group, or a cyclopropylmethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 40

The Present compound, wherein
$A^1$ represents a nitrogen atom or a $CR^4$;
$R^4$ represents a hydrogen atom or a halogen atom;
$R^1$ represents a C1-C10 perfluoroalkyl group;
$R^2$ represents a C1-C3 alkyl group, a cyclopropyl group, or a cyclopropylmethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 41

The Present compound, wherein
$A^1$ represents a nitrogen atom or a $CR^4$;
$R^4$ represents a hydrogen atom or a halogen atom;
$R^1$ represents a C1-C10 chain hydrocarbon group having two or more halogen atoms;
$R^2$ represents a methyl group or an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and $R^6$ represents a C1-C6 alkyl group optionally having one or more halogen atoms, or a halogen atom;

Embodiment 42

The Present compound, wherein
$A^1$ represents a nitrogen atom or a $CR^4$;
$R^4$ represents a hydrogen atom or a halogen atom;
$R^1$ represents a C1-C10 alkyl group having three or more fluorine atoms;
$R^2$ represents a methyl group or an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^2$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 43

The Present compound, wherein
$A^1$ represents a nitrogen atom or a $CR^4$;
$R^4$ represents a hydrogen atom or a halogen atom;
$R^1$ represents a C1-C10 perfluoroalkyl group;
$R^2$ represents a methyl group or an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 44

The Present compound, wherein
$A^1$ represents a nitrogen atom or a $CR^4$;
$R^4$ represents a hydrogen atom or a halogen atom;
$R^1$ represents a C1-C10 chain hydrocarbon group having two or more halogen atoms;
$R^2$ represents an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 45

The Present compound, wherein
$A^1$ represents a nitrogen atom or a $CR^4$;
$R^4$ represents a hydrogen atom or a halogen atom;
$R^1$ represents a C1-C10 alkyl group having three or more fluorine atoms;
$R^2$ represents an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 46

The Present compound, wherein
$A^1$ represents a nitrogen atom or a $CR^4$;
$R^4$ represents a hydrogen atom or a halogen atom;
$R^1$ represents a C1-C10 perfluoroalkyl group;
$R^2$ represents an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and
$R^6$ represents a C1-C6 alkyl group optionally having one or more halogen atoms, or a halogen atom;

Embodiment 47

The Present compound, wherein
$A^1$ represents a nitrogen atom;
$R^1$ represents a C1-C10 chain hydrocarbon group having two or more halogen atoms;
$R^2$ represents an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR$^{12}$, a NR$^{11}$R$^{12}$, a NR$^{11a}$R$^{12}$, a NR$^{24}$NR$^{11}$R$^{12}$, or a halogen atom; and R$^6$ represents a C1-C6 alkyl group optionally having one or more halogen atoms, or a halogen atom;

Embodiment 48

The Present compound, wherein
A$^1$ represents a nitrogen atom;
R$^1$ represents a C1-C10 alkyl group having three or more fluorine atoms;
R$^2$ represents an ethyl group;
R$^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR$^{12}$, a NR$^{11}$R$^{12}$, a NR$^{11a}$R$^{12a}$, a NR$^{24}$NR$^{11}$R$^{12}$, or a halogen atom; and
R$^6$ represents a C1-C6 alkyl group optionally having one or more halogen atoms, or a halogen atom;

Embodiment 49

The Present compound, wherein
A$^1$ represents a nitrogen atom;
R$^1$ represents a C1-C10 perfluoroalkyl group;
R$^2$ represents an ethyl group;
R$^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR$^{12}$, a NR$^{11}$R$^{12}$, a NR$^{11a}$R$^{12a}$, a NR$^{24}$NR$^{11}$R$^{12}$, Or a halogen atom; and
R$^6$ represents a C1-C6 alkyl group optionally having one or more halogen atoms, or a halogen atom;

Embodiment 50

The Present compound, wherein
A$^1$ represents a nitrogen atom or a CR$^4$;
R$^4$ represents a hydrogen atom or a halogen atom;
R$^1$ represents a C1-C10 chain hydrocarbon group having two or more halogen atoms;
R$^2$ represents an ethyl group;
R$^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR$^{12}$, a NR$^{11}$R$^{12}$, a NR$^{11a}$R$^{12a}$, a NR$^{24}$NR$^{11}$R$^{12}$, or a halogen atom; and
R$^6$ represents a C1-C6 alkyl group optionally having one or more halogen atoms, or a halogen atom;

Embodiment 51

The Present compound, wherein
A$^1$ represents a nitrogen atom or a CR$^4$;
R$^4$ represents a hydrogen atom or a halogen atom;
R$^1$ represents a C1-C10 alkyl group having three or more fluorine atoms;
R$^2$ represents an ethyl group;
R$^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR$^{12}$, a NR$^{11}$R$^{12}$, a NR$^{11a}$R$^{12a}$, a NR$^{24}$NR$^{11}$R$^{12}$, or a halogen atom; and
R$^6$ represents a C1-C6 alkyl group optionally having one or more halogen atoms, or a halogen atom;

Embodiment 52

The Present compound, wherein
A$^1$ represents a nitrogen atom or a CR$^4$;
R$^4$ represents a hydrogen atom or a halogen atom;
R$^1$ represents a C1-C10 perfluoroalkyl group;
R$^2$ represents an ethyl group;
R$^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a OR$^{12}$, a NR$^{11}$R$^{12}$, a NR$^{11a}$R$^{12a}$, a NR$^{24}$NR$^{11}$R$^{12}$, or a halogen atom; and
R$^6$ represents a C1-C6 alkyl group optionally having one or more halogen atoms, or a halogen atom;

Embodiment 53

The Present compound, wherein
A$^1$ represents a nitrogen atom or a CR$^4$;
R$^4$ represents a hydrogen atom or a halogen atom;
R$^1$ represents a C1-C10 chain hydrocarbon group having two or more halogen atoms;
R$^2$ represents an ethyl group;
R$^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and $R^6$ represents a C1-C6 alkyl group optionally having one or more halogen atoms, or a halogen atom;

Embodiment 54

The Present compound, wherein
$A^1$ represents a nitrogen atom or a $CR^4$;
$R^4$ represents a hydrogen atom or a halogen atom;
$R^1$ represents a C1-C10 alkyl group having three or more fluorine atoms;
$R^2$ represents an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and $R^6$ represents a C1-C6 alkyl group optionally having one or more halogen atoms, or a halogen atom;

Embodiment 55

The Present compound, wherein
$A^1$ represents a nitrogen atom or a $CR^4$;
$R^4$ represents a hydrogen atom or a halogen atom;
$R^1$ represents a C1-C10 perfluoroalkyl group;
$R^2$ represents an ethyl group;
$R^3$ represents a C1-C6 chain hydrocarbon group optionally having one or more substituents selected from Group B, a phenyl group optionally having one or more substituents selected from Group D, a 6 membered aromatic heterocyclic group selected from Group V (wherein said 6 membered aromatic heterocyclic group may optionally have one or more substituents selected from Group D), a 5 membered aromatic heterocyclic group selected from Group W (wherein said 5 membered aromatic heterocyclic group may optionally have one or more substituents selected from Group D), a $OR^{12}$, a $NR^{11}R^{12}$, a $NR^{11a}R^{12a}$, a $NR^{24}NR^{11}R^{12}$, or a halogen atom; and $R^6$ represents a C1-C6 alkyl group optionally having one or more halogen atoms, or a halogen atom;

Embodiment 56

The compound according to any one of [Embodiment 37] to [Embodiment 55], wherein
Het represents Het-1, Het-2, Het-3, or Het-4; and
T represents T-1, T-3, T-4, or T-5;

Embodiment 57

The compound according to any one of [Embodiment 37] to [Embodiment 55], wherein
Het represents Het-1, Het-2, Het-3, or Het-4; and
T represents T-1, T-3, or T-4;

Embodiment 58

The compound according to any one of [Embodiment 37] to [Embodiment 55], wherein
Het represents Het-1, Het-2, Het-3, or Het-4; and
T represents T-1 or T-3;

Embodiment 59

The compound according to any one of [Embodiment 37] to [Embodiment 55], wherein
Het represents Het-1, Het-2, or Het-3; and
T represents T-1, T-3, T-4, or T-5;

Embodiment 60

The compound according to any one of [Embodiment 37] to [Embodiment 55], wherein
Het represents Het-1, Het-2, or Het-3; and
T represents T-1, T-3, or T-4;

Embodiment 61

The compound according to any one of [Embodiment 37] to [Embodiment 55], wherein Het represents Het-1, Het-2, or Het-3; and
T represents T-1 or T-3;

Embodiment 62

The compound according to any one of [Embodiment 37] to [Embodiment 55], wherein
Het represents Het-1; and
T represents T-1, T-3, T-4, or T-5;

Embodiment 63

The compound according to any one of [Embodiment 37] to [Embodiment 55], wherein
Het represents Het-1; and
T represents T-1, T-3, or T-4;

Embodiment 64

The compound according to any one of [Embodiment 37] to [Embodiment 55], wherein
Het represents Het-1; and
T represents T-1 or T-3;

Embodiment 65

The compound according to any one of [Embodiment 37] to [Embodiment 55], wherein
Het represents Het-2; and
T represents T-1, T-3, T-4, or T-5;

Embodiment 66

The compound according to any one of [Embodiment 37] to [Embodiment 55], wherein
Het represents Het-2; and
T represents T-1, T-3, or T-4;

Embodiment 67

The compound according to any one of [Embodiment 37] to [Embodiment 55], wherein
Het represents Het-2; and
T represents T-1 or T-3;

Embodiment 68

The compound according to any one of [Embodiment 37] to [Embodiment 55], wherein
Het represents Het-3; and
T represents T-1 or T-3;

Embodiment 69

The compound according to any one of [Embodiment 37] to [Embodiment 55], wherein
Het represents Het-4; and
T represents T-1 or T-3;

Embodiment 70

The compound according to any one of [Embodiment 37] to [Embodiment 55], wherein
Het represents Het-1, Het-2, Het-3, or Het-4; and
T represents T-1;

Embodiment 71

The compound according to any one of [Embodiment 37] to [Embodiment 55], wherein
Het represents Het-1, Het-2, or Het-3; and
T represents T-1;

Embodiment 72

The compound according to any one of [Embodiment 37] to [Embodiment 55], wherein
Het represents Het-1; and
T represents T-1;

Embodiment 73

The compound according to any one of [Embodiment 37] to [Embodiment 55], wherein
Het represents Het-2; and
T represents T-1;

Embodiment 74

The compound according to any one of [Embodiment 37] to [Embodiment 55], wherein
Het represents Het-3; and
T represents T-1;

Embodiment 75

The compound according to any one of [Embodiment 37] to [Embodiment 55], wherein
Het represents Het-4; and
T represents T-1;

Embodiment 76

The compound according to any one of [Embodiment 37] to [Embodiment 55], wherein
Het represents Het-1, Het-2, Het-3, or Het-4;
T represents T-1; and
$R^1$ represents a C2-C10 perfluoroalkyl group;

Embodiment 77

The compound according to any one of [Embodiment 37] to [Embodiment 55], wherein
Het represents Het-1, Het-2, or Het-3;
T represents T-1; and
$R^1$ represents a C2-C10 perfluoroalkyl group;

Embodiment 78

The compound according to any one of [Embodiment 37] to [Embodiment 55], wherein
Het represents Het-1;
T represents T-1; and
$R^1$ represents a C2-C10 perfluoroalkyl group;

Embodiment 79

The compound according to any one of [Embodiment 37] to [Embodiment 55], wherein
Het represents Het-2;
T represents T-1; and
$R^1$ represents a C2-C10 perfluoroalkyl group;

Embodiment 80

The compound according to any one of [Embodiment 37] to [Embodiment 55], wherein
Het represents Het-3;
T represents T-1; and
$R^1$ represents a C2-C10 perfluoroalkyl group; and

Embodiment 81

The compound according to any one of [Embodiment 37] to [Embodiment 55], wherein
Het represents Het-4;
T represents T-1; and
$R^1$ represents a C2-C10 perfluoroalkyl group;

Next, processes for preparing the Present compound are described.

The Present compound can be prepared, for example, according to the following processes.

Process 1

The Present compound wherein n represents 1 (hereinafter referred to as "Present compound (Ib)") and the Present compound wherein n represents 2 (hereinafter referred to as "Present compound (Ic)") may be prepared by reacting the Present compound wherein n represents 0 (hereinafter referred to as "Present compound (Ia)") with an oxidizing agent.

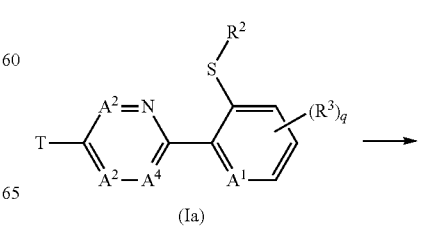

(Ia)

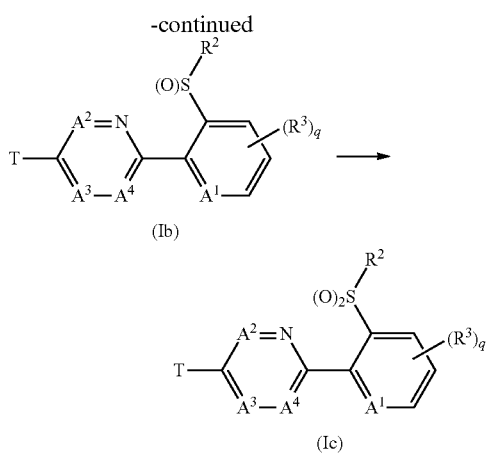

(Ib)

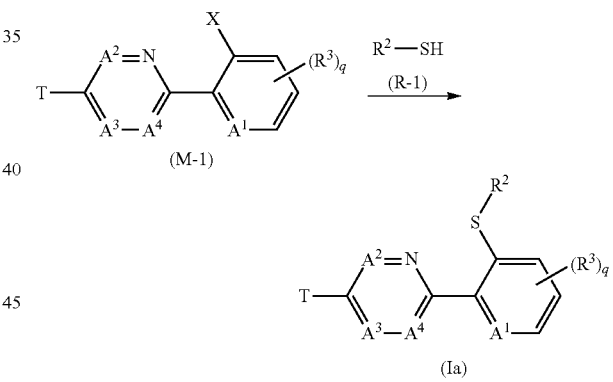

(Ic)

[wherein the symbols are the same as defined above.]

First, a process for preparing the Compound (Ib) from the Compound (Ia) is described.

The reaction is usually carried out in the presence of a solvent. Examples of the solvent to be used in the reaction include aliphatic halogenated hydrocarbons such as dichloromethane and chloroform (hereinafter collectively referred to as "aliphatic halogenated hydrocarbons"); nitriles such as acetonitrile (hereinafter collectively referred to as "nitriles"); alcohols such as methanol and ethanol (hereinafter collectively referred to as "alcohols"); acetic acid; water; and mixed solvents thereof.

Examples of the oxidizing agent to be used in the reaction include sodium periodate, m-chloroperbenzoic acid (hereinafter referred to as "mCPBA"), and hydrogen peroxide.

When hydrogen peroxide is used as the oxidizing agent, a base or a catalyst may be added to the reaction as needed.

Examples of the base to be used in the reaction include sodium carbonate.

Examples of the catalyst to be used in the reaction include tungstic acid and sodium tungstate.

In the reaction, the oxidizing agent is usually used within a range of 1 to 1.2 molar ratio(s), the base is usually used within a range of 0.01 to 1 molar ratio, and the catalyst is usually used within a range of 0.01 to 0.5 molar ratio, relative to 1 mole of the Compound (Ia).

The reaction temperature of the reaction is usually within a range of −20 to 80° C. The reaction period of the reaction is usually within a range of 0.1 to 12 hours.

When the reaction is completed, to the reaction mixture is added water, the reaction mixture is extracted with organic solvent(s), and the organic layers are washed with an aqueous solution of a reducing agent (for example, sodium sulfite or sodium thiosulfate) and an aqueous solution of a base (for example, sodium hydrogen carbonate) as needed. The organic layers are dried, and concentrated to give the Compound (Ib).

Next, a process for preparing the Compound (Ic) from the Compound (Ib) is described.

The reaction is usually carried out in the presence of a solvent. Examples of the solvent to be used in the reaction include aliphatic halogenated hydrocarbons, nitriles, alcohols, acetic acid, water, and mixed solvents thereof.

Examples of the oxidizing agent to be used in the reaction include mCPBA and hydrogen peroxide.

When hydrogen peroxide is used as the oxidizing agent, sodium carbonate or a catalyst may be added to the reaction as needed.

Examples of the catalyst to be used in the reaction include sodium tungstate.

In the reaction, the oxidizing agent is usually used within a range of 1 to 2 molar ratio(s), the sodium carbonate is usually used within a range of 0.01 to 1 molar ratio, and the catalyst is usually used within a range of 0.01 to 0.5 molar ratio, relative to 1 mole of the Compound (Ib).

The reaction temperature of the reaction is usually within a range of −20 to 120° C. The reaction period of the reaction is usually within a range of 0.1 to 12 hours.

When the reaction is completed, to the reaction mixture is added water, the reaction mixture is extracted with organic solvent(s), and the organic layers are washed with an aqueous solution of a reducing agent (for example, sodium sulfite or sodium thiosulfate) and an aqueous solution of a base (for example, sodium hydrogen carbonate) as needed. The organic layers are dried, and concentrated to give the Compound (Ic).

Also, the Compound (Ic) may be prepared in one step reaction (one-pot) by reacting the Compound (Ia) with an oxidizing agent.

The reaction may be carried out by using the oxidizing agent usually at 2 to 5 molar ratios relative to 1 mole of the Compound (Ia) according to the process for preparing the Compound (Ic) from the Compound (Ib).

Process 2

The Present compound (Ia) may be prepared by reacting a compound represented by formula (M-1) (hereinafter referred to as "Compound (M-1)") with a compound represented by formula (R-1) (hereinafter referred to as "Compound (R-1)") in the presence of a base.

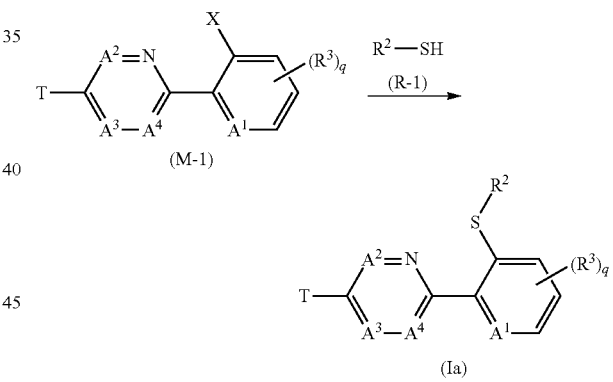

[wherein: X represents a halogen atom; and the other symbols are the same as defined above.]

The reaction is usually carried out in the presence of a solvent. Examples of the solvent to be used in the reaction include ethers such as tetrahydrofuran (hereinafter referred to as "THF"), ethylene glycol dimethyl ether, methyl-tert-butyl ether (hereinafter referred to as "MTBE"), and 1,4-dioxane (hereinafter collectively referred to as "ethers"); aromatic hydrocarbons such as toluene and xylene (hereinafter collectively referred to as "aromatic hydrocarbons"); nitriles; aprotic polar solvents such as dimethylformamide (hereinafter referred to as "DMF"), N-methylpyrrolidone (hereinafter referred to as "NMP"), and dimethyl sulfoxide (hereinafter referred to as "DMSO") (hereinafter collectively referred to as "aprotic polar solvents"); and mixed solvents thereof.

Examples of the base to be used in the reaction include alkali metal carbonates such as sodium carbonate and potassium carbonate (hereinafter collectively referred to as "alkali metal carbonates"); and alkali metal hydrides such as sodium hydride (hereinafter collectively referred to as "alkali metal hydrides").

In the reaction, the Compound (R-1) is usually used within a range of 1 to 10 molar ratio(s), and the base is usually used within a range of 1 to 10 molar ratio(s), relative to 1 mole of the Compound (M-1).

The reaction temperature of the reaction is usually within a range of −20° C. to 150° C. The reaction period of the reaction is usually within a range of 0.5 to 24 hour(s).

When the reaction is completed, to the reaction mixture is added water, the reaction mixture is extracted with organic solvent(s), and the organic layers are worked up (for example, dried or concentrated) to give the Compound (Ia).

In the reaction, X is preferably a fluorine atom or a chlorine atom.

Process 3

The Present compound represented by formula (Id) (hereinafter referred to as "Present compound (Id)") may be prepared by reacting a compound represented by formula (M-2) (hereinafter referred to as "Compound (M-2)") with a compound represented by formula (R-2) (hereinafter referred to as "Compound (R-2)") in the presence of copper.

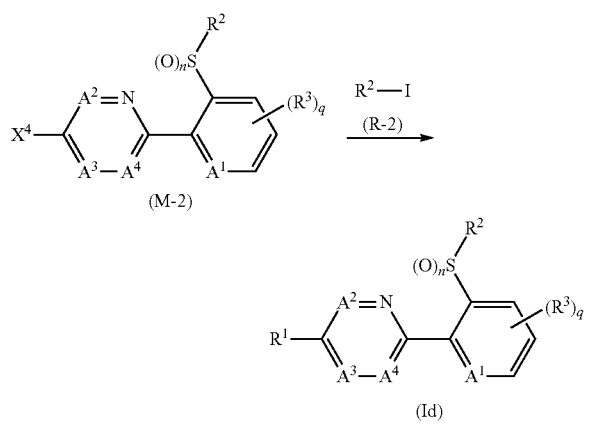

[wherein: $X^4$ represents a chlorine atom, a bromine atom, or an iodine atom; and the other symbols are the same as defined above.]

The Compound (R-2) is a commercially available compound or may be prepared according to a known method.

The reaction is usually carried out in a solvent. Examples of the solvent to be used in the reaction include aromatic hydrocarbons, aprotic polar solvents, and mixed solvents thereof.

In the reaction, the Compound (R-2) is usually used within a range of 1 to 10 molar ratio(s), and the copper is usually used within a range of 1 to 10 molar ratio(s), relative to 1 mole of the Compound (M-2).

The reaction temperature of the reaction is usually within a range of 40° C. to 200° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Present compound (Id).

Process 4

The Present compound represented by formula (Ie) (hereinafter referred to as "Present compound (Ie)") may be prepared by reacting the Compound (M-2) with a compound represented by formula (R-3) (hereinafter referred to as "Compound (R-3)") in the presence of a palladium catalyst.

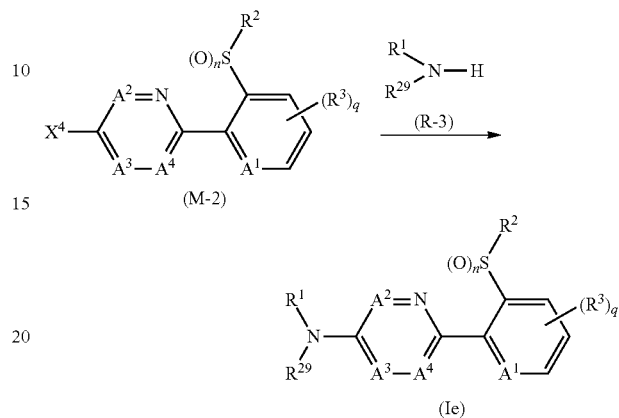

[wherein the symbols are the same as defined above.]

The Compound (R-3) is a commercially available compound or may be prepared according to a known method.

The reaction is usually carried out in a solvent. Examples of the solvent to be used in the reaction include ethers, aromatic hydrocarbons, aprotic polar solvents, and mixed solvents thereof.

Examples of the palladium catalyst include allylpalladium (II) chloride.

In the reaction, phenol is used as an additive, and potassium tert-butoxide is used as a base.

In the reaction, the Compound (R-3) is usually used within a range of 1 to 10 molar ratio(s), the palladium catalyst is usually used within a range of 0.01 to 1 molar ratio, phenol is usually used within a range of 1 to 5 molar ratio(s), and potassium tert-butoxide is usually used within a range of, relative to 1 mole of the Compound (M-2).

The reaction temperature of the reaction is usually within a range of 40° C. to 180° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Present compound (Ie).

Process 5

The Present compound represented by formula (If) (hereinafter referred to as "Present compound (If)") may be prepared by reacting a compound represented by formula (M-3) (hereinafter referred to as "Compound (M-3)") with a compound represented by formula (R-4) (hereinafter referred to as "Compound (R-4)") in the presence of a base.

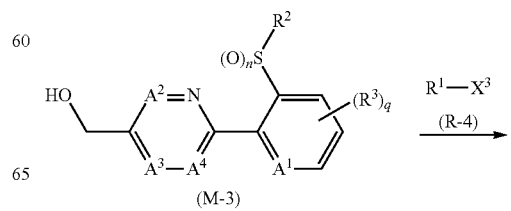

-continued

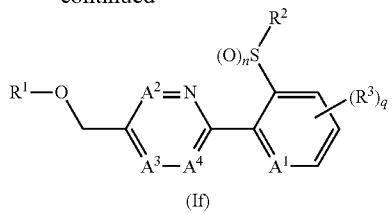

(If)

[wherein: $X^3$ represents a chlorine atom, a bromine atom, an iodine atom, a C1-C10 perfluoroalkylsulfonyloxy group, or a tosyloxy group; and the other symbols are the same as defined above.]

The Compound (R-4) is a commercially available compound or may be prepared according to a known method.

The reaction is usually carried out in a solvent. Examples of the solvent to be used in the reaction include ethers, aromatic hydrocarbons, aprotic polar solvents, and mixed solvents thereof.

Examples of the base to be used in the reaction include organic bases, alkali metal hydrides, and alkali metal carbonates.

In the reaction, the Compound (R-4) is usually used within a range of 1 to 10 molar ratio(s), and the base is usually used within a range of 0.1 to 5 molar ratio(s), relative to 1 mole of the Compound (M-3).

The reaction temperature of the reaction is usually within a range of −20° C. to 120° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Present compound (If)

Process 6

The Present compound represented by formula (Ig) (hereinafter referred to as "Present compound (Ig)") may be prepared by reacting a compound represented by formula (M-4) (hereinafter referred to as "Compound (M-4)") with a compound represented by formula (R-5) (hereinafter referred to as "Compound (R-5)").

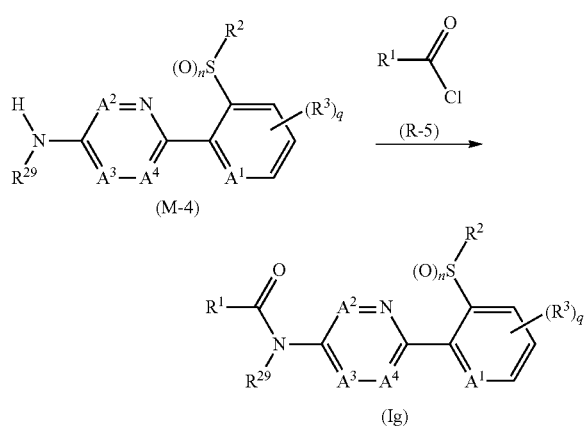

[wherein the symbols are the same as defined above.]

The Compound (R-5) is a commercially available compound or may be prepared according to a known method.

The reaction is usually carried out in a solvent. Examples of the solvent to be used in the reaction include ethers, aliphatic halogenated hydrocarbons, aromatic hydrocarbons, aprotic polar solvents, and mixed solvents thereof.

A base may be added to the reaction as needed. Examples of the base to be used in the reaction include organic bases.

In the reaction, the Compound (R-5) is usually used within a range of 1 to 10 molar ratio(s), and the base is usually used within a range of 0.1 to 10 molar ratio(s), relative to 1 mole of the Compound (M-4).

The reaction temperature of the reaction is usually within a range of −20° C. to 120° C. The reaction period of the reaction is usually within a range of 0.1 to 24 hour(s) When the reaction is completed, to the reaction mixture is added water, the reaction mixture is extracted with organic solvent(s), and the organic layers are worked up (for example, dried or concentrated) to give the Present compound (Ig).

Process 7

The Present compound represented by formula (Ih) (hereinafter referred to as "Present compound (Ih)") may be prepared by reacting the Compound (M-2) with a compound represented by formula (R-6) (hereinafter referred to as "Compound (R-6)") in the presence of a base.

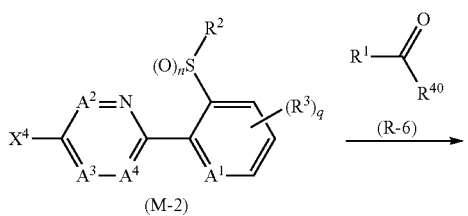

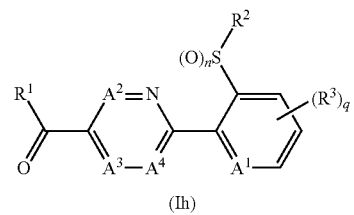

(Ih)

[wherein: $R^{40}$ represents a methoxy group, an ethoxy group, a phenoxy group, or a $N(CH_3)OCH_3$; and the other symbols are the same as defined above.]

The Compound (R-6) is a commercially available compound or may be prepared according to a known method.

The reaction is usually carried out in a solvent. Examples of the solvent to be used in the reaction include ethers and aromatic hydrocarbons.

Examples of the base to be used in the reaction include butyllithium, lithium diisopropylamide, lithium tetramethylpiperidide, and lithium bis(trimethylsilyl)amide.

In the reaction, the Compound (R-6) is usually used within a range of 1 to 10 molar ratio(s), and the base is usually used within a range of 1.0 to 2.0 molar ratio(s), relative to 1 mole of the Compound (M-2).

The reaction temperature of the reaction is usually within a range of −100° C. to 60° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Present compound (Ih).

$X^4$ is preferably a bromine atom or an iodine atom.

Process 8

The Present compound represented by formula (Ii) (hereinafter referred to as "Present compound (Ii)") may be prepared by reacting a compound represented by formula (M-18) (hereinafter referred to as "Compound (M-18)") with a compound represented by formula (R-7) (hereinafter referred to as "Compound (R-7)") in the presence of a condensing agent.

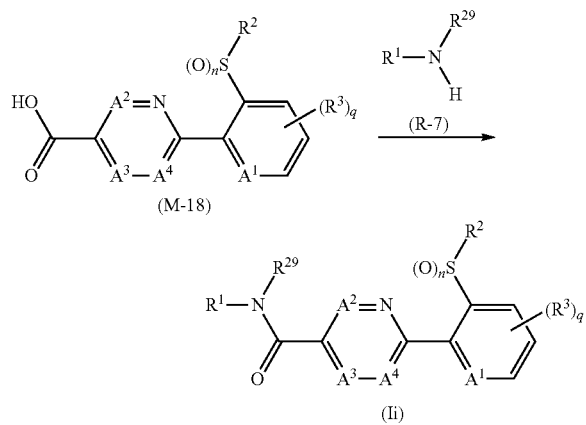

[wherein the symbols are the same as defined above.]

The Compound (R-7) is a commercially available compound or may be prepared according to a known method.

The reaction is usually carried out in a solvent. Examples of the solvent to be used in the reaction include ethers, aliphatic halogenated hydrocarbons, aromatic hydrocarbons, aprotic polar solvents, and mixed solvents thereof.

Examples of the condensing agent to be used in the reaction include 1-ethyl-3-(3-dimethylaminopropyl)carbodiimide hydrochloride.

A base may be added to the reaction as needed. Examples of the base to be used in the reaction include organic bases.

In the reaction, the Compound (R-7) is usually used within a range of 1 to 10 molar ratio(s), the condensing agent is usually used within a range of 1 to 5 molar ratio(s), and the base is usually used within a range of 0.1 to 10 molar ratio(s), relative to 1 mole of the Compound (M-18).

The reaction temperature of the reaction is usually within a range of −20° C. to 120° C. The reaction period of the reaction is usually within a range of 0.1 to 24 hour(s) When the reaction is completed, to the reaction mixture is added water, the reaction mixture is extracted with organic solvent(s), and the organic layers are worked up (for example, dried or concentrated) to give the Present compound (Ii).

Process 9

The Present compound represented by formula (Ij) (hereinafter referred to as "Present compound (Ij)") may be prepared by reacting a compound represented by formula (M-6) (hereinafter referred to as "Compound (M-6)") with a compound represented by formula (R-8) (hereinafter referred to as "Compound (R-8)").

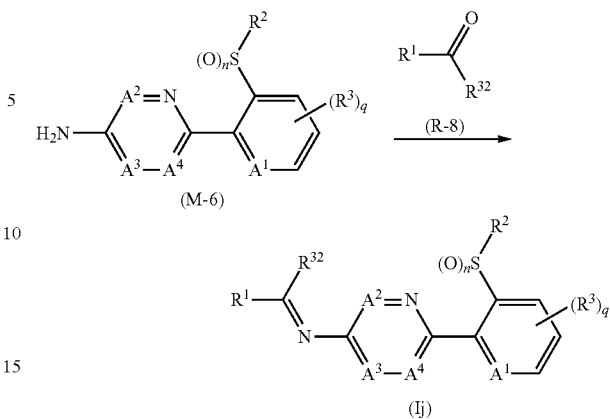

[wherein the symbols are the same as defined above.]

The Compound (R-8) is a commercially available compound or may be prepared according to a known method.

The reaction is usually carried out in a solvent. Examples of the solvent to be used in the reaction include ethers, aliphatic halogenated hydrocarbons, aromatic hydrocarbons, aprotic polar solvents, and mixed solvents thereof.

An acid may be added to the reaction as needed. Examples of the acid to be used in the reaction include p-toluenesulfonic acid and camphorsulfonic acid.

In the reaction, the Compound (R-8) is usually used within a range of 1 to 10 molar ratio(s), and the acid is usually used within a range of 0.1 to 10 molar ratio(s), relative to 1 mole of the Compound (M-6).

The reaction temperature of the reaction is usually within a range of −20° C. to 180° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Present compound (Ij).

Hereinafter, processes for preparing each Intermediate compound are described.

Reference Process 1

The Compound (M-2) wherein X represents a chlorine atom or a bromine atom (hereinafter referred to as "Compound (M-2a)"), and the Compound (M-2) wherein X represents a fluorine atom or an iodine atom (hereinafter referred to as "Compound (M-2b)") may be prepared according to the following process.

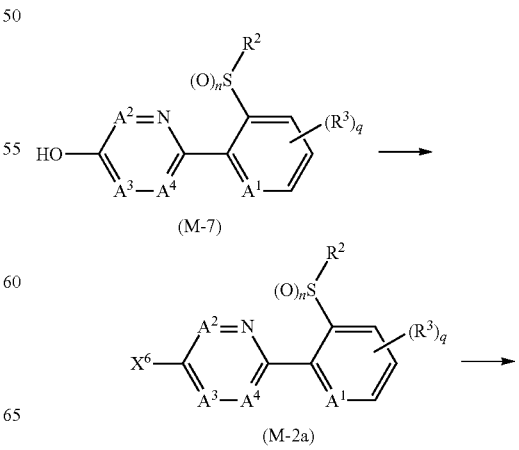

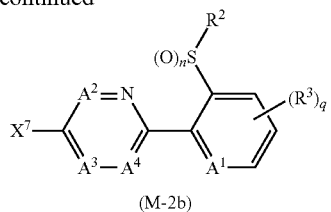

(M-2b)

[wherein: $X^6$ represents a chlorine atom or a bromine atom; $X^7$ represents a fluorine atom or an iodine atom; and the other symbols are the same as defined above.]

First, a process for preparing the Compound (M-2a) from the Compound (M-7) is described.

The Compound (M-2a) may be prepared by reacting the Compound (M-7) with phosphorus oxychloride or phosphorus oxybromide.

The reaction is usually carried out in a solvent. Examples of the solvent to be used in the reaction include aromatic hydrocarbons.

When phosphorus oxychloride is used, the phosphorus oxychloride may be used also as a solvent.

In the reaction, the phosphorus oxychloride or the phosphorus oxybromide is usually used within a range of 1 to 10 molar ratio(s) relative to 1 mole of the Compound (M-7).

The reaction temperature of the reaction is usually within a range of 0° C. to 150° C. The reaction period of the reaction is usually within a range of 0.5 to 24 hour(s).

When the reaction is completed, to the reaction mixture is added water, the reaction mixture is extracted with organic solvent(s), and the organic layers are worked up (for example, dried or concentrated) to give the Compound (M-2a).

Next, a process for preparing the Compound (M-2b) from the Compound (M-2a) is described.

The Compound (M-2b) may be prepared by reacting the Compound (M-2a) with an inorganic fluoride or an inorganic iodide.

The reaction is usually carried out in a solvent. Examples of the solvent to be used in the reaction include nitriles, aprotic polar solvents, nitrogen-containing aromatic compounds, and mixed solvents thereof.

Examples of the inorganic fluoride to be used in the reaction include potassium fluoride, sodium fluoride, and fluoride cesium. Examples of the inorganic iodide to be used in the reaction include potassium iodide and sodium iodide.

In the reaction, the inorganic fluoride or the inorganic iodide is usually used within a range of 1 to 10 molar ratio(s) relative to 1 mole of the Compound (M-2a).

The reaction temperature of the reaction is usually within a range of 0° C. to 250° C. The reaction period of the reaction is usually within a range of 0.5 to 24 hour(s).

When the reaction is completed, to the reaction mixture is added water, the reaction mixture is extracted with organic solvent(s), and the organic layers are worked up (for example, dried or concentrated) to give the Compound (M-2b).

Reference Process 2

The Compound (M-7) may be prepared by dealkylating a compound represented by formula (M-10) (hereinafter referred to as "Compound (M-10)") in the presence of an acid.

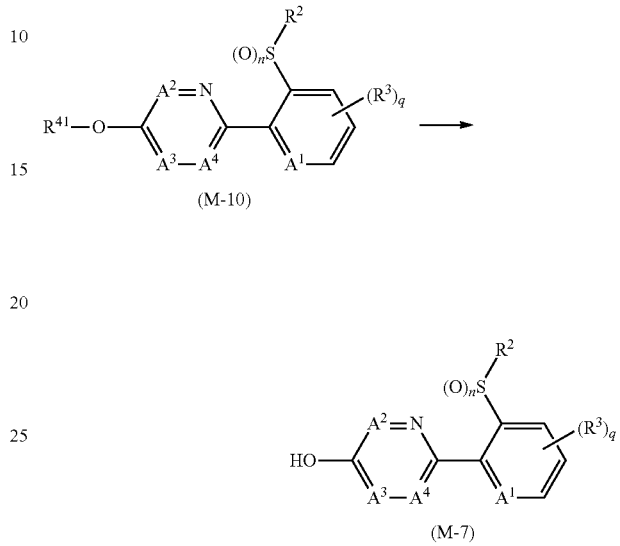

[wherein: $R^{41}$ represents a methyl group or an ethyl group; and the other symbols are the same as defined above.]

The reaction is usually carried out in a solvent. Examples of the solvent to be used in the reaction include aliphatic halogenated hydrocarbons, aromatic hydrocarbons, nitriles, alcohols, acetic acid, water, and mixed solvents thereof.

Examples of the acid to be used in the reaction include mineral acids such as hydrochloric acid; halogenated borons such as boron trichloride and boron tribromide; and titanium chloride and aluminum chloride.

In the reaction, the acid is usually used within a range of 0.1 to 10 molar ratio(s) relative to 1 mole of the Compound (M-10). When a mineral acid such as hydrochloric acid is used as an acid in the reaction, the mineral acid may be used also as a solvent.

The reaction temperature of the reaction is usually within a range of −20° C. to 150° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Compound (M-7).

Reference Process 3

The Compounds (M-10) wherein n represents 0 (hereinafter referred to as "Compound (M-10a)"), n represents 1 (hereinafter referred to as "Compound (M-10b)"), and n represents 2 (hereinafter referred to as "Compound (M-10c)") may be prepared according to the following process.

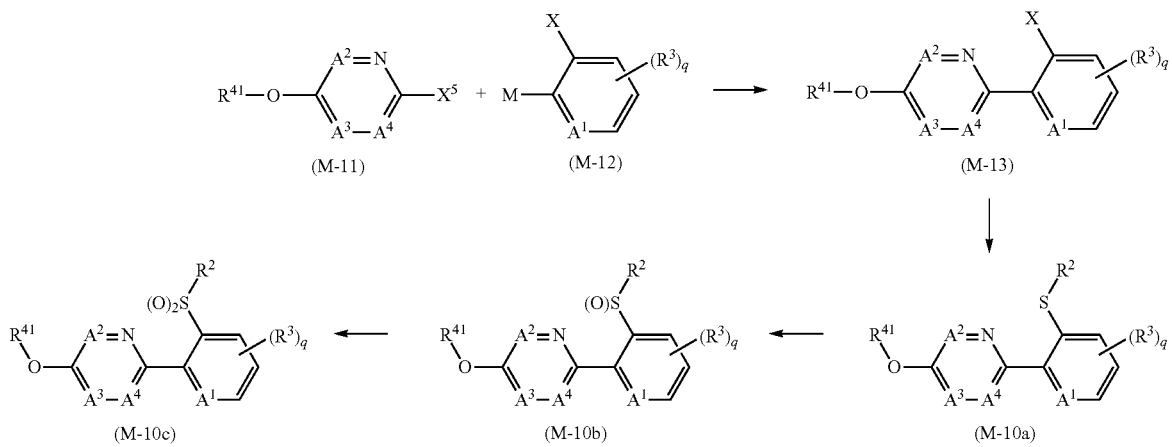

(M-11)  (M-12)  (M-13)

(M-10c)  (M-10b)  (M-10a)

[wherein: $X^5$ represents a chlorine atom, a bromine atom, or an iodine atom; M represents a Sn $(n-C_4H_9)_3$, a ZnCl, a MgCl, or a MgBr; and the other symbols are the same as defined above.]

First, a process for preparing a compound represented by formula (M-13) (hereinafter referred to as "Compound (M-13)") is described.

The Compound (M-13) may be prepared by reacting a compound represented by formula (M-11) (hereinafter referred to as "Compound (M-11)") with a compound represented by formula (M-12) (hereinafter referred to as "Compound (M-12)") in the presence of a metal catalyst.

The Compound (M-12) may be prepared according to, for example, the process described in WO 03/024961 or the process described in Organic Process Research & Development, 2004, 8, 192-200.

The reaction is usually carried out in a solvent.

Examples of the solvent to be used in the reaction include ethers, aromatic hydrocarbons, aprotic polar solvents, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalysts such as copper(I) iodide and copper(I) chloride.

A ligand, a base, and an inorganic halide may be added to the reaction as needed.

Examples of the ligand to be used in the reaction include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

Examples of the base to be used in the reaction include alkali metal hydrides, alkali metal carbonates, or organic bases.

Examples of the inorganic halide to be used in the reaction include alkali metal fluorides such as potassium fluoride and sodium fluoride; and alkali metal chlorides such as lithium chloride and sodium chloride.

In the reaction, the Compound (M-12) is usually used within a range of 1 to 10 molar ratio(s), the metal catalyst is usually used within a range of 0.01 to 0.5 molar ratio, the ligand is usually used within a range of 0.01 to 1 molar ratio, the base is usually used within a range of 0.1 to 5 molar ratio(s), and the inorganic halide is usually used within a range of 0.1 to 5 molar ratio(s), relative to 1 mole of the Compound (M-11).

The reaction temperature of the reaction is usually within a range of $-20°$ C. to $200°$ C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Compound (M-13).

The Compound (M-10a) may be prepared by using the Compound (M-13) instead of the Compound (M-1) according to the process described in the Process 2.

The Compound (M-10b) and the Compound (M-10c) may be prepared by using the Compound (M-10a) instead of the Present compound (Ia) according to the process described in the Process 1.

Reference Process 4

The Compound (M-4) may be prepared by reacting the Compound (M-2a) with a compound represented by formula (R-9) (hereinafter referred to as "Compound (R-9)").

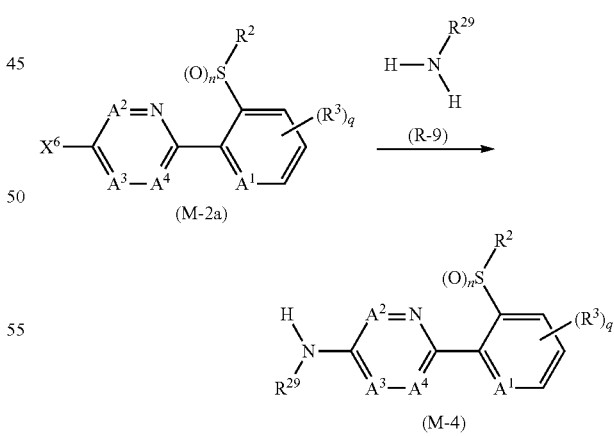

(M-2a)  (R-9)

(M-4)

[wherein the symbols are the same as defined above.]

The reaction is usually carried out in a solvent.

Examples of the solvent to be used in the reaction include ethers, aliphatic hydrocarbons, aromatic hydrocarbons, aliphatic halogenated hydrocarbons, esters, nitriles, aprotic polar solvents, nitrogen-containing aromatic compounds, and mixed solvents thereof.

A base may be added to the reaction as needed.

Examples of the base to be used in the reaction include alkali metal carbonates, alkali metal hydrides, and organic bases.

In the reaction, the Compound (R-9) is usually used within a range of 1 to 10 molar ratio(s), and the base is usually used within a range of 1 to 10 molar ratio(s), relative to 1 mole of the Compound (M-2a).

The reaction temperature of the reaction is usually within a range of 0 to 200° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Compound (M-4).

Reference Process 5

A compound represented by formula (M-3) (hereinafter referred to as "Compound (M-3)") may be prepared by reacting a compound represented by formula (M-17) (hereinafter referred to as "Compound (M-17)") with a reducing agent.

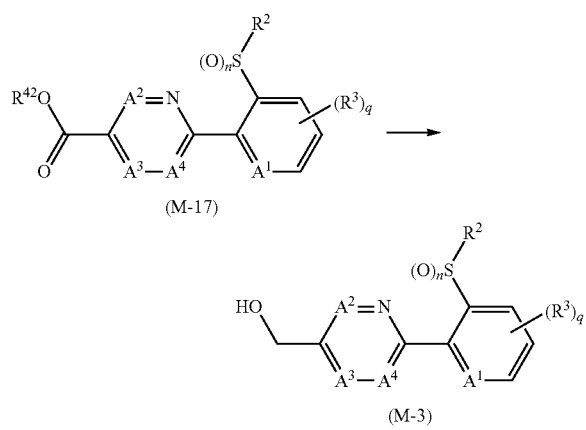

[wherein: $R^{42}$ represents a methyl group, an ethyl group, or a phenyl group; and the other symbols are the same as defined above.]

The reaction is usually carried out in a solvent. Examples of the solvent to be used in the reaction include ethers, aliphatic hydrocarbons, aromatic hydrocarbons, alcohols, and mixed solvents thereof.

Examples of the reducing agent to be used in the reaction include sodium borohydride, lithium borohydride, lithium aluminum hydride, and diisobutylaluminum hydride.

In the reaction, the reducing agent is usually used within a range of 2 to 5 molar ratios relative to 1 mole of the Compound (M-17).

The reaction temperature of the reaction is usually within a range of −20 to 120° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to give the Compound (M-3).

Reference Process 6

The Compound (M-15) may be prepared according to the following process.

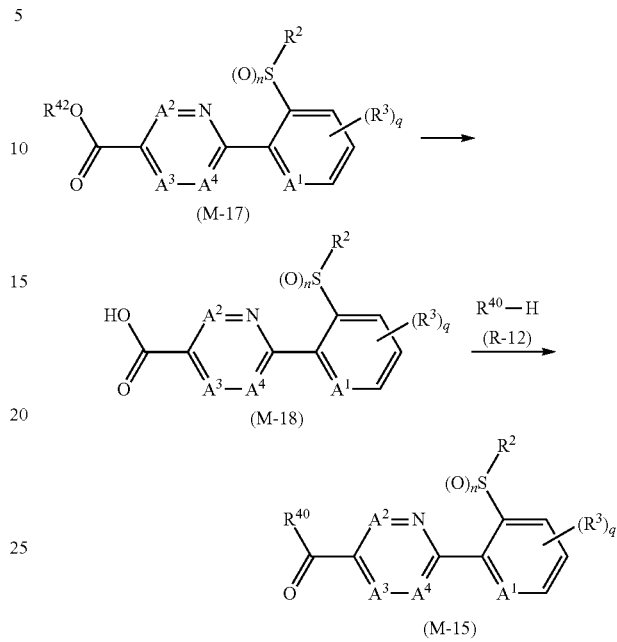

[wherein the symbols are the same as defined above.]

First, a process for preparing a compound represented by formula (M-18) (hereinafter referred to as "Compound (M-18)") is described.

The Compound (M-18) may be prepared by hydrolyzing a compound represented by formula (M-17) (hereinafter referred to as "Compound (M-17)") in the presence of an acid or a base.

The reaction is usually carried out in a solvent. Examples of the solvent to be used in the reaction include ethers, aliphatic hydrocarbons, aromatic hydrocarbons, aprotic polar solvents, alcohols, water, and mixed solvents thereof.

Examples of the acid to be used in the reaction include mineral acids such as hydrochloric acid.

Examples of the base to be used in the reaction include alkali metal hydroxides such as sodium hydroxide and potassium hydroxide.

In the reaction, the acid is used within a range of 0.1 to 5 molar ratio(s), and the base is used within a range of 1 to 5 molar ratio(s), relative to 1 mole of the Compound (M-17).

The reaction temperature of the reaction is usually within a range of 0 to 200° C. The reaction period of the reaction is usually within a range of 0.1 to 24 hour(s).

When the reaction is completed, to the reaction mixture is added water, then the reaction mixture is extracted with organic solvent(s), and the organic layers are worked up (for example, dried or concentrated) to isolate the Compound (M-18).

Next, a process for preparing the Compound (M-15) is described.

The Compound (M-15) may be prepared by reacting the Compound (M-18) with a compound represented by formula (R-12) (hereinafter referred to as "Compound (R-12)") in the presence of a condensing agent.

The reaction is usually carried out in a solvent.

Examples of the solvent to be used in the reaction include ethers, aliphatic hydrocarbons, aromatic hydrocarbons, aprotic polar solvents, and mixed solvents thereof.

Examples of the condensing agent to be used in the reaction include 1-ethyl-3-(3-dimethylaminopropyl)carbodiimide hydrochloride.

A base may be added to the reaction as needed. Examples of the base to be used in the reaction include organic bases.

In the reaction, the condensing agent is used within a range of 1 to 5 molar ratio(s), and the base is used within a range of 1 to 5 molar ratio(s), relative to 1 mole of the Compound (M-18).

The reaction temperature of the reaction is usually within a range of 0 to 200° C. The reaction period of the reaction is usually within a range of 0.1 to 24 hour(s).

When the reaction is completed, to the reaction mixture is added water, the reaction mixture is extracted with organic solvent(s), and the organic layers are worked up (for example, dried or concentrated) to isolate the Compound (M-15).

Reference Process 7

The Compounds (M-17) wherein n represents 0 (hereinafter referred to as "Compound (M-17a)"), n represents 1 (hereinafter referred to as "Compound (M-17b)"), and n represents 2 (hereinafter referred to as "Compound (M-17c)") may be prepared according to the following process.

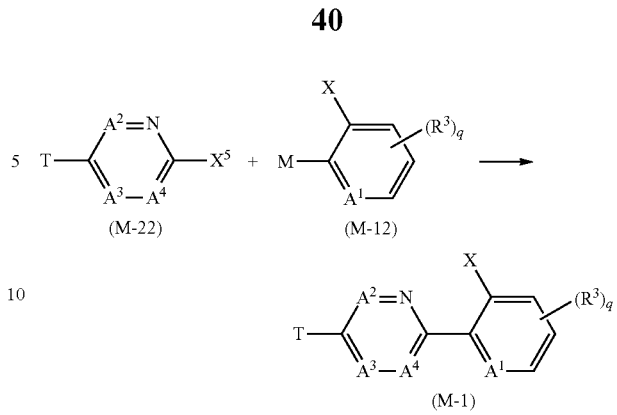

[wherein the symbols are the same as defined above.]

The Compound (M-1) may be prepared by using the Compound (M-22) instead of the Compound (M-11) according to the process described in the Reference process 3.

The Compound (M-22) is a commercially available compound or may be prepared according to a known method.

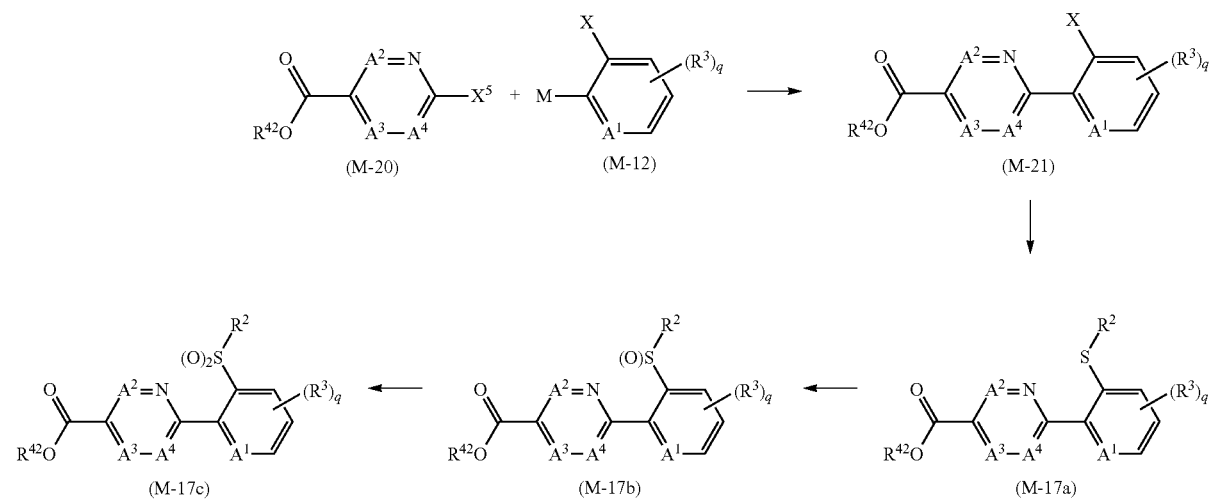

[wherein the symbols are the same as defined above.]

The Compound (M-21) may be prepared by using a compound represented by formula (M-20) (hereinafter referred to as "Compound (M-20)") instead of the Compound (M-11) according to the process described in the Reference process 3.

The Compound (M-17a) may be prepared by using the Compound (M-21) instead of the Compound (M-1) according to the process described in the Process 2.

The Compound (M-17b) and the Compound (M-17c) may be prepared by using the Compound (M-17a) instead of the Present compound (Ia) according to the process described in the Process 1.

Reference Process 8

The Compound (M-1) may be prepared by reacting a compound represented by formula (M-22) (hereinafter referred to as "Compound (M-22)") with the Compound (M-12) in the presence of a catalyst.

Next, specific examples of the Present compound are shown below.

-continued

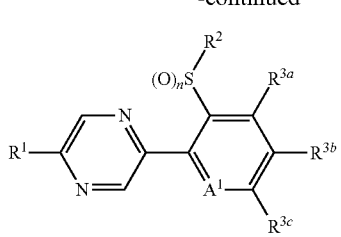
(I-E)

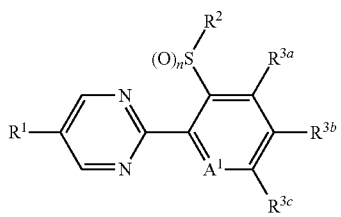
(I-F)

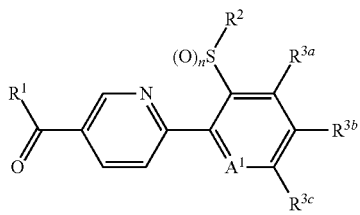
(I-G)

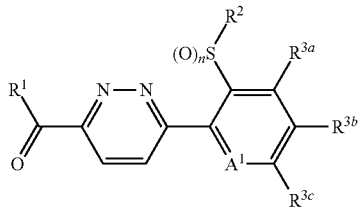
(I-H)

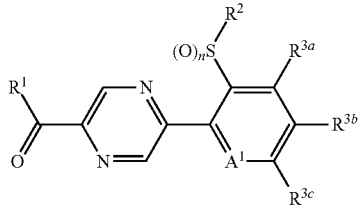
(I-I)

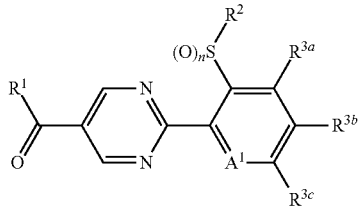
(I-J)

The Present compound represented by formula (I-C), formula (I-D), formula (I-E), formula (I-F), formula (I-G), formula (I-H), formula (I-I), or formula (I-J), wherein $A^1$ represents a nitrogen atom;

n represents 2;

$R^{3a}$, $R^{3b}$, and $R^{3c}$ represent each a hydrogen atom; and $R^1$ and $R^2$ represent any one combination indicated in Table 1 to Table 5

(hereinafter referred to as "Compound group SX1").

The Present compound represented by formula (I-C), formula (I-D), formula (I-E), formula (I-F), formula (I-G), formula (I-H), formula (I-I), or formula (I-J), wherein $A^1$ represents a nitrogen atom;

n represents 1;

$R^{3a}$, $R^{3b}$, and $R^{3c}$ represent each a hydrogen atom; and $R^1$ and $R^2$ represent any one combination indicated in Table 1 to Table 5

(hereinafter referred to as "Compound group SX2").

The Present compound represented by formula (I-C), formula (I-D), formula (I-E), formula (I-F), formula (I-G), formula (I-H), formula (I-I), or formula (I-J), wherein $A^1$ represents a nitrogen atom;

n represents 0;

$R^{3a}$, $R^{3b}$, and $R^{3c}$ represent each a hydrogen atom; and $R^1$ and $R^2$ represent any one combination indicated in Table 1 to Table 5

(hereinafter referred to as "Compound group SX3").

The Present compound represented by formula (I-C), formula (I-D), formula (I-E), formula (I-F), formula (I-G), formula (I-H), formula (I-I), or formula (I-J), wherein $A^1$ represents a CH;

n represents 2;

$R^{3a}$, $R^{3b}$, and $R^{3c}$ represent each a hydrogen atom; and $R^1$ and $R^2$ represent any one combination indicated in Table 1 to Table 5

(hereinafter referred to as "Compound group SX4").

The Present compound represented by formula (I-C), formula (I-D), formula (I-E), formula (I-F), formula (I-G), formula (I-H), formula (I-I), or formula (I-J), wherein $A^1$ represents a CH;

n represents 1;

$R^{3a}$, $R^{3b}$, and $R^{3c}$ represent each a hydrogen atom; and $R^1$ and $R^2$ represent any one combination indicated in Table 1 to Table 5

(hereinafter referred to as "Compound group SX5").

The Present compound represented by formula (I-C), formula (I-D), formula (I-E), formula (I-F), formula (I-G), formula (I-H), formula (I-I), or formula (I-J), wherein $A^1$ represents a CH;

n represents 0;

$R^{3a}$, $R^{3b}$, and $R^{3c}$ represent each a hydrogen atom; and $R^1$ and $R^2$ represent any one combination indicated in Table 1 to Table 5

(hereinafter referred to as "Compound group SX6").

TABLE 1

| $R^1$ | $R^2$ |
| --- | --- |
| $CF_3$ | $CH_2CH_3$ |
| $CH_2CF_2H$ | $CH_2CH_3$ |
| $CF_2CH_3$ | $CH_2CH_3$ |
| $CH_2CF_3$ | $CH_2CH_3$ |
| $CH_2CCl_3$ | $CH_2CH_3$ |
| $CF_2CF_2H$ | $CH_2CH_3$ |
| $CF_2CClFH$ | $CH_2CH_3$ |
| $CH_2CH_2CF_3$ | $CH_2CH_3$ |
| $CH_2CF_2CF_2H$ | $CH_2CH_3$ |
| $CH_2CF_2CF_3$ | $CH_2CH_3$ |
| $CF_2CBrF_2$ | $CH_2CH_3$ |
| $CF_2CFHCF_3$ | $CH_2CH_3$ |
| $CH_2CF_2CH_3$ | $CH_2CH_3$ |
| $CH(CH_3)CF_3$ | $CH_2CH_3$ |
| $C(CH_3)_2CF_3$ | $CH_2CH_3$ |
| $CH(CF_3)CH(CH_3)_2$ | $CH_2CH_3$ |
| $CH(CF_3)_2$ | $CH_2CH_3$ |
| $CH(CF_3)CH_2CH_3$ | $CH_2CH_3$ |
| $CH_2CCl_2CF_3$ | $CH_2CH_3$ |
| $CH(CH_3)CF_2CF_3$ | $CH_2CH_3$ |
| $CH(CH_2CH_3)CF_2CF_3$ | $CH_2CH_3$ |
| $CH_2C(CF_3)_2CH_3$ | $CH_2CH_3$ |
| $CH_2CF_2CFHCF_3$ | $CH_2CH_3$ |
| $CH_2CF_2CF_2CF_3$ | $CH_2CH_3$ |

TABLE 1-continued

| R¹ | R² |
|---|---|
| CH₂CH₂CF₂CBrF₂ | CH₂CH₃ |
| CH(CH₃)CF₂CFHCF₃ | CH₂CH₃ |

TABLE 2

| R¹ | R² |
|---|---|
| CH₂CH=CHCF₃ | CH₂CH₃ |
| CH₂(CF₂)₃CF₃ | CH₂CH₃ |
| CH₂(CF₂)₄CF₃ | CH₂CH₃ |
| CH₂CH₂(CF₂)₃CF₃ | CH₂CH₃ |
| CH₂CH₂CF₂CF₂CF(CF₃)₂ | CH₂CH₃ |
| CH₂(CF₂)₃CF₂H | CH₂CH₃ |
| CH₂(CF₂)₅CF₂H | CH₂CH₃ |
| CH₂CH₂CH₂(CF₂)₃CF₃ | CH₂CH₃ |
| CH₂(CH₂)₅CF₂CF₃ | CH₂CH₃ |
| CH₂CH₂CH₂(CF₂)₅CF₃ | CH₂CH₃ |
| CH₂(CH₂)₄CH₂(CF₂)₃CF₃ | CH₂CH₃ |
| CH₂CH₂(CF₂)₅CF₃ | CH₂CH₃ |
| CH₂(CH₂)₄CH₂CF(CF₃)₂ | CH₂CH₃ |
| CF₂CFHOCF₃ | CH₂CH₃ |
| CH₂CF₂CH₂OCH₃ | CH₂CH₃ |
| CH₂CF₂CH₂OCH₂CF₃ | CH₂CH₃ |
| CH₂CF₂CH₂F | CH₂CH₃ |
| CH₂CF₂CH₂Cl | CH₂CH₃ |
| CH₂CF₂CH₂Br | CH₂CH₃ |
| CH₂(CF₂)₂CH₂OCH₃ | CH₂CH₃ |
| CH₂(CF₂)₂CH₂OCH₂CF₃ | CH₂CH₃ |
| CH₂(CF₂)₂CH₂F | CH₂CH₃ |
| CH₂(CF₂)₂CH₂Cl | CH₂CH₃ |
| CH₂(CF₂)₂CH₂Br | CH₂CH₃ |
| CH₂(CF₂)₃CH₂OCH₃ | CH₂CH₃ |

TABLE 3

| R¹ | R² |
|---|---|
| CH₂(CF₂)₃CH₂OCH₂CF₃ | CH₂CH₃ |
| CH₂(CF₂)₃CH₂F | CH₂CH₃ |
| CH₂(CF₂)₃CH₂Cl | CH₂CH₃ |
| CH₂(CF₂)₃CH₂Br | CH₂CH₃ |
| CH₂(CF₂)₄CH₂OCH₃ | CH₂CH₃ |
| CH₂(CF₂)₄CH₂OCH₂CF₃ | CH₂CH₃ |
| CH₂(CF₂)₄CH₂F | CH₂CH₃ |
| CH₂(CF₂)₄CH₂Cl | CH₂CH₃ |
| CH₂(CF₂)₄CH₂Br | CH₂CH₃ |
| CF₂CFHOCF₂CF₃ | CH₂CH₃ |
| CF₂CFHOCF₂CF₂CF₃ | CH₂CH₃ |
| CH₂CF(CF₃)OCF₂CF₂CF₃ | CH₂CH₃ |
| CH₂CH₂OCH₂CF₃ | CH₂CH₃ |

TABLE 4

| R¹ | R² |
|---|---|
| 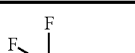 | CH₂CH₃ |

TABLE 4-continued

| R¹ | R² |
|---|---|
| 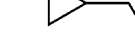 | CH₂CH₃ |

TABLE 5

| R¹ | R² |
|---|---|
| CH₂CF₂CH₂SCH₃ | CH₂CH₃ |
| CH₂CF₂CH₂S(O)CH₃ | CH₂CH₃ |
| CH₂CF₂CH₂S(O)₂CH₃ | CH₂CH₃ |
| CH₂CF₂CH₂SCH₂CF₃ | CH₂CH₃ |
| CH₂CF₂CH₂S(O)CH₂CF₃ | CH₂CH₃ |
| CH₂CF₂CH₂S(O)₂CH₂CF₃ | CH₂CH₃ |
| CH₂CF₂CH₂SCF₃ | CH₂CH₃ |
| CH₂CF₂CH₂S(O)CF₃ | CH₂CH₃ |
| CH₂CF₂CH₂S(O)₂CF₃ | CH₂CH₃ |
| CH₂(CF₂)₂CH₂SCF₃ | CH₂CH₃ |
| CH₂(CF₂)₂CH₂S(O)CF₃ | CH₂CH₃ |
| CH₂(CF₂)₂CH₂S(O)₂CF₃ | CH₂CH₃ |
| CH₂(CF₂)₃CH₂SCF₃ | CH₂CH₃ |
| CH₂(CF₂)₃CH₂S(O)CF₃ | CH₂CH₃ |
| CH₂(CF₂)₃CH₂S(O)₂CF₃ | CH₂CH₃ |
| CH₂(CF₂)₄CH₂SCF₃ | CH₂CH₃ |
| CH₂(CF₂)₄CH₂S(O)CF₃ | CH₂CH₃ |
| CH₂(CF₂)₄CH₂S(O)₂CF₃ | CH₂CH₃ |
| CH₂CH₂SCH₂CF₃ | CH₂CH₃ |
| CH₂CH₂S(O)CH₂CF₃ | CH₂CH₃ |
| CH₂CH₂S(O)₂CH₂CF₃ | CH₂CH₃ |
| CH₂CH₂SCF₃ | CH₂CH₃ |
| CH₂CH₂S(O)CF₃ | CH₂CH₃ |
| CH₂CH₂S(O)₂CF₃ | CH₂CH₃ |

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a trifluoromethyl group;
$R^2$ represents an ethyl group; and
$R^{3a}$, $R^{3b}$, and $R^{3c}$ represent any one combination indicated in Table 6 to Table 16
(hereinafter referred to as "Compound group SX7").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a trifluoromethyl group;
$R^2$ represents an ethyl group; and
$R^{3a}$, $R^{3b}$, and $R^{3c}$ represent any one combination indicated in Table 6 to Table 16
(hereinafter referred to as "Compound group SX8").

TABLE 6

| $R^{3a}$ | $R^{3b}$ | $R^{3c}$ |
|---|---|---|
| H | $CH_2CH=CH_2$ | H |
| $OCH_3$ | H | H |
| H | $OCH_3$ | H |
| H | H | $OCH_3$ |
| $OCH_2CH_3$ | H | H |
| H | $OCH_2CH_3$ | H |
| H | H | $OCH_2CH_3$ |
| H | $OCF_3$ | H |
| H | $SCF_3$ | H |
| H | $S(O)CF_3$ | H |
| H | $S(O)_2CF_3$ | H |
| Cl | H | H |
| H | Cl | H |
| H | H | Cl |
| $CF_3$ | H | H |
| $CF_2CF_3$ | H | H |
| $CF_2CF_2CF_3$ | H | H |
| $CF(CF_3)_2$ | H | H |
| H | $CF_3$ | H |
| H | $CF_2CF_3$ | H |
| H | $CF_2CF_2CF_3$ | H |
| H | $CF(CF_3)_2$ | H |
| H | H | $CF_3$ |
| H | H | $CF_2CF_3$ |
| H | H | $CF_2CF_2CF_3$ |
| H | H | $CF(CF_3)_2$ |

TABLE 7

| $R^{3a}$ | $R^{3b}$ | $R^{3c}$ |
|---|---|---|
| $NH_2$ | H | H |
| $NHCH_3$ | H | H |
| $N(CH_3)_2$ | H | H |
| $NHCH_2CF_3$ | H | H |
| H | $NH_2$ | H |
| H | $NHCH_3$ | H |
| H | $N(CH_3)_2$ | H |
| H | $NHCH_2CF_3$ | H |
| H | H | $NH_2$ |
| H | H | $NHCH_3$ |
| H | H | $N(CH_3)_2$ |
| H | H | $NHCH_2CF_3$ |
| H | $CF_3$ | $OCH_3$ |
| H | $CF_3$ | Cl |
| H | $CF_3$ | $NH_2$ |
| H | $CF_3$ | $NHCH_3$ |
| H | $CF_3$ | $N(CH_3)_2$ |
| H | $OCH_2CF_3$ | H |

TABLE 7-continued

| $R^{3a}$ | $R^{3b}$ | $R^{3c}$ |
|---|---|---|
| H | $OCH_2CF_2CF_3$ | H |
| H | $OCH_2CF_2CF_2H$ | H |
| H | $OCH_2CF_2CFHCF_3$ | H |
| H | $OCF_2CF_2CF_2FC_3$ | H |
| H | $OCH_2CH_2CH_3$ | H |
| H | $OCH(CH_3)_2$ | H |
| H | $OC(CH_3)_3$ | H |
| H | $OC(CH_3)_2CF_3$ | H |

TABLE 8

| $R^{3a}$ | $R^{3b}$ | $R^{3c}$ |
|---|---|---|
| $NHC(O)CH_3$ | H | H |
| $NHNHC(O)CH_3$ | H | H |
| $NHC(O)OCH_3$ | H | H |
| $NHNHC(O)OCH_3$ | H | H |
| $NHC(O)N(CH_3)_2$ | H | H |
| $NHNHC(O)N(CH_3)_2$ | H | H |
| $N=CHN(CH_3)_2$ | H | H |
| $N=S(CH_3)_2$ | H | H |
| $N=S(O)(CH_3)_2$ | H | H |
| $C(O)OCH_3$ | H | H |
| $C(O)NH_2$ | H | H |
| $C(O)NHCH_3$ | H | H |

TABLE 9

| $R^{3a}$ | $R^{3b}$ | $R^{3c}$ |
|---|---|---|
| H | $NHC(O)CH_3$ | H |
| H | $NHNHC(O)CH_3$ | H |
| H | $NHC(O)OCH_3$ | H |
| H | $NHNHC(O)OCH_3$ | H |
| H | $NHC(O)N(CH_3)_2$ | H |
| H | $NHNHC(O)N(CH_3)_2$ | H |
| H | $N=CHN(CH_3)_2$ | H |
| H | $N=S(CH_3)_2$ | H |
| H | $N=S(O)(CH_3)_2$ | H |
| H | $C(O)OCH_3$ | H |
| H | $C(O)NH_2$ | H |
| H | $C(O)NHCH_3$ | H |

TABLE 10

| $R^{3a}$ | $R^{3b}$ | $R^{3c}$ |
|---|---|---|
| H | H | $NHC(O)CH_3$ |
| H | H | $NHNHC(O)CH_3$ |
| H | H | $NHC(O)OCH_3$ |
| H | H | $NHNHC(O)OCH_3$ |
| H | H | $NHC(O)N(CH_3)_2$ |
| H | H | $NHNHC(O)N(CH_3)_2$ |
| H | H | $N=CHN(CH_3)_2$ |
| H | H | $N=S(CH_3)_2$ |
| H | H | $N=S(O)(CH_3)_2$ |
| H | H | $C(O)OCH_3$ |
| H | H | $C(O)NH_2$ |
| H | H | $C(O)NHCH_3$ |
| H | H | (2-chlorothiazol-5-yl)methylamino group |
| H | (1,2,4-triazol-1-yl) | H |

TABLE 10-continued
| R³ᵃ | R³ᵇ | R³ᶜ |
|---|---|---|
| H | 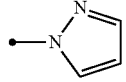 | H |
| H | 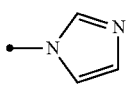 | H |
TABLE 11
| R³ᵃ | R³ᵇ | R³ᶜ |
|---|---|---|
| H | 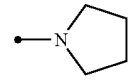 | H |
| H | 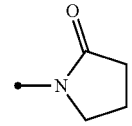 | H |
| H | 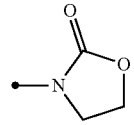 | H |
| H | 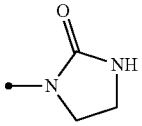 | H |
| H | 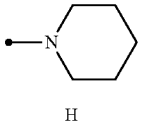 | H |
| H | H |  |
| H | H | 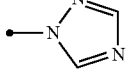 |
| H | H | 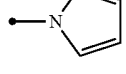 |
| H | H | 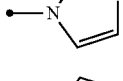 |
| H | H | 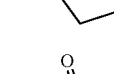 |
| H | H | 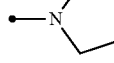 |
TABLE 11-continued
| R³ᵃ | R³ᵇ | R³ᶜ |
|---|---|---|
| H | H | 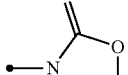 |
| H | H |  |
TABLE 12
| R³ᵃ | R³ᵇ | R³ᶜ |
|---|---|---|
| H | 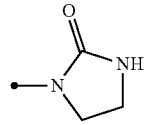 | H |
| H | 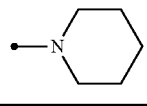 | H |
| H | 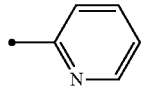 | H |
| H | 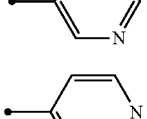 | H |
| H | 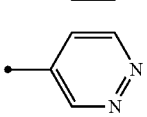 | H |
| H | 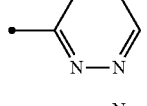 | H |
| H | 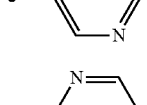 | H |
| H | 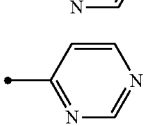 | H |
| H | H |  |
| H | H |  |
| H | H |  |

TABLE 12-continued
| R³ᵃ | R³ᵇ | R³ᶜ |
|---|---|---|
| H | H | 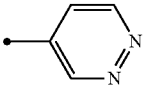 |
| H | H | 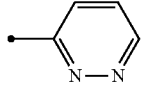 |
| H | H | 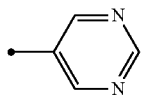 |
| H | H | 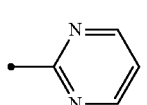 |
| H | H | 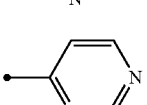 |
TABLE 13
| R³ᵃ | R³ᵇ | R³ᶜ |
|---|---|---|
| H | CF₃ | 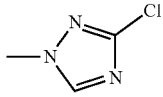 |
| H | CF₃ | 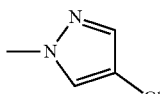 |
| H | 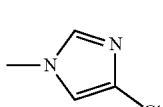 | H |
| H | 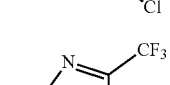 | H |
| H | 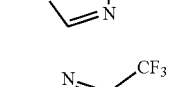 | H |
| H | 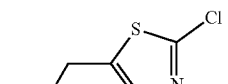 | H |
| H | 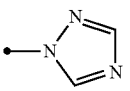 | H |
| H | 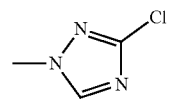 | H |
TABLE 14
| R³ᵃ | R³ᵇ | R³ᶜ |
|---|---|---|
| H | H | 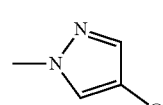 |
| H | H | 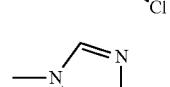 |
| H | H | 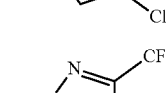 |
| H | H | 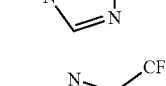 |
| H | H | 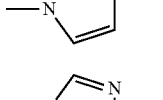 |
| H | H |  |
| H |  | H |
| H |  | H |
| H |  | H |
| H |  | H |
| H | H |  |
| H | H |  |
| H | H |  |
| H | H |  |

TABLE 15

| R³ᵃ | R³ᵇ | R³ᶜ |
|---|---|---|
| H | H | 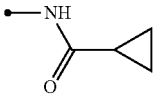 |
| H | H | 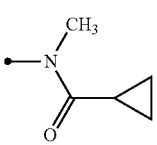 |
| H | H | 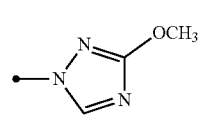 |
| H | H | 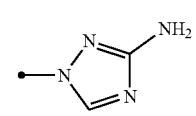 |
| H | H | 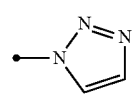 |
| H | H | 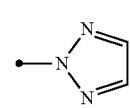 |
| H | H | 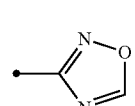 |
| H | H | 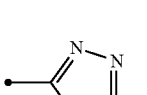 |
| H | 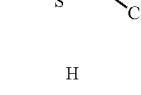 | H |
| H |  | H |
| H | 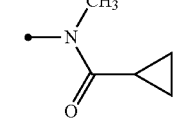 | H |
| H | 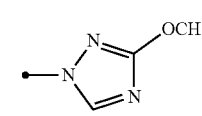 | H |

TABLE 15-continued

| R³ᵃ | R³ᵇ | R³ᶜ |
|---|---|---|
| H | 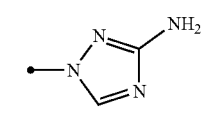 | H |
| H | 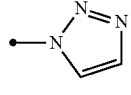 | H |

TABLE 16

| R³ᵃ | R³ᵇ | R³ᶜ |
|---|---|---|
| H | 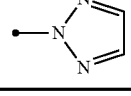 | H |
| H | 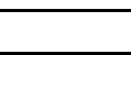 | H |
| H |  | H |
| H | 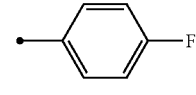 | H |
| H | 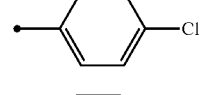 | H |
| H | 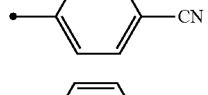 | H |
| H | 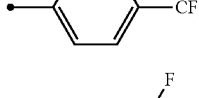 | H |
| H | 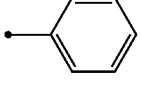 | H |
| H | 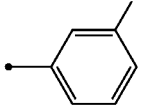 | H |
| H | 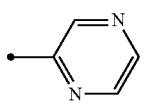 | H |

The Present compound represented by formula (I-C), formula (I-D), formula (I-E), formula (I-F), formula (I-G), formula (I-H), formula (I-I), or formula (I-J), wherein A¹ represents a nitrogen atom;

n represents 2;

R¹ represents a 2,2,2-trifluoroethyl group;

R² represents an ethyl group; and $R^{3a}$, $R^{3b}$, and $R^{3c}$ represent any one combination indicated in Table 6 to Table 16

(hereinafter referred to as "Compound group SX9").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a 2,2,2-trifluoroethyl group;
$R^2$ represents an ethyl group; and
$R^{3a}$, $R^{3b}$, and $R^{3c}$ represent any one combination indicated in Table 6 to Table 16

(hereinafter referred to as "Compound group SX10").

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a perfluoroethyl group;
$R^2$ represents an ethyl group; and
$R^{3a}$, $R^{3b}$, and $R^{3c}$ represent any one combination indicated in Table 6 to Table 16

(hereinafter referred to as "Compound group SX11").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a perfluoroethyl group;
$R^2$ represents an ethyl group; and
$R^{3a}$, $R^{3b}$, and $R^{3c}$ represent any one combination indicated in Table 6 to Table 16

(hereinafter referred to as "Compound group SX12").

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a 1,1,2,2-tetrafluoroethyl group;
$R^2$ represents an ethyl group; and
$R^{3a}$, $R^{3b}$, and $R^{3c}$ represent any one combination indicated in Table 6 to Table 16

(hereinafter referred to as "Compound group SX13").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a 1,1,2,2-tetrafluoroethyl group;
$R^2$ represents an ethyl group; and
$R^{3a}$, $R^{3b}$, and $R^{3c}$ represent any one combination indicated in Table 6 to Table 16

(hereinafter referred to as "Compound group SX14").

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a 1,1,2,3,3,3-hexafluoropropyl group;
$R^2$ represents an ethyl group; and
$R^{3a}$, $R^{3b}$, and $R^{3c}$ represent any one combination indicated in Table 6 to Table 16

(hereinafter referred to as "Compound group SX15").

The Present compound represented by formula (I-C), formula (I-D), formula (I-E), formula (I-F), formula (I-G), formula (I-H), formula (I-I), or formula (I-J), wherein
$A^1$ represents a CH; n represents 2;
$R^1$ represents a 1,1,2,3,3,3-hexafluoropropyl group;
$R^2$ represents an ethyl group; and
$R^{3a}$, $R^{3b}$, and $R^{3c}$ represent any one combination indicated in Table 6 to Table 16

(hereinafter referred to as "Compound group SX16").

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a perfluoropropyl group;
$R^2$ represents an ethyl group; and
$R^{3a}$, $R^{3b}$, and $R^{3c}$ represent any one combination indicated in Table 6 to Table 16

(hereinafter referred to as "Compound group SX17").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a perfluoropropyl group;
$R^2$ represents an ethyl group; and
$R^{3a}$, $R^{3b}$, and $R^{3c}$ represent any one combination indicated in Table 6 to Table 16

(hereinafter referred to as "Compound group SX18").

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a perfluoropropan-2-yl group;
$R^2$ represents an ethyl group; and
$R^{3a}$, $R^{3b}$, and $R^{3c}$ represent any one combination indicated in Table 6 to Table 16

(hereinafter referred to as "Compound group SX19").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a perfluoropropan-2-yl group;
$R^2$ represents an ethyl group; and
$R^{3a}$, $R^{3b}$, and $R^3$ represent any one combination indicated in Table 6 to Table 16

(hereinafter referred to as "Compound group SX20").

The Present compound represented by formula (I-C), formula (I-D), formula (I-E), formula (I-F), formula (I-G), formula (I-H), formula (I-I), or formula (I-J), wherein
$A^1$ represents a nitrogen atom;
n represents 2;
$R^1$ represents a 2,2,3,4,4,4-hexafluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX21").

The Present compound represented by formula (I-C), formula (I-D), formula (I-E), formula (I-F), formula (I-G), formula (I-H), formula (I-I), or formula (I-J), wherein
$A^1$ represents a CH;
n represents 2;
$R^1$ represents a 2,2,3,4,4,4-hexafluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX22").

The Present compound represented by formula (I-C), formula (I-D), formula (I-E), formula (I-F), formula (I-G), formula (I-H), formula (I-I), or formula (I-J), wherein $A^1$ represents a nitrogen atom;

n represents 2;

$R^1$ represents a 2,2,3,3,4,4,4-heptafluorobutyl group;

$R^2$ represents an ethyl group; and $R^{3a}$, $R^{3b}$, and $R^{3c}$ represent any one combination indicated in Table 6 to Table 16

(hereinafter referred to as "Compound group SX23").

The Present compound represented by formula (I-C), formula (I-D), formula (I-E), formula (I-F), formula (I-G), formula (I-H), formula (I-I), or formula (I-J), wherein $A^1$ represents a CH;

n represents 2;

$R^1$ represents a 2,2,3,3,4,4,4-heptafluorobutyl group;

$R^2$ represents an ethyl group; and $R^{3a}$, $R^{3b}$, and $R^{3c}$ represent any one combination indicated in Table 6 to Table 16

(hereinafter referred to as "Compound group SX24").

The Present compound represented by formula (I-C), formula (I-D), formula (I-E), formula (I-F), formula (I-G), formula (I-H), formula (I-I), or formula (I-J), wherein $A^1$ represents a nitrogen atom;

n represents 2;

$R^1$ represents a perfluorobutyl group;

$R^2$ represents an ethyl group; and $R^{3a}$, $R^{3b}$, and $R^{3c}$ represent any one combination indicated in Table 6 to Table 16

(hereinafter referred to as "Compound group SX25").

The Present compound represented by formula (I-C), formula (I-D), formula (I-E), formula (I-F), formula (I-G), formula (I-H), formula (I-I), or formula (I-J), wherein $A^1$ represents a CH;

n represents 2;

$R^1$ represents a perfluorobutyl group;

$R^2$ represents an ethyl group; and $R^{3a}$, $R^{3b}$, and $R^{3c}$ represent any one combination indicated in Table 6 to Table 16

(hereinafter referred to as "Compound group SX26").

The Present compound represented by formula (I-C), formula (I-D), formula (I-E), formula (I-F), formula (I-G), formula (I-H), formula (I-I), or formula (I-J), wherein $A^1$ represents a nitrogen atom;

n represents 2;

$R^1$ represents a perfluoropentyl group;

$R^2$ represents an ethyl group; and $R^{3a}$, $R^{3b}$, and $R^{3c}$ represent any one combination indicated in Table 6 to Table 16

(hereinafter referred to as "Compound group SX27").

The Present compound represented by formula (I-C), formula (I-D), formula (I-E), formula (I-F), formula (I-G), formula (I-H), formula (I-I), or formula (I-J), wherein $A^1$ represents a CH;

n represents 2;

$R^1$ represents a perfluoropentyl group;

$R^2$ represents an ethyl group; and $R^{3a}$, $R^{3b}$, and $R^{3c}$ represent any one combination indicated in Table 6 to Table 16

(hereinafter referred to as "Compound group SX28").

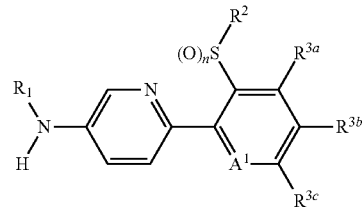

(II-A)

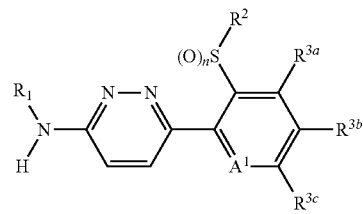

(II-B)

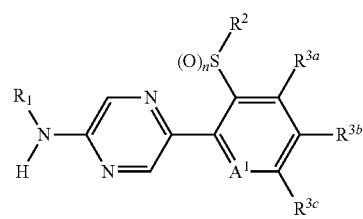

(II-C)

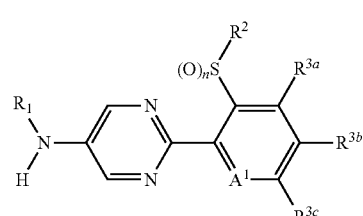

(II-D)

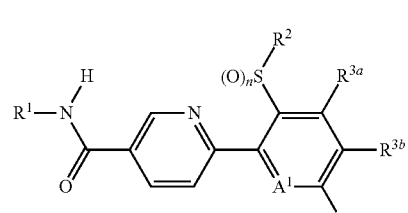

(II-E)

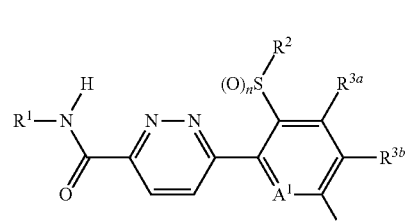

(II-F)

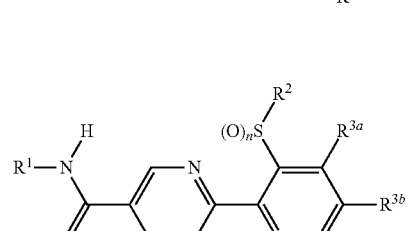

(II-G)

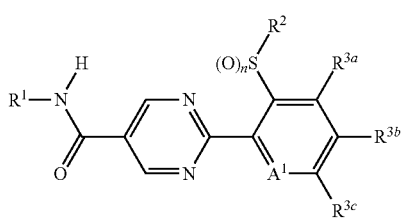 (II-H)
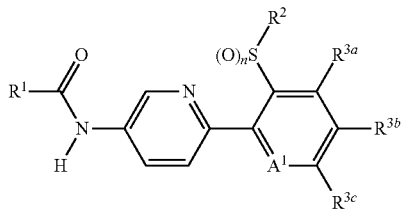 (II-I)
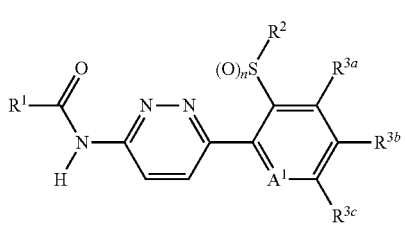 (II-J)
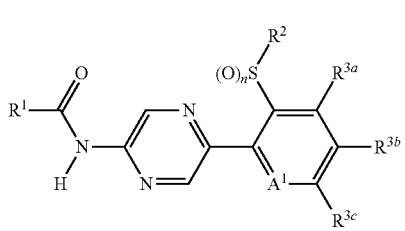 (II-K)
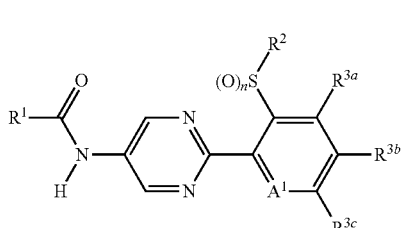 (II-L)
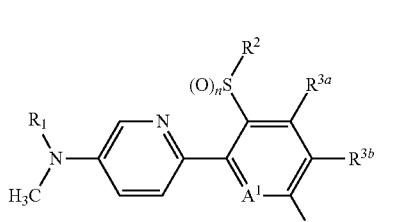 (II-M)
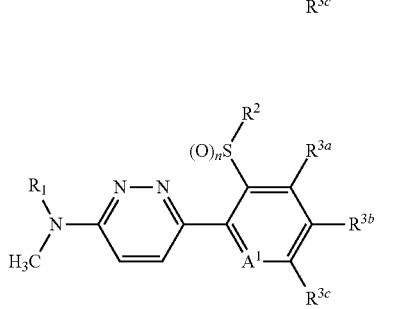 (II-N)
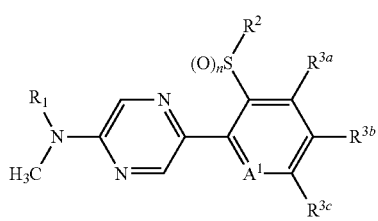 (II-O)
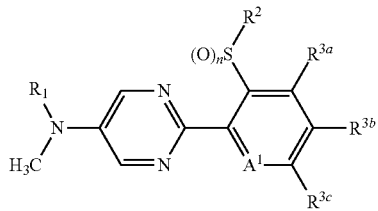 (II-P)
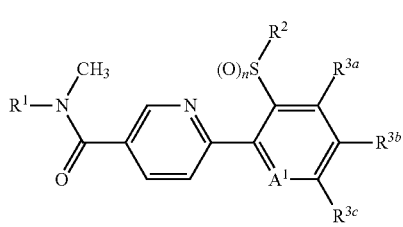 (II-Q)
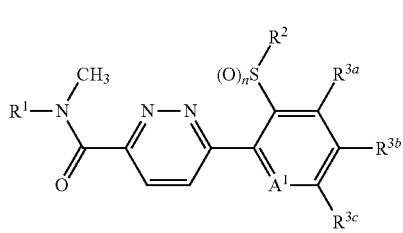 (II-R)
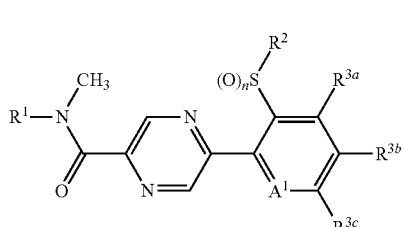 (II-S)
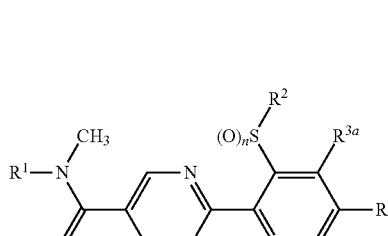 (II-T)
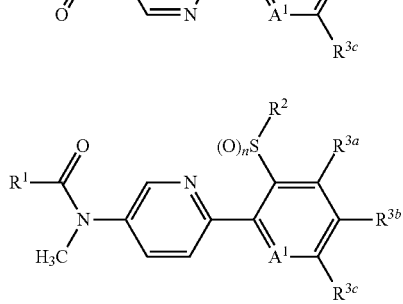 (II-U)

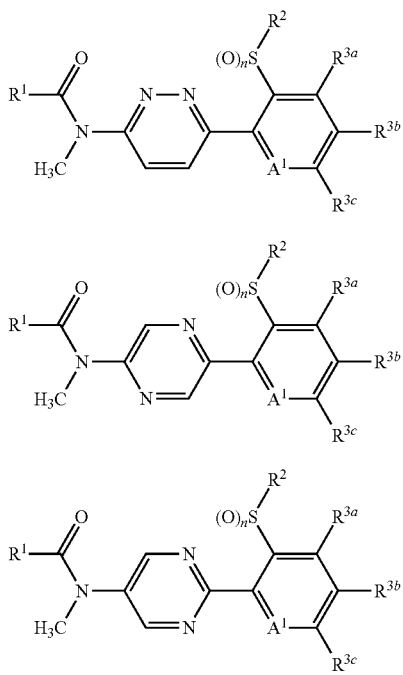

(II-V)

(II-W)

(II-X)

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein A$^1$ represents a nitrogen atom;
n represents 2;
R$^{3a}$, R$^{3b}$, and R$^{3c}$ represent each a hydrogen atom; and
R$^1$ and R$^2$ represent any one combination indicated in Table 1 to Table 5, or Table 17
(hereinafter referred to as "Compound group SX29").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein A$^1$ represents a CH;
n represents 2;
R$^{3a}$, R$^{3b}$, and R$^{3c}$ represent each a hydrogen atom; and
R$^1$ and R$^2$ represent any one combination indicated in Table 1 to Table 5, or Table 17
(hereinafter referred to as "Compound group SX30").

TABLE 17

| R$^1$ | R$^2$ |
|---|---|
| CH$_2$CF$_2$H | CH$_2$CH$_3$ |
| CH$_2$CF$_3$ | CH$_2$CH$_3$ |
| CH$_2$CCl$_3$ | CH$_2$CH$_3$ |
| CH$_2$CH$_2$CF$_3$ | CH$_2$CH$_3$ |
| CH$_2$CF$_2$CF$_2$H | CH$_2$CH$_3$ |
| CH$_2$CF$_2$CF$_3$ | CH$_2$CH$_3$ |

TABLE 17-continued

| R$^1$ | R$^2$ |
|---|---|
| CF$_2$CFHCF$_3$ | CH$_2$CH$_3$ |
| CH$_2$CF$_2$CH$_3$ | CH$_2$CH$_3$ |
| CH(CH$_3$)CF$_3$ | CH$_2$CH$_3$ |
| C(CH$_3$)$_2$CF$_3$ | CH$_2$CH$_3$ |
| CH(CF$_3$)$_2$ | CH$_2$CH$_3$ |
| CH$_2$CCl$_2$CF$_3$ | CH$_2$CH$_3$ |
| CH(CH$_3$)CF$_2$CF$_3$ | CH$_2$CH$_3$ |
| CH(CH$_2$CH$_3$)CF$_2$CF$_3$ | CH$_2$CH$_3$ |
| CH$_2$C(CF$_3$)$_2$CH$_3$ | CH$_2$CH$_3$ |
| CH$_2$CF$_2$CFHCF$_3$ | CH$_2$CH$_3$ |
| CH$_2$(CF$_2$)$_2$CF$_3$ | CH$_2$CH$_3$ |
| CH$_2$CH$_2$CF$_2$CBrF$_2$ | CH$_2$CH$_3$ |
| CH(CH$_3$)CF$_2$CFHCF$_3$ | CH$_2$CH$_3$ |

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein A$^1$ represents a nitrogen atom;
n represents 2;
R$^1$ represents a 2,2,2-trifluoroethyl group;
R$^2$ represents an ethyl group; and
R$^{3a}$, R$^{3b}$, and R$^{3c}$ represent any one combination indicated in Table 6 to Table 16
(hereinafter referred to as "Compound group SX31").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein A$^1$ represents a CH;
n represents 2;
R$^1$ represents a 2,2,2-trifluoroethyl group;
R$^2$ represents an ethyl group; and
R$^{3a}$, R$^{3b}$, and R$^{3c}$ represent any one combination indicated in Table 6 to Table 16
(hereinafter referred to as "Compound group SX32").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein A$^1$ represents a nitrogen atom;
n represents 2;
R$^1$ represents a 1,1,2,3,3,3-hexafluoropropyl group;
R$^2$ represents an ethyl group; and
R$^{3a}$, R$^{3b}$, and R$^{3c}$ represent any one combination indicated in Table 6 to Table 16
(hereinafter referred to as "Compound group SX33").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein
 $A^1$ represents a CH;
 n represents 2;
 $R^1$ represents a 1,1,2,3,3,3-hexafluoropropyl group;
 $R^2$ represents an ethyl group; and
 $R^{3a}$, $R^{3b}$, and $R^{3c}$ represent any one combination indicated in Table 6 to Table 16
(hereinafter referred to as "Compound group SX34").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein
 $A^1$ represents a nitrogen atom;
 n represents 2;
 $R^1$ represents a 2,2,3,4,4,4-hexafluorobutyl group;
 $R^2$ represents an ethyl group; and
 $R^{3a}$, $R^{3b}$, and $R^{3c}$ represent any one combination indicated in Table 6 to Table 16
(hereinafter referred to as "Compound group SX35").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-0), formula (II-P), formula (II-Q), formula (II-R), formula (II-S), formula (II-T), formula (II-U), formula (II-V), formula (II-W), or formula (II-X), wherein
 $A^1$ represents a CH;
 n represents 2;
 $R^1$ represents a 2,2,3,4,4,4-hexafluorobutyl group;
 $R^2$ represents an ethyl group; and
 $R^{3a}$, $R^{3b}$, and $R^{3c}$ represent any one combination indicated in Table 6 to Table 16
(hereinafter referred to as "Compound group SX36").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein
 $A^1$ represents a nitrogen atom;
 n represents 2;
 $R^1$ represents a 2,2,3,3,4,4,4-heptafluorobutyl group;
 $R^2$ represents an ethyl group; and
 $R^{3a}$, $R^{3b}$, and $R^{3c}$ represent any one combination indicated in Table 6 to Table 16
(hereinafter referred to as "Compound group SX37").

The Present compound represented by formula (II-A), formula (II-B), formula (II-C), formula (II-D), formula (II-E), formula (II-F), formula (II-G), formula (II-H), formula (II-I), formula (II-J), formula (II-K), formula (II-L), formula (II-M), formula (II-N), formula (II-O), formula (II-P), formula (II-Q), formula (II-R), formula (II-S), formula (II-T), formula (II-U), formula (II-V), formula (II-W), or formula (II-X), wherein
 $A^1$ represents a CH;
 n represents 2;
 $R^1$ represents a 2,2,3,3,4,4,4-heptafluorobutyl group;
 $R^2$ represents an ethyl group; and
 $R^{3a}$, $R^{3b}$, and $R^{3c}$ represent any one combination indicated in Table 6 to Table 16
(hereinafter referred to as "Compound group SX38").

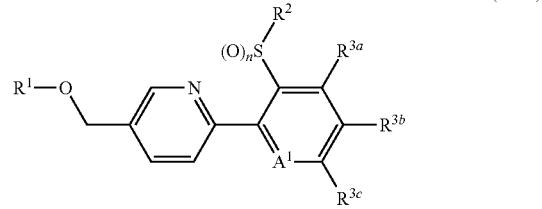
(III-A)

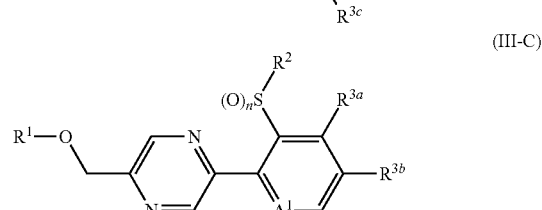
(III-B)

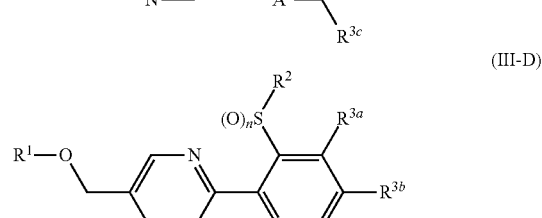
(III-C)

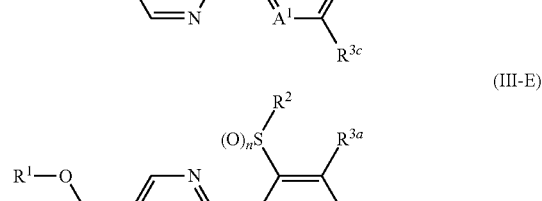
(III-D)

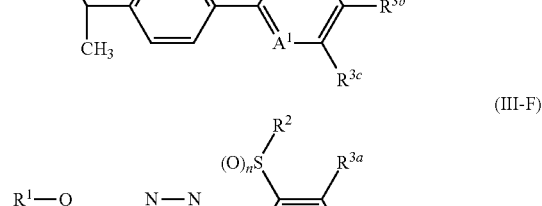
(III-E)

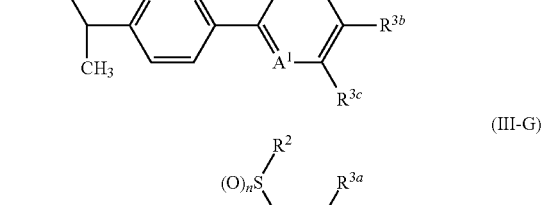
(III-F)

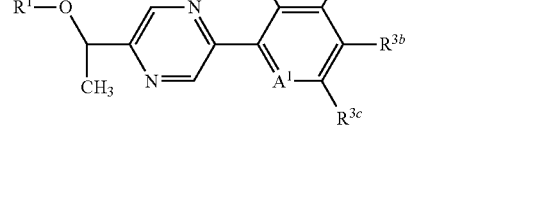
(III-G)

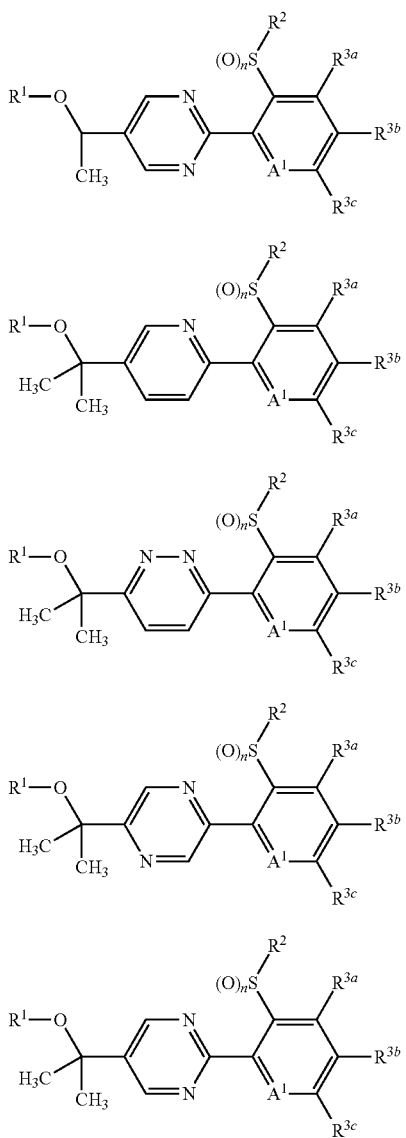

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a nitrogen atom;
n represents 2;
R$^{3a}$, R$^{3b}$, and R$^{3c}$ represent each a hydrogen atom; and
R$^1$ and R$^2$ represent any one combination indicated in Table 1 to Table 5
(hereinafter referred to as "Compound group SX39").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a nitrogen atom;
n represents 1;
R$^{3a}$, R$^{3b}$, and R$^{3c}$ represent each a hydrogen atom; and
R$^1$ and R$^2$ represent any one combination indicated in Table 1 to Table 5
(hereinafter referred to as "Compound group SX40").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a nitrogen atom;
n represents 0;
R$^{3a}$, R$^{3b}$, and R$^{3c}$ represent each a hydrogen atom; and
R$^1$ and R$^2$ represent any one combination indicated in Table 1 to Table 5
(hereinafter referred to as "Compound group SX41").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a CH;
n represents 2;
R$^{3a}$, R$^{3b}$, and R$^{3c}$ represent each a hydrogen atom; and
R$^1$ and R$^2$ represent any one combination indicated in Table 1 to Table 5
(hereinafter referred to as "Compound group SX42").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a CH;
n represents 1;
R$^{3a}$, R$^{3b}$, and R$^{3c}$ represent each a hydrogen atom; and
R$^1$ and R$^2$ represent any one combination indicated in Table 1 to Table 5
(hereinafter referred to as "Compound group SX43").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a CH;
n represents 0;
R$^{3a}$, R$^{3b}$, and R$^{3c}$ represent each a hydrogen atom; and
R$^1$ and R$^2$ represent any one combination indicated in Table 1 to Table 5
(hereinafter referred to as "Compound group SX44").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a nitrogen atom;
n represents 2;
R$^1$ represents a 2,2,2-trifluoroethyl group;
R$^2$ represents an ethyl group; and
R$^{3a}$, R$^{3b}$, and R$^{3c}$ represent any one combination indicated in Table 6 to Table 16
(hereinafter referred to as "Compound group SX45").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein A$^1$ represents a CH;
n represents 2;

R¹ represents a 2,2,2-trifluoroethyl group;
R² represents an ethyl group; and
$R^{3a}$, $R^{3b}$, and $R^{3c}$ represent any one combination indicated in Table 6 to Table 16
(hereinafter referred to as "Compound group SX46").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a nitrogen atom;
n represents 2;
R¹ represents a perfluoroethyl group;
R² represents an ethyl group; and
$R^{3a}$, $R^{3b}$, and $R^{3c}$ represent any one combination indicated in Table 6 to Table 16
(hereinafter referred to as "Compound group SX47").

The Present compound represented by formula (III-A), formula (III-B), formula (III-C), or formula (III-D), wherein
A¹ represents a CH;
n represents 2;
R¹ represents a perfluoroethyl group;
R² represents an ethyl group; and
$R^{3a}$, $R^{3b}$, and $R^{3c}$ represent any one combination indicated in Table 6 to Table 16
(hereinafter referred to as "Compound group SX48").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a nitrogen atom;
n represents 2;
R¹ represents a 1,1,2,2-tetrafluoroethyl group;
R² represents an ethyl group; and
$R^{3a}$, $R^{3b}$, and $R^{3C}$ represent any one combination indicated in Table 6 to Table 16
(hereinafter referred to as "Compound group SX49").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a CH;
n represents 2;
R¹ represents a 1,1,2,2-tetrafluoroethyl group;
R² represents an ethyl group; and
$R^{3a}$, $R^{3b}$, and $R^{3c}$ represent any one combination indicated in Table 6 to Table 16
(hereinafter referred to as "Compound group SX50").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a nitrogen atom;
n represents 2;
R¹ represents a 1,1,2,3,3,3-hexafluoropropyl group;
R² represents an ethyl group; and
$R^{3a}$, $R^{3b}$, and $R^{3c}$ represent any one combination indicated in Table 6 to Table 16
(hereinafter referred to as "Compound group SX51").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a CH;
n represents 2;
R¹ represents a 1,1,2,3,3,3-hexafluoropropyl group;
R² represents an ethyl group; and
$R^{3a}$, $R^{3b}$, and $R^{3c}$ represent any one combination indicated in Table 6 to Table 16
(hereinafter referred to as "Compound group SX52").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a nitrogen atom;
n represents 2;
R¹ represents a perfluoropropyl group;
R² represents an ethyl group; and
$R^{3a}$, $R^{3b}$, and $R^{3c}$ represent any one combination indicated in Table 6 to Table 16
(hereinafter referred to as "Compound group SX53").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a CH;
n represents 2;
R¹ represents a perfluoropropyl group;
R² represents an ethyl group; and
$R^{3a}$, $R^{3b}$, and $R^{3c}$ represent any one combination indicated in Table 6 to Table 16
(hereinafter referred to as "Compound group SX54").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a nitrogen atom;
n represents 2;
R¹ represents a perfluoropropan-2-yl group;
R² represents an ethyl group; and
$R^{3a}$, $R^{3b}$, and $R^{3c}$ represent any one combination indicated in Table 6 to Table 16
(hereinafter referred to as "Compound group SX55").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a CH;
n represents 2;
R¹ represents a perfluoropropan-2-yl group;
R² represents an ethyl group; and
$R^{3a}$, $R^{3b}$, and $R^{3C}$ represent any one combination indicated in Table 6 to Table 16
(hereinafter referred to as "Compound group SX56").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein
A¹ represents a nitrogen atom;
n represents 2;
R¹ represents a 2,2,3,4,4,4-hexafluorobutyl group;
R² represents an ethyl group; and
$R^{3a}$, $R^{3b}$, and $R^{3c}$ represent any one combination indicated in Table 6 to Table 16
(hereinafter referred to as "Compound group SX57").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a CH;
n represents 2;
$R^1$ represents a 2,2,3,4,4,4-hexafluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX58").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a nitrogen atom;
n represents 2;
$R^1$ represents a 2,2,3,3,4,4,4-heptafluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX59").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a CH;
n represents 2;
$R^1$ represents a 2,2,3,3,4,4,4-heptafluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX60").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a nitrogen atom;
n represents 2;
$R^1$ represents a perfluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX61").

The Present compound represented by formula (Ill-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a CH;
n represents 2;
$R^1$ represents a perfluorobutyl group;
$R^2$ represents an ethyl group; and
$R^{3a}$, $R^{3b}$, and $R^{3c}$ represent any one combination indicated in Table 6 to Table 16

(hereinafter referred to as "Compound group SX62").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a nitrogen atom;
n represents 2;
$R^1$ represents a perfluoropentyl group;
$R^2$ represents an ethyl group; and
$R^{3a}$, $R^{3b}$, and $R^{3c}$ represent any one combination indicated in Table 6 to Table 16

(hereinafter referred to as "Compound group SX63").

The Present compound represented by formula (III-A), formula (III-B), formula (III-C), formula (III-D), formula (III-E), formula (III-F), formula (III-G), formula (III-H), formula (III-I), formula (III-J), formula (III-K), or formula (III-L), wherein $A^1$ represents a CH;
n represents 2;
$R^1$ represents a perfluoropentyl group;
$R^2$ represents an ethyl group; and
$R^{3a}$, $R^{3b}$, and $R^{3c}$ represent any one combination indicated in Table 6 to Table 16

(hereinafter referred to as "Compound group SX64").

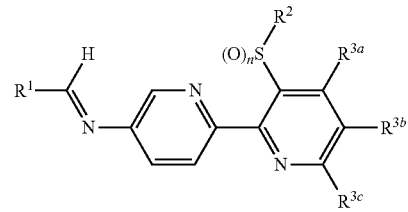

(IV-A)

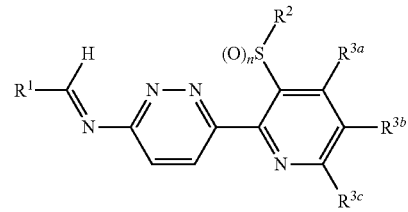

(IV-B)

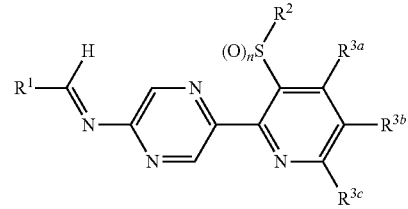

(IV-C)

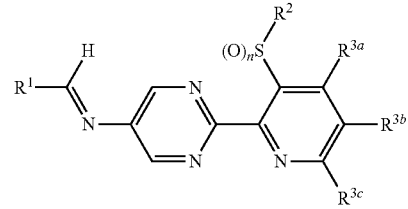

(IV-D)

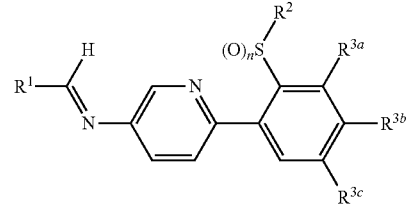

(IV-E)

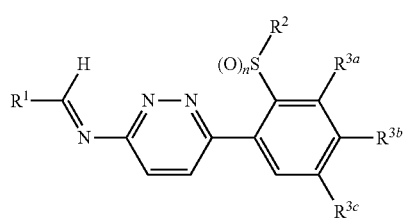
(IV-F)
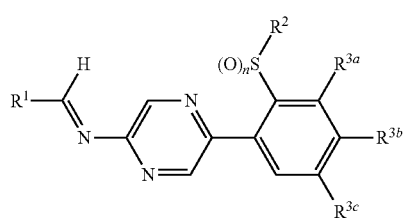
(IV-G)
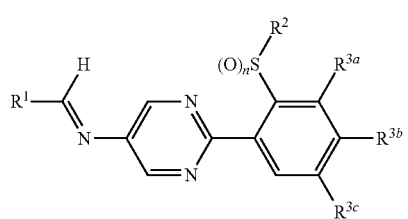
(IV-H)
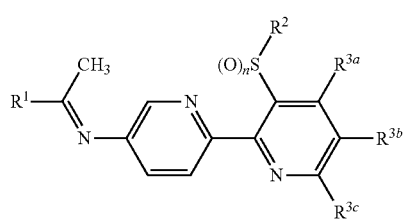
(IV-I)
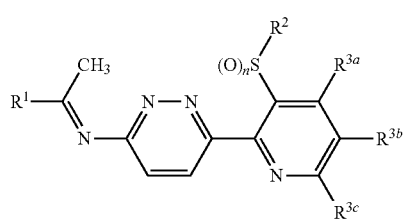
(IV-J)
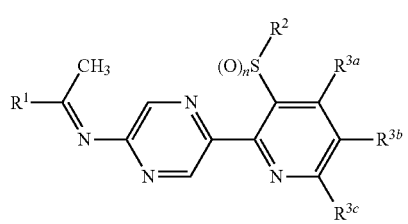
(IV-K)
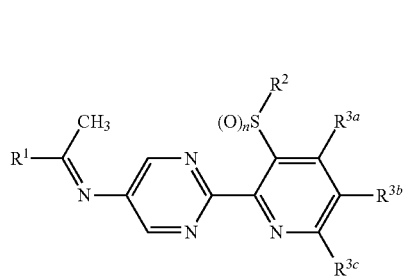
(IV-L)
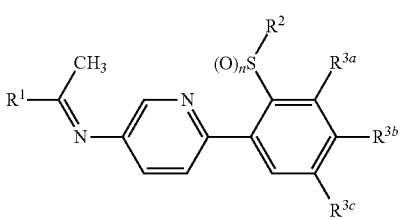
(IV-M)
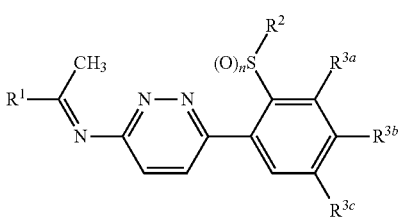
(IV-N)
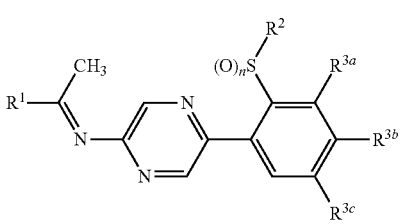
(IV-O)
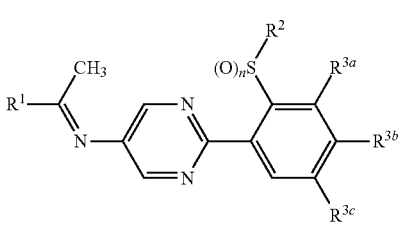
(IV-P)
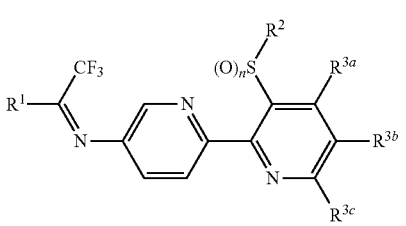
(IV-Q)
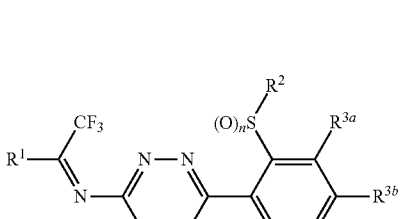
(IV-R)
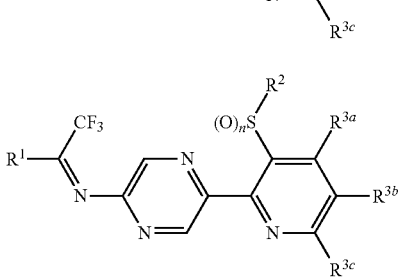
(IV-S)

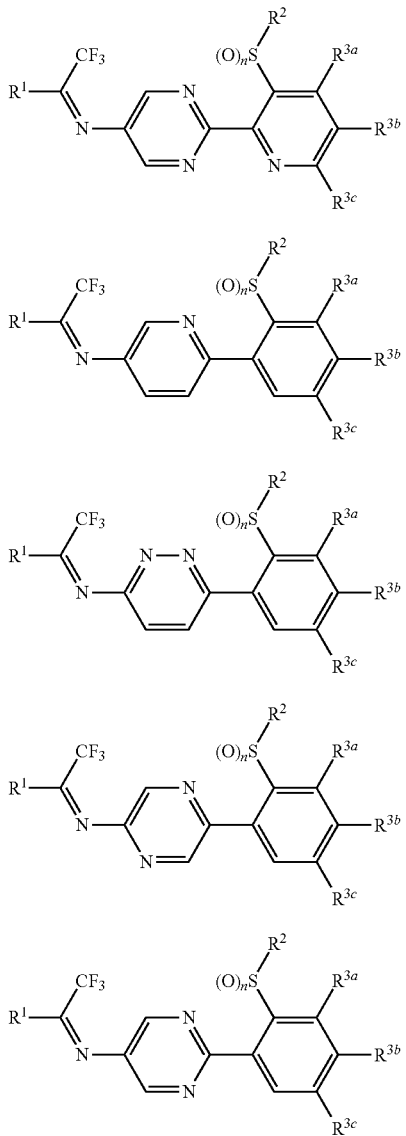

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
$A^1$ represents a nitrogen atom;
n represents 2;
$R^{3a}$, $R^{3b}$, and $R^{3c}$ represent each a hydrogen atom; and
$R^1$ and $R^2$ represent any one combination indicated in Table 1 to Table 2
(hereinafter referred to as "Compound group SX65").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
$A^1$ represents a nitrogen atom;
n represents 1;
$R^{3a}$, $R^{3b}$, and $R^{3c}$ represent each a hydrogen atom; and
$R^1$ and $R^2$ represent any one combination indicated in Table 1 to Table 2
(hereinafter referred to as "Compound group SX66").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
$A^1$ represents a nitrogen atom;
n represents 0;
$R^{3a}$, $R^{3b}$, and $R^{3c}$ represent each a hydrogen atom; and
$R^1$ and $R^2$ represent any one combination indicated in Table 1 to Table 2
(hereinafter referred to as "Compound group SX67").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
$A^1$ represents a CH;
n represents 2;
$R^{3a}$, $R^{3b}$, and $R^{3c}$ represent each a hydrogen atom; and
$R^1$ and $R^2$ represent any one combination indicated in Table 1 to Table 2
(hereinafter referred to as "Compound group SX68").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
$A^1$ represents a CH;
n represents 1;
$R^{3a}$, $R^{3b}$, and $R^{3c}$ represent each a hydrogen atom; and
$R^1$ and $R^2$ represent any one combination indicated in Table 1 to Table 2
(hereinafter referred to as "Compound group SX69").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
$A^1$ represents a CH;
n represents 0;
$R^{3a}$, $R^{3b}$, and $R^{3c}$ represent each a hydrogen atom; and
$R^1$ and $R^2$ represent any one combination indicated in Table 1 to Table 2
(hereinafter referred to as "Compound group SX70").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a nitrogen atom;
n represents 2;
$R^1$ represents a 2,2,2-trifluoroethyl group;
$R^2$ represents an ethyl group; and
$R^{3a}$, $R^{3b}$, and $R^{3c}$ represent any one combination indicated in Table 6 to Table 16
(hereinafter referred to as "Compound group SX71").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a CH;
n represents 2;
$R^1$ represents a 2,2,2-trifluoroethyl group;
$R^2$ represents an ethyl group; and
$R^{3a}$, $R^{3b}$, and $R^{3c}$ represent any one combination indicated in Table 6 to Table 16
(hereinafter referred to as "Compound group SX72").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a nitrogen atom;
n represents 2; $R^1$ represents a perfluoroethyl group;
$R^2$ represents an ethyl group; and
$R^{3a}$, $R^{3b}$, and $R^{3c}$ represent any one combination indicated in Table 6 to Table 16
(hereinafter referred to as "Compound group SX73").

The Present compound represented by formula (IV-A), formula (IV-B), formula (IV-C), or formula (IV-D), wherein $A^1$ represents a CH;
n represents 2;
$R^1$ represents a perfluoroethyl group;
$R^2$ represents an ethyl group; and
$R^{3a}$, $R^{3b}$, and $R^{3c}$ represent any one combination indicated in Table 6 to Table 16
(hereinafter referred to as "Compound group SX74").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a nitrogen atom;
n represents 2;
$R^1$ represents a 1,1,2,2-tetrafluoroethyl group;
$R^2$ represents an ethyl group; and
$R^{3a}$, $R^{3b}$, and $R^{3c}$ represent any one combination indicated in Table 6 to Table 16
(hereinafter referred to as "Compound group SX75").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a CH;
n represents 2;
$R^1$ represents a 1,1,2,2-tetrafluoroethyl group;
$R^2$ represents an ethyl group; and
$R^{3a}$, $R^{3b}$, and $R^{3c}$ represent any one combination indicated in Table 6 to Table 16
(hereinafter referred to as "Compound group SX76").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a nitrogen atom;
n represents 2;
$R^1$ represents a 1,1,2,3,3,3-hexafluoropropyl group;
$R^2$ represents an ethyl group; and
$R^{3a}$, $R^{3b}$, and $R^{3c}$ represent any one combination indicated in Table 6 to Table 16
(hereinafter referred to as "Compound group SX77").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a CH;
n represents 2;
$R^1$ represents a 1,1,2,3,3,3-hexafluoropropyl group;
$R^2$ represents an ethyl group; and
$R^{3a}$, $R^{3b}$, and $R^{3c}$ represent any one combination indicated in Table 6 to Table 16
(hereinafter referred to as "Compound group SX78").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein $A^1$ represents a nitrogen atom;
n represents 2;
$R^1$ represents a perfluoropropyl group;
$R^2$ represents an ethyl group; and
$R^{3a}$, $R^{3b}$, and $R^{3c}$ represent any one combination indicated in Table 6 to Table 16
(hereinafter referred to as "Compound group SX79").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein A¹ represents a CH;
n represents 2;
R¹ represents a perfluoropropyl group;
R² represents an ethyl group; and
$R^{3a}$, $R^{3b}$, and $R^{3c}$ represent any one combination indicated in Table 6 to Table 16
(hereinafter referred to as "Compound group SX80").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a nitrogen atom;
n represents 2;
R¹ represents a perfluoropropan-2-yl group;
R² represents an ethyl group; and
$R^{3a}$, $R^{3b}$, and $R^{3c}$ represent any one combination indicated in Table 6 to Table 16
(hereinafter referred to as "Compound group SX81").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a CH;
n represents 2;
R¹ represents a perfluoropropan-2-yl group;
R² represents an ethyl group; and
$R^{3a}$, $R^{3b}$, and $R^{3c}$ represent any one combination indicated in Table 6 to Table 16
(hereinafter referred to as "Compound group SX82").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a nitrogen atom;
n represents 2;
R¹ represents a 2,2,3,3-tetrafluoropropyl group;
R² represents an ethyl group; and
$R^{3a}$, $R^{3b}$, and $R^{3c}$ represent any one combination indicated in Table 6 to Table 16
(hereinafter referred to as "Compound group SX91").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a CH;
n represents 2;
R¹ represents a 2,2,3,3-tetrafluoropropyl group;
R² represents an ethyl group; and
$R^{3a}$, $R^{3b}$, and $R^{3c}$ represent any one combination indicated in Table 6 to Table 16
(hereinafter referred to as "Compound group SX92").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a nitrogen atom;
n represents 2;
R¹ represents a 2,2,3,3,3-pentafluoropropyl group;
R² represents an ethyl group; and
$R^{3a}$, $R^{3b}$, and $R^{3c}$ represent any one combination indicated in Table 6 to Table 16
(hereinafter referred to as "Compound group SX93").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a CH;
n represents 2;
R¹ represents a 2,2,3,3,3-pentafluoropropyl group;
R² represents an ethyl group; and
$R^{3a}$, $R^{3b}$, and $R^{3c}$ represent any one combination indicated in Table 6 to Table 16
(hereinafter referred to as "Compound group SX94").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a nitrogen atom;
n represents 2;
R¹ represents a 2,2,3,4,4,4-hexafluorobutyl group;
R² represents an ethyl group; and
$R^{3a}$, $R^{3b}$, and $R^{3c}$ represent any one combination indicated in Table 6 to Table 16
(hereinafter referred to as "Compound group SX83").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
A¹ represents a CH;
n represents 2;
R¹ represents a 2,2,3,4,4,4-hexafluorobutyl group;
R² represents an ethyl group; and
$R^{3a}$, $R^{3b}$, and $R^{3c}$ represent any one combination indicated in Table 6 to Table 16
(hereinafter referred to as "Compound group SX84").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
  $A^1$ represents a nitrogen atom;
  n represents 2;
  $R^1$ represents a 2,2,3,3,4,4,4-heptafluorobutyl group;
  $R^2$ represents an ethyl group; and
  $R^{3a}$, $R^{3b}$, and $R^{3c}$ represent any one combination indicated in Table 6 to Table 16
(hereinafter referred to as "Compound group SX85").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
  $A^1$ represents a CH;
  n represents 2;
  $R^1$ represents a 2,2,3,3,4,4,4-heptafluorobutyl group;
  $R^2$ represents an ethyl group; and
  $R^{3a}$, $R^{3b}$, and $R^{3c}$ represent any one combination indicated in Table 6 to Table 16
(hereinafter referred to as "Compound group SX86").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
  $A^1$ represents a nitrogen atom;
  n represents 2;
  $R^1$ represents a perfluorobutyl group;
  $R^2$ represents an ethyl group; and
  $R^{3a}$, $R^{3b}$, and $R^{3c}$ represent any one combination indicated in Table 6 to Table 16
(hereinafter referred to as "Compound group SX87").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
  $A^1$ represents a CH;
  n represents 2;
  $R^1$ represents a perfluorobutyl group;
  $R^2$ represents an ethyl group; and
  $R^{3a}$, $R^{3b}$, and $R^{3c}$ represent any one combination indicated in Table 6 to Table 16
(hereinafter referred to as "Compound group SX88").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
  $A^1$ represents a nitrogen atom;
  n represents 2;
  $R^1$ represents a perfluoropentyl group;
  $R^2$ represents an ethyl group; and
  $R^{3a}$, $R^{3b}$, and $R^{3c}$ represent any one combination indicated in Table 6 to Table 16
(hereinafter referred to as "Compound group SX89").

The Present compound represented by formula (IV-A), formula (IV-B), formula (IV-C), formula (IV-D), formula (IV-E), formula (IV-F), formula (IV-G), formula (IV-H), formula (IV-I), formula (IV-J), formula (IV-K), formula (IV-L), formula (IV-M), formula (IV-N), formula (IV-O), formula (IV-P), formula (IV-Q), formula (IV-R), formula (IV-S), formula (IV-T), formula (IV-U), formula (IV-V), formula (IV-W), or formula (IV-X), wherein
  $A^1$ represents a CH;
  n represents 2;
  $R^1$ represents a perfluoropentyl group;
  $R^2$ represents an ethyl group; and
  $R^{3a}$, $R^{3b}$, and $R^{3c}$ represent any one combination indicated in Table 6 to Table 16
(hereinafter referred to as "Compound group SX90").

The Present compound may be mixed with or used in combination with the following one or more ingredients selected from the group consisting of Group (a), Group (b), Group (c), Group (d), and Group (e) (hereinafter referred to as "Present ingredient").

When the Present compound is mixed with or used in combination with the Present ingredient, they are used simultaneously, separately, or at time intervals with each other.

When the Present compound is used simultaneously with the Present ingredient, the Present compound and the Present ingredient may be contained in separate formulations or contained in one formulation.

One aspect of the present invention provides a composition comprising one or more ingredients selected from the group consisting of Group (a), Group (b), Group (c), Group (d), and Group (e) (i.e., Present ingredient), and the Present compound.

Group (a) is a group of insecticidal active ingredients, acaricidal active ingredients, and nematicidal active ingredients consisting of the following Subgroup a-1 to Subgroup a-10.
Subgroup a-1: Carbamate acetylcholinesterase (AChE) inhibitors
Subgroup a-2: Organophosphorus acetylcholinesterase (AChE) inhibitors
Subgroup a-3: GABAergic chloride channel blockers
Subgroup a-4: GABAergic chloride channel allosteric modulators
Subgroup a-5: Sodium channel modulators
Subgroup a-6: Nicotinic acetylcholine receptor (nAChR) competitive modulators
Subgroup a-7: Ryanodine receptor modulators
Subgroup a-8: Microbial materials
Subgroup a-9: Nematicidal active ingredients
Subgroup a-10: Other insecticidal active ingredients and acaricidal active ingredients
Group (b) is a group of fungicidal active ingredients consisting of the following Subgroup b-1 to Subgroup b-18.
Subgroup b-1: PA fungicides (Phenylamides)
Subgroup b-2: MBC fungicides (Methyl benzimidazole carbamates)
Subgroup b-3: Thiazole carboxamides
Subgroup b-4: SDHI (Succinate dehydrogenase inhibitors)
Subgroup b-5: QoI fungicides (Qo inhibitors)

Subgroup b-6: QiI fungicides (Qi inhibitors)
Subgroup b-7: Thiophenecarboxamides
Subgroup b-8: AP fungicides (Anilinopyrimidines)
Subgroup b-9: PP fungicides (Phenylpyrroles)
Subgroup b-10: AH fungicides (Aromatic hydrocarbons)
Subgroup b-11: DMI-fungicides (Demethylation inhibitors)
Subgroup b-12: CCA fungicides (Carboxylic acid amides)
Subgroup b-13: Piperidinyl thiazole isoxazolines
Subgroup b-14: Tetrazolyl oximes
Subgroup b-15: Dithiocarbamates
Subgroup b-16: Phthalimides
Subgroup b-17: Microbial fungicides
Subgroup b-18: Other fungicides Group (c) is a group of plant growth regulatory ingredients consisting of the following Subgroup c-1, Subgroup c-2, and Subgroup c-3.
Subgroup c-1: Plant growth regulatory ingredients
Subgroup c-2: Mycorrhizal fungi
Subgroup c-3: Root nodule bacteria Group (d) is a group of phytotoxicity-reducing ingredients.

Group (e) is a group of synergists.

A composition comprising said Present ingredient and the Present compound produces its effects depending on the contained amount or the content percentage of said Present ingredient or said Present compound in said composition. Thus, the use of said composition may be determined depending on the effect produced by said composition. Said composition may have one or more uses.

One aspect of said composition is an agrochemical composition.

Another aspect of said composition is a composition for controlling a harmful arthropod.

Still another aspect of said composition is an insecticidal, acaricidal, or nematicidal composition.

Still another aspect of said composition is a fungicidal composition.

Still another aspect of said composition is a plant growth regulatory composition.

Still another aspect of said composition is a phytotoxicity-reducing composition.

Hereinafter, examples of the combination of the Present ingredient and the Present compound are described. For example, "alanycarb+SX" indicates a combination of alanycarb and SX.

The abbreviation of "SX" indicates any one of the Present compound selected from the Compound groups SX1 to SX94. Also, all of the following Present ingredients are known ingredients, and obtainable from a commercially available formulation, or may be prepared by a known method. When the Present ingredient is a microorganism, it may be available from a bacterial authority depository. Further, the number in parentheses represents the CAS registration number.

Combinations of the Present ingredient in the above Subgroup a-1 and the Present compound:
alanycarb+SX, aldicarb+SX, bendiocarb+SX, benfuracarb+SX, butocarboxim+SX, butoxycarboxim+SX, carbaryl (NAC)+SX, carbofuran+SX, carbosulfan+SX, ethiofencarb+SX, fenobucarb (BPMC)+SX, formetanate+SX, furathiocarb+SX, isoprocarb (MIPC)+SX, methiocarb+SX, methomyl+SX, metolcarb+SX, oxamyl+SX, pirimicarb+SX, propoxur (PHC)+SX, thiodicarb+SX, thiofanox+SX, triazamate+SX, trimethacarb+SX, XMC+SX, xylylcarb+SX.

Combinations of the Present ingredient in the above Subgroup a-2 and the Present compound:
acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos (CYAP)+SX, demeton-S-methyl+SX, diazinon+SX, dichlorvos (DDVP)+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion (MEP)+SX, fenthion (MPP)+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion (DMTP)+SX, mevinphos+SX, monocrotophos+SX, naled (BRP)+SX, omethoate+SX, oxydemeton-methyl+SX, parathion+SX, parathion-methyl+SX, phenthoate (PAP)+SX, phorate+SX, phosalone+SX, phosmet (PMP)+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon (DEP)+SX, vamidothion+SX.

Combinations of the Present ingredient in the above Subgroup a-3 and the Present compound:
ethiprole+SX, fipronil+SX, flufiprole+SX, chlordane+SX, endosulfan+SX, alpha-endosulfan+SX.

Combinations of the Present ingredient in the above Subgroup a-4 and the Present compound:
afoxolaner+SX, fluralaner+SX, broflanilide+SX, fluxametamide+SX.

Combinations of the Present ingredient in the above Subgroup a-5 and the Present compound:
acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Combinations of the Present ingredient in the above Subgroup a-6 and the Present compound:
acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-{1-[(6-chloropyridin-3-yl)methyl]pyridin-2(1H)-ylidene}-2,2,2-trifluoroacetamide (1689566-03-7)+SX.

Combinations of the Present ingredient in the above Subgroup a-7 and the Present compound:
chlorantraniliprole+SX, cyantraniliprole+SX, cyclonilprole+SX, flubendiamide+SX, tetraniliprole+SX, cyhalodiamide+SX, 3-bromo-N-[2,4-dichloro-6-(methylcarbamoyl)

phenyl]-1-(3,5-dichloropyridin-2-yl)-1H-pyrazole-5-carboxamide (1104384-14-6)+SX.

Combinations of the Present ingredient in the above Subgroup a-8 and the Present compound:

*Beauveria bassiana*+SX, *Beauveria brongniartii*+SX, *Paecilomyces fumosoroseus*+SX, *Paecilomyces lilacinus*+SX, *Paecilomyces tenuipes*+SX, *Verticillium lecani*+SX, *Arthrobotrys dactyloides*+SX, *Bacillus thuringiensis*+SX, *Bacillus firmus*+SX, *Bacillus megaterium*+SX, *Hirsutella rhossiliensis*+SX, *Hirsutella minnesotensis*+SX, *Monacrosporium phymatopagus*+SX, *Pasteuria nishizawae*+SX, *Pasteuria penetrans*+SX, *Pasteuria usgae*+SX, *Verticillium chlamydosporium*+SX.

Combinations of the Present ingredient in the above Subgroup a-9 and the Present compound:

abamectin+SX, fluazaindolizine+SX, fluensulfone+SX, fluopyram+SX, tioxazafen+SX.

Combinations of the Present ingredient in the above Subgroup a-10 and the Present compound:

spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX, N-[3-chloro-1-(pyridin-3-yl)-1H-pyrazol-4-yl]-N-ethyl-3-(3,3,3-trifluoropropylsulfanyl)propaneamide (1477919-27-9)+SX, N-[3-chloro-1-(pyridin-3-yl)-1H-pyrazol-4-yl]-N-ethyl-3-(3,3,3-trifluoropropanesulfinyl)propaneamide (1477923-37-7)+SX, 5-(1,3-dioxan-2-yl)-4-[4-(trifluoromethyl)benzyloxy]pyrimidine (1449021-97-9)+SX, 2-[3-(ethanesulfonyl)pyridin-2-yl]-5-(trifluoromethanesulfonyl)benzoxazole (1616678-32-0)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propaneamide (1118626-57-5)+SX, 3-(4-chloro-2,6-dimethylphenyl)-4-[(ethoxycarbonyl)oxy]-8-methoxy-1-methyl-1,8-diazaspiro[4.5]dec-3-en-2-one (1229023-00-0)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazol-5-amine (885026-50-6)+SX, 3-endo-[2-propoxy-4-(trifluoromethyl)phenoxy]-9-{[5-(trifluoromethyl)pyridin-2-yl]oxy}-9-azabicyclo[3.3.1]nonane (1332838-17-1)+SX.

Combinations of the Present ingredient in the above Subgroup b-1 and the Present compound:

benalaxyl+SX, benalaxyl-M+SX, furalaxyl+SX, metalaxyl+SX, metalaxyl-M+SX, oxadixyl+SX, ofurace+SX.

Combinations of the Present ingredient in the above Subgroup b-2 and the Present compound:

benomyl+SX, carbendazim+SX, fuberidazole+SX, thiabendazole+SX, thiophanate+SX, thiophanate-methyl+SX.

Combination of the Present ingredient in the above Subgroup b-3 and the Present compound:

ethaboxam+SX.

Combinations of the Present ingredient in the above Subgroup b-4 and the Present compound:

benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penflufen+SX, penthiopyrad+SX, sedaxane+SX, pydiflumetofen+SX, boscalid+SX, pyraziflumid+SX, 3-difluoromethyl-N-methoxy-1-methyl-N-[(1R)-1-methyl-2-(2,4,6-trichlorophenyl)ethyl]pyrazole-4-carboxamide (1639015-48-7)+SX, 3-difluoromethyl-N-methoxy-1-methyl-N-[(1S)-1-methyl-2-(2,4,6-trichlorophenyl)ethyl]pyrazole-4-carboxamide (1639015-49-8)+SX, N-cyclopropyl-3-(difluoromethyl)-5-fluoro-N-(5-chloro-2-isopropylbenzyl)-1-methyl-1H-pyrazole-4-carboxamide (1255734-28-1)+SX, 3-difluoromethyl-1-methyl-N-(1,1,3-trimethylindan-4-yl)pyrazole-4-carboxamide (141573-94-6)+SX, 3-difluoromethyl-1-methyl-N-[(3R)-1,1,3-trimethylindan-4-yl]pyrazole-4-carboxamide (1352994-67-2)+SX, 3-difluoromethyl-N-(7-fluoro-1,1,3-trimethylindan-4-yl)-1-methylpyrazole-4-carboxamide (1383809-87-7)+SX, 3-difluoromethyl-N-[(3R)-7-fluoro-1,1,3-trimethylindan-4-yl]-1-methylpyrazole-4-carboxamide (1513466-73-3)+SX.

Combinations of the Present ingredient in the above Subgroup b-5 and the Present compound:

azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+SX, metominostrobin+SX, orysastrobin+SX, famoxadone+SX, fluoxastrobin+SX, fenamidone+SX, pyribencarb+SX.

Combinations of the Present ingredient in the above Subgroup b-6 and the Present compound:

cyazofamid+SX, amisulbrom+SX, binapacryl+SX, meptyldinocap+SX, dinocap+SX, fluazinam+SX.

Combination of the Present ingredient in the above Subgroup b-7 and the Present compound:
silthiofam+SX.

Combinations of the Present ingredient in the above Subgroup b-8 and the Present compound:
cyprodinil+SX, mepanipyrim+SX, pyrimethanil+SX.

Combinations of the Present ingredient in the above Subgroup b-9 and the Present compound:
fenpiclonil+SX, fludioxonil+SX.

Combinations of the Present ingredient in the above Subgroup b-10 and the Present compound:
biphenyl+SX, chloroneb+SX, dicloran+SX, quintozene+SX, tecnazene+SX, tolclofos-methyl+SX.

Combinations of the Present ingredient in the above Subgroup b-11 and the Present compound:
azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX.

Combinations of the Present ingredient in the above Subgroup b-12 and the Present compound:
dimethomorph+SX, flumorph+SX, pyrimorph+SX, benthiavalicarb+SX, benthivalicarb-isopropyl+SX, iprovalicarb+SX, valifenalate+SX, mandipropamid+SX.

Combination of the Present ingredient in the above Subgroup b-13 and the Present compound:
oxathiapiprolin+SX.

Combination of the Present ingredient in the above Subgroup b-14 and the Present compound:
picarbutrazox+SX.

Combinations of the Present ingredient in the above Subgroup b-15 and the Present compound:
ferbam+SX, mancozeb+SX, maneb+SX, metiram+SX, propineb+SX, thiram+SX, zineb+SX, ziram+SX.

Combinations of the Present ingredient in the above Subgroup b-16 and the Present compound:
captan+SX, captafol+SX, folpet+SX.

Combinations of the Present ingredient in the above Subgroup b-17 and the Present compound:
*Agrobacterium radiobactor* (such as strain 84)+SX, *Bacillus amyloliquefaciens*+SX, *Bacillus amyloliquefaciens*strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT332+SX, *Bacillus amyloliquefaciens* strain PTA4838+SX, *Bacillus pumilus*+SX, *Bacillus simplex* (such as strain CGF2856)+SX, *Bacillus subtilis*+SX, *Bacillus subtilis* strain QST713+SX, *Bacillus subtilis* strain HAI0404+SX, *Bacillus subtilis* strain Y1336+SX, *Variovorax paradoxus* (such as strain CGF4526)+SX, *Erwinia carotovora* (such as strain CGE234M403)+SX, *Pseudomonas fluorescens* (such as strain G7090)+SX, *Talaromyces flavus* (such as strain SAY-Y-94-01)+SX, *Trichoderma atroviride* (such as strain SKT-1)+SX, *Trichoderma harzianum*+SX, Harpin protein+SX.

Combinations of the Present ingredient in the above Subgroup b-18 and the Present compound:
bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclofthalam+SX, triazoxide+SX, flusulfamide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulfate+SX, Dodecylbenzenesulphonic acid bisethylenediamine copper [II]salt (DBEDC)+SX, organic copper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, 3-chloro-5-phenyl-6-methyl-4-(2,6-difluorophenyl) pyridazine (1358061-55-8)+SX, fenpicoxamid+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazol-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX.

Combinations of the Present ingredient in the above Subgroup c-1 and the Present compound:
ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX.

Combinations of the Present ingredient in the above Subgroup c-2 and the Present compound:

*Glomus* spp.+SX, *Glomus intraradices*+SX, *Glomus mosseae*+SX, *Glomus aggregatum*+SX, *Glomus etunicatum*+SX.

Combinations of the Present ingredient in the above Subgroup c-3 and the Present compound:

*Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*+SX, *Rhizobium* spp.+SX.

Combinations of the Present ingredient in the above Group (d) and the Present compound:

benoxacor+SX, cloquintocet-mexyl+SX, cyometrinil+SX, dichlormid+SX, fenchlorazole-ethyl+SX, fenclorim+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 (4-(dichloroacetyl)-1-oxa-4-azaspiro[4.5]decane)+SX.

Combinations of the Present ingredient in the above Group (e) and the Present compound:

DMC (1,1-bis(4-chlorophenyl)ethanol)+SX, FDMC (1,1-bis(4-chlorophenyl)-2,2,2-trifluoroethanol)+SX, bucarpolate+SX, N,N-dibutyl-4-chlorobenzenesulfonamide+SX, dietholate+SX, diethylmaleate+SX, 1-dodecyl-1H-imidazole+SX, N-(2-ethylhexyl)-8,9,10-trinorborn-5-ene-2,3-dicarboximide+SX, PSCP (phenylsaligenin cyclic phosphate)+SX, piperonyl butoxide+SX, piperonyl cyclonene+SX, piprotal+SX, propyl isome+SX, safroxan+SX, sesamex+SX, sesamolin+SX, sulfoxide+SX, tribufos+SX, TBPT (S,S,S-tributyl phosphorotrithioate)+SX, ETP (1,1,1-trichloro-2,3-expoxypropane)+SX, ETN (1,2-epoxy-1,2,3,4-tetrahydronaphthalene)+SX, TPP (triphenyl phosphate)+SX, Verbutin+SX.

Examples of the harmful arthropod on which the Present compound has efficacies include harmful insects and harmful acarines. Specific examples of the harmful arthropod include the followings.

Hemiptera Pests:

Delphacidae (for example, *Laodelphax striatellus, Nilaparvata lugens, Sogatella furcifera, Peregrinus maidis, Javesella pellucida, Perkinsiella saccharicida*, or *Tagosodes orizicolus*);

Cicadellidae (for example, *Nephotettix cincticeps, Nephotettix virescens, Nephotettix nigropictus, Recilia dorsalis, Empoasca onukii, Empoasca fabae, Dalbulus maidis*, or *Cofana spectra*);

Cercopidae (for example, *Mahanarva posticata* or *Mahanarva fimbriolata*);

Aphididae (for example, *Aphis fabae, Aphis glycines, Aphis gossypii, Aphis pomi, Aphis spiraecola, Myzus persicae, Brachycaudus helichrysi, Brevicoryne brassicae, Dysaphis plantaginea* (Rosy apple aphid), *Lipaphis erysimi, Macrosiphum euphorbiae, Aulacorthum solani, Nasonovia ribisnigri, Rhopalosiphum padi, Rhopalosiphum maidis, Toxoptera citricida, Hyalopterus pruni, Melanaphis sacchari, Tetraneura nigriabdominalis, Ceratovacuna lanigera*, or *Eriosoma lanigerum*);

Phylloxeridae (for example, *Daktulosphaira vitifoliae, Phylloxera devastatrix* (Pecan *phylloxera*), *Phylloxera notabilis* (Pecan leaf *phylloxera*), or *Phylloxera russellae* (Southern pecan leaf *phylloxera*));

Adelgidae (for example, *Adelges tsugae, Adelges piceae*, or *Aphrastasia pectinatae*);

Pentatomidae (for example, *Scotinophara lurida, Scotinophara coarctata* (Malayan rice black bug), *Nezara antennata, Eysarcoris aeneus, Eysarcoris lewisi, Eysarcoris ventralis, Eysarcoris annamita, Halyomorpha halys, Nezara viridula, Euschistus heros* (Brown stink bug), *Piezodorus guildinii* (Red banded stink bug), *Oebalus pugnax*, or *Dichelops melacanthus*);

Cydnidae (for example, *Scaptocoris castanea* (Burrower brown bug));

Alydidae (for example, *Riptortus pedestris, Leptocorisa chinensis*, or *Leptocorisa acuta*);

Coreidae (for example, *Cletus punctiger* or *Leptoglossus australis*);

Lygaeidae (for example, *Caverelius saccharivorus, Togo hemipterus*, or *Blissus leucopterus*);

Miridae (for example, *Trigonotylus caelestialium, Stenotus rubrovittatus, Stenodema calcarata*, or *Lygus lineolaris*);

Aleyrodidae (for example, *Trialeurodes vaporariorum, Bemisia tabaci, Dialeurodes citri, Aleurocanthus spiniferus, Aleurocanthus camelliae*, or *Pealius euryae*);

Diaspididae (for example, *Abgrallaspis cyanophylli, Aonidiella aurantii, Diaspidiotus perniciosus, Pseudaulacaspis pentagona, Unaspis yanonensis*, or *Unaspis citri*);

Coccidae (for example, *Ceroplastes rubens*);

Margarodidae (for example, *Icerya purchasi* or *Icerya seychellarum*);

Pseudococcidae (for example, *Phenacoccus solani, Phenacoccus solenopsis, Planococcus kraunhiae, Pseudococcus comstocki, Planococcus citri, Pseudococcus calceolariae, Pseudococcus longispinus*, or *Brevennia rehi*);

Psyllidae (for example, *Diaphorina citri, Trioza erytreae, Cacopsylla pyrisuga, Cacopsylla chinensis, Bactericera cockerelli*, or *Cacopsylla pyricola* (Pear *psylla*));

Tingidae (for example, *Corythucha ciliata, Corythucha marmorata, Stephanitis nashi*, or *Stephanitis pyrioides*);

Cimicidae (for example, *Cimex lectularius*);

Cicadidae (for example, *Quesada gigas* (Giant Cicada));

and the others.

Lepidoptera Pests:

Crambidae (for example, *Chilo suppressalis, Chilo polychrysus* (Darkheaded stem borer), *Scirpophaga innotata* (White stem borer), *Scirpophaga incertulas, Rupela albina, Cnaphalocrocis medinalis, Marasmia patnalis, Marasmia exigua, Notarcha derogata, Ostrinia furnacalis, Ostrinia nubilalis* (European corn borer), *Hellula undalis, Herpetogramma luctuosale, Pediasia teterrellus, Nymphula depunctalis*, or *Diatraea saccharalis* (Sugarcane borer));

Pyralidae (for example, *Elasmopalpus lignosellus* or *Plodia interpunctella*);

Noctuidae (for example, *Spodoptera litura, Spodoptera exigua, Mythimna separata, Mamestra brassicae, Sesamia inferens, Spodoptera mauritia, Naranga aenescens, Spodoptera frugiperda, Spodoptera exempta, Agrotis ipsilon, Autographa nigrisigna, Plusia festucae, Chrysodeixis includens* (Soybean looper), *Trichoplusia* spp., *Heliothis* spp. (for example, *Heliothis virescens*), *Helicoverpa* spp. (for example, *Helicoverpa armigera* or *Helicoverpa zea*), *Anticarsia gemmatalis* (Velvetbean caterpillar), *Alabama argillacea* (Cotton leafworm), or *Hydraecia immanis* (Hop vine borer));

Pieridae (for example, *Pieris rapae*);

Tortricidae (for example, *Grapholita molesta, Grapholita dimorpha, Leguminivora glycinivorella, Matsumuraeses azukivora, Adoxophyes orana fasciata, Adoxophyes honmai, Homona magnanima, Archips fuscocupreanus, Cydia pomo-* nella, *Tetramoera schistaceana*, *Epinotia aporema* (Bean Shoot Borer), or *Ecdytolopha aurantiana* (Citrus fruit borer));

Gracillariidae (for example, *Caloptilia theivora* or *Phyllonorycter ringoniella*);

Carposinidae (for example, *Carposina sasakii*);

Lyonetiidae (for example, *Leucoptera coffeella* (Coffee Leaf miner), *Lyonetia clerkella*, or *Lyonetia prunifoliella*);

Lymantriidae (for example, *Lymantria* spp. (for example, *Lymantria dispar*) or *Euproctis* spp. (for example, *Euproctis pseudoconspersa*));

Pluteliidae (for example, *Plutella xylostella*);

Gelechiidae (for example, *Anarsia lineatella*, *Helcystogramma triannulella*, *Pectinophora gossypiella*, *Phthorimaea operculella*, or *Tuta absoluta*);

Arctiidae (for example, *Hyphantria cunea*);

Castniidae (for example, *Telchin licus* (Giant Sugarcane borer));

Cossidae (for example, *Cossus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis*);

Hesperiidae (for example, *Parnara guttata*)

and the others.

Thysanoptera Pests:

Thripidae (for example, *Frankliniella occidentalis*, *Thrips palmi*, *Scirtothrips dorsalis*, *Thrips tabaci*, *Frankliniella intonsa*, *Stenchaetothrips biformis*, or *Echinothrips americanus*);

Phlaeothripidae (for example, *Haplothrips aculeatus*);

and the others.

Diptera Pests:

Anthomyiidae (for example, *Delia platura* or *Delia antiqua*);

Ulidiidae (for example, *Tetanops myopaeformis*);

Agromyzidae (for example, *Agromyza oryzae*, *Liriomyza sativae*, *Liriomyza trifolii*, or *Chromatomyia horticola*);

Chloropidae (for example, *Chlorops oryzae*);

Tephritidae (for example, *Bactrocera cucurbitae*, *Bactrocera dorsalis*, *Bactrocera latifrons*, *Bactrocera oleae*, *Bactrocera tryoni*, or *Ceratitis capitata*);

Ephydridae (for example, *Hydrellia griseola*, *Hydrellia philippina*, or *Hydrellia sasakii*);

Drosophilidae (for example, *Drosophila suzukii*);

Phoridae (for example, *Megaselia spiracularis*);

Psychodidae (for example, *Clogmia albipunctata*);

Sciaridae (for example, *Bradysia difformis*);

Cecidomyiidae (for example, *Mayetiola destructor* or *Orseolia oryzae*);

Diopsidae (for example, *Diopsis macrophthalma*);

Tipulidae (for example, *Tipula aino*, *Tipula oleracea* (Common cranefly), or *Tipula paludosa* (European cranefly))

and the others.

Coleoptera Pests:

Chrysomelidae (for example, *Diabrotica virgifera virgifera*, *Diabrotica undecimpunctata howardi*, *Diabrotica barberi*, *Diabrotica virgifera zeae*, *Diabrotica balteata*, *Diabrotica speciosa* (Cucurbit Beetle), *Cerotoma trifurcata*, *Oulema melanopus*, *Aulacophora femoralis*, *Phyllotreta striolata*, *Phyllotreta cruciferae* (Cabbage flea beetle), *Phyllotreta pusilla* (Western black flea beetle), *Psylliodes chrysocephala* (Cabbage stem flea beetle), *Leptinotarsa decemlineata*, *Oulema oryzae*, *Colaspis brunnea*, *Chaetocnema pulicaria*, *Chaetocnema confinis*, *Epitrix cucumeris*, *Dicladispa armigera*, *Myochrous denticollis* (southern corn leaf beetle), *Laccoptera quadrimaculata*, or *Epitrix hirtipennis*);

Carabidae (for example, *Stenolophus lecontei* (Seedcorn beetle) or *Clivina impressifrons* (Slender seedcorn beetle));

Scarabaeidae (for example, *Anomala cuprea*, *Anomala rufocuprea*, *Anomala albopilosa*, *Popillia japonica*, *Heptophylla picea*, *Rhizotrogus majalis* (European Chafer), *Tomarus gibbosus*, *Holotrichia* spp., *Phyllophaga* spp. (for example, *Phyllophaga crinita*), or *Diloboderus* spp. (for example, *Diloboderus abderus*));

Curculionidae (for example, *Araecerus coffeae*, *Cylas formicarius*, *Euscepes postfasciatus*, *Hypera postica*, *Sitophilus zeamais*, *Echinocnemus squameus*, *Lissorhoptrus oryzophilus*, *Rhabdoscelus lineatocollis*, *Anthonomus grandis*, *Sphenophorus venatus*, *Sphenophorus callosus* (Southern Corn Billbug), *Sternechus subsignatus* (Soybean stalk weevil), *Sphenophorus levis* (Sugarcane weevil), *Scepticus griseus*, *Scepticus uniformis*, *Zabrotes subfasciatus*, *Tomicus piniperda*, *Hypothenemus hampei* (Coffee Berry Borer), *Aracanthus* spp. (for example, *Aracanthus mourei*), or *Eutinobothrus brasiliensis* (cotton root borer));

Tenebrionidae (for example, *Tribolium castaneum* or *Tribolium confusum*);

Coccinellidae (for example, *Epilachna vigintioctopunctata*);

Bostrychidae (for example, *Lyctus brunneus*);

Ptinidae;

Cerambycidae (for example, *Anoplophora malasiaca* or *Migdolus fryanus*);

Elateridae (for example, *Melanotus okinawensis*, *Agriotes fuscicollis*, *Melanotus legatus*, *Anchastus* spp., *Conoderus* spp., *Ctenicera* spp., *Limonius* spp., or *Aeolus* spp.);

Staphylinidae (for example, *Paederus fuscipes*)

and the others.

Orthoptera Pests:

Acrididae (for example, *Locusta migratoria*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Two striped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya japonica*, or *Patanga succincta*);

Gryllotalpidae (for example, *Gryllotalpa orientalis*);

Gryllidae (for example, *Acheta domestica* or *Teleogryllus emma*);

Tettigoniidae (for example, *Anabrus simplex* (Mormon cricket))

and the others.

Hymenoptera Pests:

Tenthredinidae (for example, *Athalia rosae* or *Athalia japonica*);

*Solenopsis* spp.;

Formicidae (for example, *Atta capiguara* (Brown leaf-cutting ant));

and the others.

Blattodea Pests:

Blattellidae (for example, *Blattella germanica*);

Blattidae (for example, *Periplaneta fuliginosa*, *Periplaneta americana*, *Periplaneta brunnea*, or *Blatta orientalis*);

Termitidae (for example, *Reticulitermes speratus*, *Coptotermes formosanus*, *Incisitermes minor*, *Cryptotermes*

*domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae,* or *Cornitermes cumulans*)
and the others.

Acari Pests:

Tetranychidae (for example, *Tetranychus urticae, Tetranychus kanzawai, Tetranychus evansi, Panonychus citri, Panonychus ulmi,* or *Oligonychus* spp.);

Eriophyidae (for example, *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella,* or *Shevtchenkella* sp.);

Tarsonemidae (for example, *Polyphagotarsonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanensis, Dermacentor variabilis, Ixodes ovatus, Ixodes persulcatus, Ixodes scapularis, Amblyomma americanum, Boophilus microplus,* or *Rhipicephalus sanguineus*);

Acaridae (for example, *Tyrophagus putrescentiae* or *Tyrophagus similis*);

Pyroglyphidae (for example, *Dermatophagoides farinae* or *Dermatophagoides pteronyssinus*);

Cheyletidae (for example, *Cheyletus eruditus, Cheyletus malaccensis, Cheyletus moorei,* or *Cheyletiella yasguri*);

Sarcoptidae (for example, *Otodectes cynotis* or *Sarcoptes scabiei*);

Demodicidae (for example, *Demodex canis*);

Listrophoridae;

Haplochthoniidae;

Macronyssidae (for example, *Ornithonyssus bacoti* or *Ornithonyssus sylviarum*);

Dermanyssidae (for example, *Dermanyssus gallinae*);

Trombiculidae (for example, *Leptotrombidium akamushi*) and the others.

The agent for controlling harmful arthropods of the present invention comprises the Present compound and an inert carrier. The agent for controlling harmful arthropods of the present invention is usually prepared by mixing the Present compound with an inert carrier such as solid carrier, liquid carrier, and gaseous carrier, and as needed, adding a surfactant and other auxiliary agent for formulation, to formulate into an emulsifiable concentrate, an oil solution, a dust formulation, a granule, a wettable powder, a flowable, a microcapsule, an aerosol, a smoking agent, a poison bait, a resin formulation, a shampoo formulation, a paste-like formulation, a foam, a carbon dioxide formulation, a tablet, or the like. Such formulation may be processed into and used as a mosquito repellent coil, an electric mosquito repellent mat, a liquid mosquito repellent formulation, a smoking agent, a fumigant, a sheet formulation, a spot-on formulation, or a formulation for oral treatment. Also, an agent for controlling harmful arthropods of the present invention may be mixed with another insecticide, acaricide, nematicide, fungicide, plant growth regulator, herbicide, or synergist.

The agent for controlling harmful arthropods of the present invention usually comprises 0.01 to 95% by weight of the Present compound.

Examples of the solid carrier to be used in the formulation include fine powders and granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate, or hydrated silica), chemical fertilizers (for example, ammonium sulfate, ammonium phosphate, ammonium nitrate, urea, or ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, or the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile or isobutyronitrile); ethers (for example, diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, or 3-methoxy-3-methyl-1-butanol); acid amides (for example, DMF or dimethylacetamide); halogenated hydrocarbons (for example, dichloromethane, trichloroethane, or carbon tetrachloride); sulfoxides (for example, DMSO); propylene carbonate; and vegetable oils (for example, soybean oil or cottonseed oil).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent for formulation include binders, dispersants, colorants, and stabilizers. Specific examples thereof include casein, gelatin, saccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of base material of the resin formulation include vinyl chloride polymers, polyurethane, and the others, and a plasticizer such as phthalic acid esters (for example, dimethyl phthalate or dioctyl phthalate), adipic acid esters, and stearic acid may be added to these base materials, if necessary. The resin formulation may be prepared by mixing the Present compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, if necessary, to be processed into a shape such as a plate, film, tape, net, and string shape. These resin formulations may be processed into an animal collar, an animal ear tag, a sheet formulation, a trap string, a gardening support, or other products.

Examples of the base material for the poison bait include bait ingredients such as grain powders, vegetable oils, saccharides, and crystalline celluloses, and if necessary, with addition of an antioxidant such as dibutylhydroxytoluene and nordihydroguaiaretic acid, a preservative such as dehydroacetic acid, an accidental ingestion inhibitor for children and pets such as chili powder, an insect attraction fragrance such as cheese flavor, onion flavor, and peanut oil, or the other ingredient.

The method for controlling harmful arthropods of the present invention is carried out by applying an effective amount of the Present compound to harmful arthropods directly and/or habitats of pests (for example, plant bodies, soil, interiors of houses, or animal bodies). In the method for controlling harmful arthropods of the present invention, the Present compound is usually used in the form of an agent for controlling harmful arthropods of the present invention.

When the agent for controlling harmful arthropods of the present invention is used for controlling pests in an agricultural field, the application dose as an amount of the Present compound is usually within a range from 1 to 10,000 g per 10,000 m². The emulsifiable concentrate, the wettable powder, the flowable, or the like of the agent for controlling harmful arthropods of the present invention is usually applied by diluting it with water in such a way that a concentration of the active ingredient is within a range from 0.01 to 10,000 ppm. The granule, the dust formulation, or the like is usually applied as itself without diluting it.

These formulations and diluents of the formulations with water may be directly sprayed to harmful arthropods or plants such as crops to be protected from harmful arthropods, or applied to soil in cultivated areas to control pests that inhabit the soil.

Also, a resin formulation processed into sheet shape or string shape may be wrapped around crops, stretched near crops, spread on plant foot soil, or the like.

When the agent for controlling harmful arthropods of the present invention is used to control pests that live inside a house, the application dose as an amount of the Present compound is usually within a range from 0.01 to 1,000 mg per 1 m² of an area to be treated in the case of using it on a planar area. In the case of using it spatially, the application dose as an amount of the Present compound is usually within a range from 0.01 to 500 mg per 1 m³ of the space to be treated. When the agent for controlling harmful arthropods of the present invention is formulated into an emulsifiable concentrate, a wettable powder, a flowable, or the others, such formulation is usually applied after diluting it with water in such a way that a concentration of the active ingredient is within a range from 0.1 to 10,000 ppm, and then sparging it. In the case of being formulated into an oil solution, an aerosol, a smoking agent, a poison bait, or the others, such formulation is used as itself without diluting it.

When the agent for controlling harmful arthropods of the present invention is used for controlling external parasites of livestock such as cows, horses, pigs, sheep, goats, and chickens, and small animals such as dogs, cats, rats, and mice, the agent of the present invention may be applied to the animals by a known method in the veterinary field. Specifically, when systemic control is intended, the agent of the present invention is administered to the animals as a tablet, a mixture with feed, or a suppository, or by injection (including intramuscular, subcutaneous, intravenous, and intraperitoneal injections), or the like. On the other hand, when non-systemic control is intended, the agent of the present invention is applied to the animals by means of spraying of the oil solution or aqueous solution, pour-on or spot-on treatment, or washing of the animal with a shampoo formulation, or by putting a collar or an ear tag made of the resin formulation to the animal, or the like. In the case of administering to an animal body, the dose of the Present compound is usually within a range from 0.1 to 1,000 mg per 1 kg of the animal body weight.

EXAMPLES

The following Examples including Preparation Examples, Formulation Examples, and Test Examples serve to illustrate the present invention more in detail, which should not intend to limit the present invention.

First, regarding the preparation of the Present compound, the Preparation Examples are shown below.

Reference Preparation Example 1(1)

To a mixture of a 1.6 M solution of butyllithium in hexane (54 mL) and THF (41 mL) was added dropwise a mixture of ethyl methyl sulfone (9.3 g) and THF (24 mL) at −78° C. To the reaction mixture was added dropwise a mixture of 5-bromo-2-cyanopyridine (12 g) and THF (41 mL) at −78° C. After being gradually warmed to room temperature, to the reaction mixture was added 2N hydrochloric acid, and the mixture was stirred for 30 minutes. The resulting mixture was extracted with ethyl acetate, and the resulting organic layers were washed with saturated brine. The resulting organic layers were dried over anhydrous sodium sulfate, and then concentrated under reduced pressure to give the Intermediate compound 1 represented by the following formula (13 g).

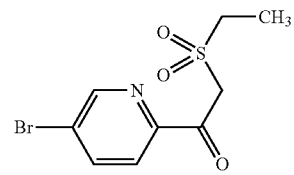

Intermediate compound 1: $^1$H NMR (CDCl$_3$): δ 8.79 (1H, d), 8.04-7.98 (2H, m), 4.97 (2H, s), 3.28 (2H, q), 1.46 (3H, t).

Reference Preparation Example 1(2)

The compound prepared according to the process described in the Reference Preparation Example 1(1) and the physical property thereof are shown below.
The compound represented by formula (A-1)

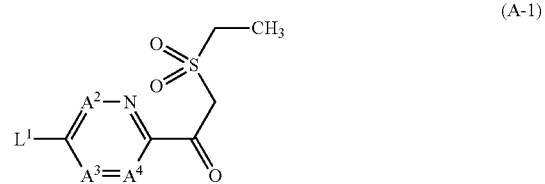

wherein $L^1$, $A^2$, $A^3$, and $A^4$ represent the combination indicated in Table 18.

TABLE 18

| Intermediate compound | $L^1$ | $A^2$ | $A^3$ | $A^4$ |
|---|---|---|---|---|
| 2 | F | CH | CH | CH |

Intermediate compound 2: ¹H-NMR (CDCl₃) δ: 8.57 (1H, d), 8.19 (1H, dd), 7.62-7.55 (1H, m), 4.97 (2H, s), 3.30 (2H, q), 1.47 (3H, t).

Reference Preparation Example 2

A mixture of methyl 5-chloro-2-pyrazinecarboxylate (10 g), sodium methoxide (a 28% solution in methanol) (28 mL), and THF (100 mL) was stirred under ice-cooling for 3 hours. To the resulting reaction mixture was added ethyl methyl sulfone (18 mL) under ice-cooling. The reaction mixture was warmed to 80° C., and heated with stirring for 24 hours. The resulting reaction mixture was allowed to cool to room temperature, then 2N hydrochloric acid was added thereto, and the mixture was extracted with ethyl acetate. The resulting organic layers were dried over anhydrous sodium sulfate, and concentrated. The resulting residues were subjected to silica gel chromatography to give the Intermediate compound 3 represented by the following formula (11 g).

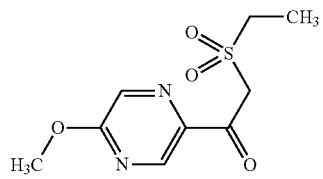

Intermediate compound 3: ¹H-NMR (CDCl₃) δ: 8.91 (1H, d), 8.25 (1H, d), 4.87 (2H, s), 4.08 (3H, s), 3.29 (2H, q), 1.47 (3H, t).

Reference Preparation Example 3(1)

To a mixture of oxalyl chloride (8.9 mL) and chloroform (68 mL) was added dropwise DMF (8 mL) under ice-cooling. The resulting mixture was stirred under ice-cooling for 30 minutes, and then stirred at room temperature for 1.5 hours. The mixture was ice-cooled, and then butyl vinyl ether (26 mL) was added dropwise thereto. The mixture was warmed to room temperature, then stirred for 2 hours, and then to the mixture was added dropwise a mixture of the Intermediate compound 1 (10 g), triethylamine (33 mL), and chloroform (23 mL) under ice-cooling. The mixture was warmed to room temperature, and then stirred for 1.5 hours. The resulting mixture was added to a saturated aqueous solution of ammonium chloride, and extracted with chloroform. The resulting organic layers were washed with water and saturated brine, then dried over anhydrous sodium sulfate, and concentrated under reduced pressure. The resulting residues were diluted with ethanol (10 mL), and then a 28% aqueous solution of ammonia (10 mL) was added thereto at room temperature. The mixture was warmed to 60° C., heated with stirring for 3 hours, then allowed to cool to room temperature, added to a saturated aqueous solution of sodium hydrogen carbonate, and the mixture was extracted with ethyl acetate. The resulting organic layers were dried over anhydrous sodium sulfate, and then concentrated under reduced pressure. The resulting residues were subjected to silica gel chromatography to give the Intermediate compound 4 represented by the following formula (4.5 g).

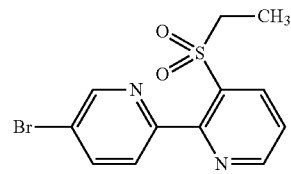

Intermediate compound 4: ¹H NMR (CDCl₃): δ 8.87 (1H, dd), 8.68 (1H, d), 8.49 (1H, dd), 8.01-7.98 (m, 1H), 7.74 (1H, d), 7.56 (1H, dd), 3.86 (2H, q), 1.37 (3H, t).

Reference Preparation Example 3(2)

The compounds prepared according to the process described in the Reference Preparation Example 3(1) and the physical properties thereof are shown below.

The compound represented by formula (A-2)

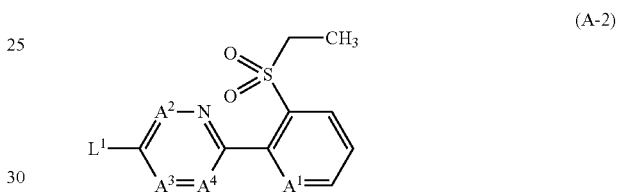

(A-2)

wherein $L^1$, $A^1$, $A^2$, $A^3$, and $A^4$ represent any one combination indicated in Table 19.

TABLE 19

| Intermediate compound | $L^1$ | $A^1$ | $A^2$ | $A^3$ | $A^4$ |
|---|---|---|---|---|---|
| 5 | F | N | CH | CH | CH |
| 6 | OCH₃ | N | CH | N | CH |

Intermediate compound 5: ¹H-NMR (CDCl₃) δ: 8.88 (1H, dd), 8.52-8.46 (2H, m), 7.87 (1H, dd), 7.62-7.54 (2H, m), 3.86 (2H, q), 1.38 (3H, t).

Intermediate compound 6: ¹H-NMR (CDCl₃) δ: 8.74 (1H, dd), 8.66 (1H, dd), 8.49 (1H, d), 8.20 (1H, d), 7.55 (1H, dd), 4.05 (3H, s), 3.85 (2H, q), 1.38 (3H, t).

Reference Preparation Example 4

To a mixture of 3-chloropyridine-2-carbonitrile (54 g) and THF (300 mL) was added dropwise a 1 M solution of methylmagnesium bromide in THF (500 mL) under ice-cooling. The reaction mixture was stirred under ice-cooling for 2 hours. The resulting reaction mixture was added to 2N hydrochloric acid under ice-cooling, and the mixture was stirred for 30 minutes. To the mixture was added a 1N aqueous solution of sodium hydroxide so that the pH of the solution was set to be 8, and then the mixture was extracted with ethyl acetate. The resulting organic layers were washed with saturated brine, and then the organic layers were dried over anhydrous sodium sulfate. The organic layers were concentrated under reduced pressure to give the Intermediate compound 7 represented by the following formula (58 g).

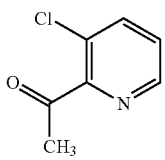

Intermediate compound 7: ¹H-NMR (CDCl₃) δ: 8.55 (1H, dd), 7.80 (1H, dd), 7.38 (1H, dd), 2.70 (3H, s).

Reference Preparation Example 5

To a suspension of sodium hydride (oily, 60%) (57 g) and DMF (560 mL) was added dropwise ethanethiol (100 mL) under ice-cooling. To the resulting mixture was added dropwise a mixture of the Intermediate compound 7 (204 g) and DMF (190 mL) under ice-cooling. The resulting reaction mixture was stirred under ice-cooling for 1 hour, and then added to ice water. The precipitated solids were filtered, and washed with water. The resulting solids were dissolved into ethyl acetate, the resulting solution was washed with saturated brine, and then the organic layers were dried over sodium sulfate. The resulting organic layers were concentrated under reduced pressure, and then the resulting solids were washed with hexane to give the Intermediate compound 8 represented by the following formula (160 g).

Intermediate compound 8: ¹H-NMR (CDCl₃) δ: 8.40 (1H, dd), 7.69 (1H, dd), 7.37 (1H, dd), 2.92 (2H, q), 2.72 (3H, s), 1.40 (3H, t).

Reference Preparation Example 6

To a mixture of the Intermediate compound 8 (5.4 g), glyoxylic acid monohydrate (2.8 g), and methanol (90 mL) was added dropwise a mixture of sodium hydroxide (2.4 g) and methanol (60 mL) under ice-cooling. The reaction mixture was stirred at 60° C. for 2 hours. The reaction mixture was allowed to cool to room temperature, and then acetic acid (11 mL) and hydrazine monohydrate (2.3 g) were sequentially added thereto. The resulting mixture was stirred at 100° C. for 19 hours. The resulting mixture was allowed to cool to room temperature, then a saturated aqueous solution of ammonium chloride was added thereto, and the mixture was extracted with chloroform. The resulting organic layers were dried over sodium sulfate, and concentrated under reduced pressure. The resulting residues were subjected to silica gel chromatography to give the Intermediate compound 9 represented by the following formula (3.8 g).

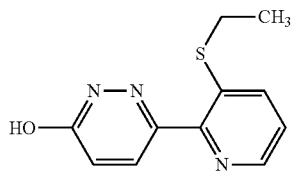 [SMILES: CCSc1cccnc1-c1ccc(O)nn1]

Intermediate compound 9: ¹H-NMR (CDCl₃) δ: 10.60 (1H, br s), 8.43 (1H, dd), 8.13 (1H, d), 7.71 (1H, dd), 7.29 (1H, dd), 7.05 (1H, d), 2.95 (2H, q), 1.35 (3H, t).

Reference Preparation Example 7

To a mixture of the Intermediate compound 9 (4.2 g) and chloroform (60 mL) was added 70% mCPBA (8.7 g) under ice-cooling. The resulting mixture was warmed to room temperature, and then stirred for 12 hours. To the resulting reaction mixture were added a saturated aqueous solution of sodium hydrogen carbonate and sodium thiosulfate, and the mixture was extracted with chloroform. The resulting organic layers were dried over anhydrous sodium sulfate, and concentrated under reduced pressure to give the Intermediate compound 10 represented by the following formula (4.7 g).

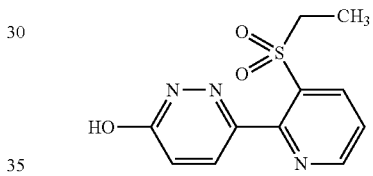

Intermediate compound 10: ¹H-NMR (CDCl₃) δ: 11.66 (1H, s), 8.90 (1H, dd), 8.49 (1H, dd), 7.78 (1H, d), 7.61 (1H, dd), 7.10 (1H, d), 3.66 (2H, q), 1.38 (3H, t).

Reference Preparation Example 8

To a mixture of the Intermediate compound 10 (2.0 g) and toluene (8 mL) were sequentially added DMF (one drop) and phosphorus oxybromide (4.3 g) at room temperature. The mixture was stirred at 100° C. for 9 hours. The resulting mixture was allowed to cool to room temperature, then water was added thereto, and the mixture was extracted with chloroform. The resulting organic layers were washed with water and saturated brine, then dried over sodium sulfate, and concentrated under reduced pressure. The resulting residues were subjected to silica gel chromatography to give the Intermediate compound 11 represented by the following formula (2.1 g).

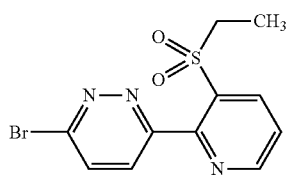

Intermediate compound 11: ¹H-NMR (CDCl₃) δ: 8.93 (1H, dd), 8.54 (1H, dd), 7.88-7.81 (2H, m), 7.66 (1H, dd), 3.89 (2H, q), 1.40 (3H, t).

Reference Preparation Example 9

A mixture of the Intermediate compound 6 (4.5 g) and 12N hydrochloric acid (20 mL) was heated with stirring at 100° C. for 1 hour. The reaction mixture was allowed to cool to room temperature, and then ice water (100 mL) was added thereto. To the mixture was added a saturated aqueous solution of sodium hydrogen carbonate to alkalify it, and the mixture was extracted with ethyl acetate. The resulting organic layers were dried over anhydrous sodium sulfate, and concentrated under reduced pressure. The resulting residues were subjected to silica gel chromatography to give the Intermediate compound 12 represented by the following formula (4.3 g).

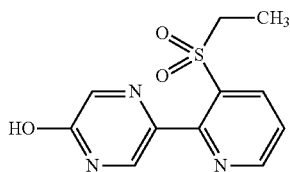 [SMILES: CCS(=O)(=O)c1cccnc1-c1cnc(O)cn1]

Intermediate compound 12: $^1$H-NMR (CDCl$_3$) δ: 8.81 (1H, dd), 8.47 (1H, dd), 8.21 (1H, d), 7.97 (1H, d), 7.52 (1H, dd), 3.83 (2H, q), 1.39 (3H, t).

Reference Preparation Example 10

A mixture of the Intermediate compound 12 (4.3 g), phosphorus oxychloride (12 mL), and toluene (60 mL) was heated with stirring at 100° C. for 2 hours. The resulting reaction mixture was allowed to cool to room temperature, and then concentrated under reduced pressure. To the resulting residues was added water, and the resulting mixture was extracted with chloroform. The resulting organic layers were dried over anhydrous sodium sulfate, and concentrated under reduced pressure to give the Intermediate compound 13 represented by the following formula (4.6 g).

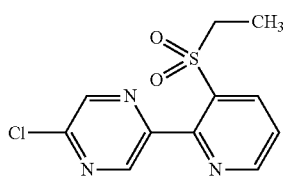 [SMILES: CCS(=O)(=O)c1cccnc1-c1cnc(Cl)cn1]

Intermediate compound 13: $^1$H-NMR (CDCl$_3$) δ: 8.94 (1H, dd), 8.90 (1H, dd), 8.59 (1H, d), 8.52 (1H, d), 7.65 (1H, dd), 3.81 (2H, q), 1.39 (3H, t).

Reference Preparation Example 11

The Intermediate compound 14 represented by the following formula was prepared by using phosphorus oxychloride instead of phosphorus oxybromide according to the process described in the Reference Preparation Example 8.

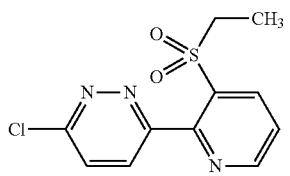 [SMILES: CCS(=O)(=O)c1cccnc1-c1ccc(Cl)nn1]

Intermediate compound 14: $^1$H-NMR (CDCl$_3$) δ: 8.93 (1H, dd), 8.54 (1H, dd), 7.96 (1H, d), 7.71 (1H, d), 7.66 (1H, dd), 3.89 (2H, q), 1.41 (3H, t).

Reference Preparation Example 12

To a mixture of methyl 6-bromonicotinate (10 g), tetrakistriphenylphosphinepalladium(0) (1.1 g), copper iodide (2.7 g), lithium chloride (2.9 g), and toluene (150 mL) was added 3-fluoro-2-(tributylstannyl)pyridine (24 g). The reaction mixture was stirred with heating at 110° C. under reflux for 5 hours. To the resulting reaction mixture was added a saturated aqueous solution of sodium hydrogen carbonate, and the mixture was extracted with ethyl acetate. The resulting organic layers were dried over anhydrous sodium sulfate, and concentrated under reduced pressure. The resulting residues were subjected to silica gel chromatography to give the Intermediate compound 15 represented by the following formula (8.6 g).

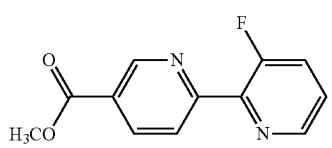

Intermediate compound 15: $^1$H-NMR (CDCl$_3$) δ: 9.39 (1H, s), 8.64-8.60 (1H, m), 8.44 (1H, dd), 8.11 (1H, d), 7.63-7.55 (1H, m), 7.46-7.39 (1H, m), 4.00 (3H, s).

Reference Preparation Example 13

The Intermediate compound 16 represented by the following formula (0.88 g) was prepared by using the Intermediate compound 15 (1.0 g) instead of the Intermediate compound 7 according to the process described in the Reference Preparation Example 5.

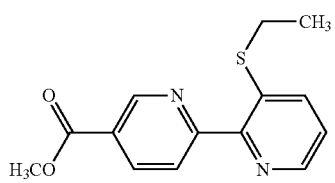

Intermediate compound 16: $^1$H-NMR (CDCl$_3$) δ: 9.33 (1H, d), 8.47 (1H, dd), 8.42 (1H, dd), 8.11 (1H, dd), 7.74 (1H, dd), 7.31 (1H, dd), 3.98 (3H, s), 2.91 (2H, q), 1.32 (3H, t).

Reference Preparation Example 14

The Intermediate compound 17 represented by the following formula (2.0 g) was prepared by using the Intermediate compound 16 instead of the Intermediate compound 9 according to the process described in the Reference Preparation Example 7.

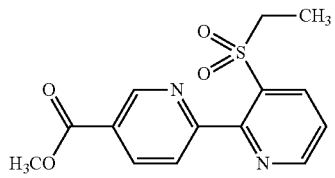

Intermediate compound 17: $^1$H-NMR (CDCl$_3$) δ: 9.23 (1H, dd), 8.91 (1H, dd), 8.51 (1H, dd), 8.47 (1H, dd), 7.91 (1H, dd), 7.60 (1H, dd), 3.99 (3H, s), 3.90 (2H, q), 1.39 (3H, t).

Reference Preparation Example 15

A mixture of the Intermediate compound 17 (2.1 g) and 6N hydrochloric acid (10 mL) was heated with stirring at 100° C. for 4 hours. The resulting reaction mixture was allowed to cool to room temperature, and then the precipitated solids were collected by filtration. The resulting solids were washed with hydrochloric acid of which the pH was adjusted to 4, and dried to give the Intermediate compound 18 represented by the following formula (2.1 g).

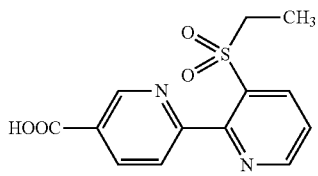 [SMILES: CCS(=O)(=O)c1cccnc1-c1ccc(C(=O)O)cn1]

Intermediate compound 18: $^1$H-NMR (DMSO-D6) δ: 9.13 (1H, d), 8.99 (1H, dd), 8.50-8.42 (2H, m), 7.92 (1H, d), 7.83 (1H, dd), 3.90 (2H, q), 1.24 (3H, t).

Reference Preparation Example 16

To an autoclave reactor was added a mixture of the Intermediate compound 11 (600 mg), palladium(II) acetate (8 mg), 1,1'-bis(diphenylphosphino)ferrocene (122 mg), sodium acetate (300 mg), and ethanol (3.7 mg), and the mixture was heated with stirring at 120° C. under carbon monoxide atmosphere. The resulting reaction mixture was concentrated, and the resulting residues were subjected to silica gel chromatography to give the Intermediate compound 19 represented by the following formula (410 mg).

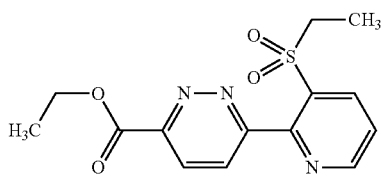 [SMILES: CCOC(=O)c1ccc(-c2ncccc2S(=O)(=O)CC)nn1]

Intermediate compound 19: $^1$H-NMR (CDCl$_3$) δ: 8.96 (1H, dd), 8.56 (1H, dd), 8.40 (1H, d), 8.12 (1H, d), 7.68 (1H, dd), 4.61 (2H, q), 3.97 (2H, q), 1.51 (3H, t), 1.41 (3H, t).

Reference Preparation Example 17

A mixture of the Intermediate compound 19 (410 mg) and 12N hydrochloric acid (5 mL) was heated with stirring at 50° C. for 6 hours. The resulting reaction mixture was concentrated under reduced pressure, to the resulting residues was added toluene, and the mixture was concentrated under reduced pressure to give the Intermediate compound 20 represented by the following formula (350 mg).

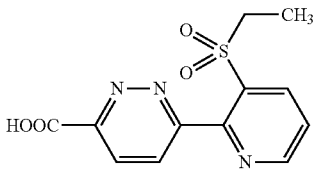 [SMILES: CCS(=O)(=O)c1cccnc1-c1ccc(C(=O)O)nn1]

Intermediate compound 20: $^1$H-NMR (DMSO-D$_6$) δ: 9.07 (1H, dd), 8.55 (1H, dd), 8.40 (1H, d), 8.24 (1H, d), 7.92 (1H, dd), 3.84 (2H, q), 1.26 (3H, t).

Reference Preparation Example 18

To a mixture of the Intermediate compound 16 (500 mg), methanol (1 mL), and THF (10 mL) was added sodium borohydride (140 mg) under ice-cooling. The reaction mixture was stirred at room temperature for 12 hours. To the resulting reaction mixture was added water, and the mixture was extracted with ethyl acetate. The resulting organic layers were dried over anhydrous sodium sulfate, and concentrated under reduced pressure. The resulting residues were subjected to silica gel chromatography to give the Intermediate compound 21 represented by the following formula (340 mg).

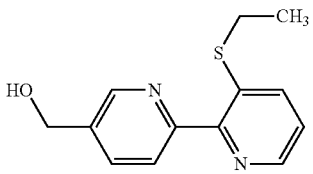 [SMILES: CCSc1cccnc1-c1ccc(CO)cn1]

Intermediate compound 21: $^1$H-NMR (CDCl$_3$) δ: 8.62 (1H, d), 8.45 (1H, dd), 7.89 (1H, d), 7.79 (1H, dd), 7.72 (1H, dd), 7.28 (1H, dd), 4.75 (2H, s), 2.89 (2H, q), 1.30 (3H, t).

Reference Preparation Example 19

To an autoclave reactor were added the Intermediate compound 5 (1.0 g), NMP (8 mL), and a 40% solution of methylamine in methanol (3.0 g), and the mixture was heated with stirring at 130° C. for 24 hours. The resulting reaction mixture was allowed to cool to room temperature, water was added thereto, and the mixture was extracted with ethyl acetate. The resulting organic layers were dried over anhydrous sodium sulfate, and then concentrated under reduced pressure. The resulting residues were subjected to silica gel chromatography to give the Intermediate compound 22 represented by the following formula (0.62 g).

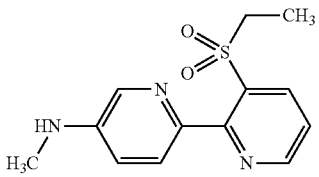 [SMILES: CCS(=O)(=O)c1cccnc1-c1ccc(NC)cn1]

Intermediate compound 22: $^1$H-NMR (CDCl$_3$) δ: 8.82 (1H, d), 8.46 (1H, d), 8.01 (1H, d), 7.77 (1H, d), 7.44 (1H, dd), 7.00 (1H, dd), 4.04 (1H, br s), 3.95 (2H, q), 2.93 (3H, d), 1.37 (3H, t).

Reference Preparation Example 20

A mixture of the Intermediate compound 14 (4.0 g), cyclopentyl methyl ether (5 mL), and 4-methoxybenzylamine (10 mL) was heated with stirring at 140° C. for 5 hours. To the resulting reaction mixture was added water, and the precipitated solids were collected by filtration. The resulting solids were washed with water and MTBE, and dried to give the Intermediate compound 23 represented by the following formula (2.6 g).

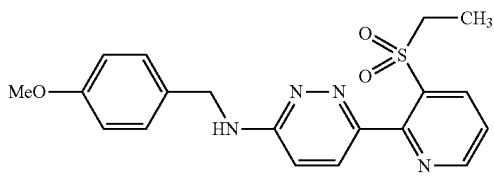 [SMILES: CCS(=O)(=O)c1cccnc1-c1ccc(NCc2ccc(OC)cc2)nn1]

Intermediate compound 23: $^1$H-NMR (CDCl$_3$) δ: 8.86 (1H, dd), 8.50 (1H, dd), 7.70 (1H, d), 7.53 (1H, dd), 7.32 (2H, d), 6.91 (2H, d), 6.77 (1H, d), 5.24 (1H, br s), 4.60 (2H, d), 3.96 (2H, q), 3.82 (3H, s), 1.39 (3H, t).

Reference Preparation Example 21

A mixture of the Intermediate compound 23 (2.6 g), sulfuric acid (3 mL), and water (1 mL) was heated with stirring at 60° C. for 4 hours. To the resulting reaction mixture was added ice, and sodium hydroxide was added thereto to adjust the pH to 9. The mixture was extracted with ethyl acetate. The resulting organic layers were dried over anhydrous sodium sulfate, and concentrated under reduced pressure. The resulting solids were washed with MTBE, and dried to give the Intermediate compound 24 represented by the following formula (1.6 g).

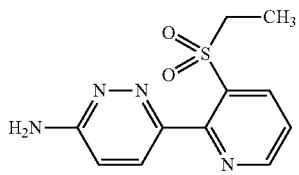 [SMILES: CCS(=O)(=O)c1cccnc1-c1ccc(N)nn1]

Intermediate compound 24: $^1$H-NMR (CDCl$_3$) δ: 8.87 (1H, dd), 8.50 (1H, dd), 7.78 (1H, d), 7.55 (1H, dd), 6.91 (1H, d), 5.77 (2H, s), 3.89 (2H, q), 1.39 (3H, t).

Preparation Example 1

To a mixture of 2-chloro-5-(trifluoromethyl)pyridine (360 mg), tris(benzylideneacetone)palladium(0) (28 mg), 2-(ethylsulfanyl)phenylboronic acid pinacol ester (530 mg), 2-dicyclohexylphosphino-2',6'-dimethoxybiphenyl (50 mg), and tripotassium phosphate (850 mg) was added 1,4-dioxane (6 mL), and the mixture was heated with stirring at 100° C. for 5 hours. To the resulting reaction mixture was added saturated brine, and the mixture was extracted with ethyl acetate. The resulting organic layers were dried over anhydrous sodium sulfate, and concentrated under reduced pressure. The resulting residues were subjected to silica gel chromatography to give the Present compound 1 represented by the following formula (320 mg).

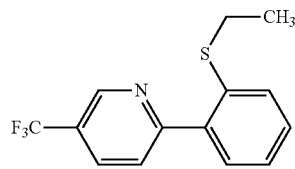 [SMILES: CCSc1ccccc1-c1ccc(C(F)(F)F)cn1]

Present compound 1: $^1$H-NMR (CDCl$_3$) δ: 8.98 (1H, d), 7.99 (1H, dd), 7.74 (1H, d), 7.49-7.44 (2H, m), 7.40 (1H, td), 7.29 (1H, td), 2.86 (2H, q), 1.24 (3H, t).

Preparation Example 2

The Present compound represented by the following formula 2 (140 mg) was prepared by using the Present compound 1 instead of the Intermediate compound 9 according to the process described in the Reference Preparation Example 7.

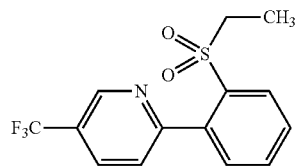 [SMILES: CCS(=O)(=O)c1ccccc1-c1ccc(C(F)(F)F)cn1]

Present compound 2: $^1$H-NMR (CDCl$_3$) δ: 8.89 (1H, br s), 8.18 (1H, dd), 8.05 (1H, dd), 7.74 (1H, td), 7.67 (1H, td), 7.61 (1H, d), 7.45 (1H, dd), 3.50 (2H, q), 1.30 (3H, t).

Preparation Example 3

The Present compound 3 represented by the following formula was prepared by using 2,3-dichloro-5-trifluoromethylpyridine instead of 2-chloro-5-trifluoromethylpyridine according to the process described in the Preparation Example 1.

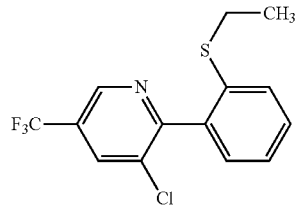 [SMILES: CCSc1ccccc1-c1ncc(C(F)(F)F)cc1Cl]

Present compound 3: $^1$H-NMR (CDCl$_3$) δ: 8.84 (1H, d), 8.04 (1H, d), 7.50 (1H, dd), 7.44 (1H, td), 7.33 (1H, td), 7.27 (1H, dd), 2.84 (2H, q), 1.21 (3H, t).

Preparation Example 4

The Present compound 4 represented by the following formula was prepared by using the Present compound 3 instead of the Intermediate compound 9 according to the process described in the Reference Preparation Example 7.

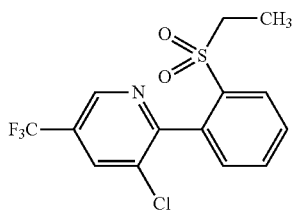 [SMILES: CCS(=O)(=O)c1ccccc1-c1ncc(C(F)(F)F)cc1Cl]

Present compound 4: ¹H-NMR (CDCl₃) δ: 8.78-8.75 (1H, m), 8.15-8.13 (1H, m), 8.07-8.06 (1H, m), 7.77 (1H, td), 7.70 (1H, td), 7.42 (1H, dd), 3.28 (2H, br s), 1.26 (3H, t).

Preparation Example 5(1)

A mixture of the Intermediate compound 4 (1 g), copper powder (580 mg), and NMP (6 mL) was heated with stirring under 1-iodopentafluoroethane atmosphere at 140° C. for 5 hours. The resulting mixture was allowed to cool to room temperature, and then a saturated aqueous solution of sodium hydrogen carbonate and a 28% aqueous solution of ammonia were added thereto. The resulting mixture was filtered, and then extracted with ethyl acetate. The resulting organic layers were washed with water and saturated brine, then dried over anhydrous sodium sulfate, and concentrated under reduced pressure. The resulting residues were subjected to silica gel chromatography to give the Present compound 6 represented by the following formula (70 mg).

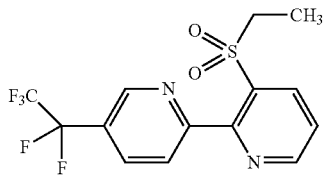 [SMILES: CCS(=O)(=O)c1cccnc1-c1ccc(C(F)(F)C(F)(F)F)cn1]

Present compound 6: ¹H-NMR (CDCl₃) δ: 8.91 (1H, dd), 8.85 (1H, d), 8.52 (1H, dd), 8.10 (1H, dd), 7.99 (1H, dd), 7.62 (1H, dd), 3.88 (2H, q), 1.39 (3H, t).

Preparation Example 5(2)

The compounds prepared according to the process described in the Preparation Example 5(1) and the physical properties thereof are shown below.

The compound represented by formula (I-10)

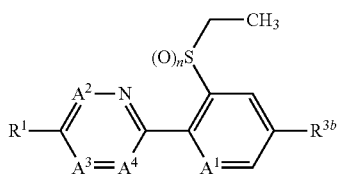

(I-10)

wherein $A^1$, $A^2$, $A^3$, $A^4$, $R^1$, $R^{3b}$, and n represent any one combination indicated in Table 20.

TABLE 20

| Present compound | $R^1$ | $A^1$ | $A^2$ | $A^3$ | $A^4$ | $R^{3b}$ | n |
|---|---|---|---|---|---|---|---|
| 5 | CF₃ | N | CH | CH | CH | H | 2 |
| 7 | CF₂CF₂CF₃ | N | CH | CH | CH | H | 2 |
| 8 | CF₂CF₂CF₂CF₃ | N | CH | CH | CH | H | 2 |
| 9 | CF₂CF₂CF₃ | N | N | CH | CH | H | 2 |
| 10 | CF₂CF₂CF₂CF₃ | N | N | CH | CH | H | 2 |
| 11 | CF₂CF₂CF₂CF₂CF₃ | N | N | CH | CH | H | 2 |

Present compound 5: ¹H-NMR (CDCl₃) δ: 8.91-8.89 (2H, m), 8.51 (1H, dd), 8.12 (1H, dd), 7.97 (1H, d), 7.61 (1H, dd), 3.88 (2H, q), 1.39 (3H, t).

Present compound 7: ¹H-NMR (CDCl₃) δ: 8.92 (1H, dd), 8.84 (1H, d), 8.52 (1H, dd), 8.09 (1H, dd), 8.00 (1H, d), 7.63 (1H, dd), 3.88 (2H, q), 1.40 (3H, t).

Present compound 8: ¹H-NMR (CDCl₃) δ: 8.92 (1H, dd), 8.84 (1H, d), 8.52 (1H, dd), 8.09 (1H, dd), 8.00 (1H, d), 7.63 (1H, dd), 3.88 (2H, q), 1.39 (3H, t).

Present compound 9: ¹H-NMR (CDCl₃) δ: 8.97 (1H, dd), 8.57 (1H, dd), 8.17 (1H, d), 8.02 (1H, d), 7.71 (1H, dd), 3.91 (2H, q), 1.42 (3H, t).

Present compound 10: ¹H-NMR (CDCl₃) δ: 8.97 (1H, dd), 8.57 (1H, dd), 8.17 (1H, d), 8.02 (1H, d), 7.71 (1H, dd), 3.91 (2H, q), 1.42 (3H, t).

Present compound 11: ¹H-NMR (CDCl₃) δ: 8.97 (1H, dd), 8.57 (1H, dd), 8.17 (1H, d), 8.03 (1H, d), 7.71 (1H, dd), 3.91 (2H, q), 1.42 (3H, t).

Preparation Example 6(1)

To a mixture of the Intermediate compound 4 (500 mg), allylpalladium(II) chloride dimer (27 mg), 5-(di-tert-butylphosphino)-1',3',5'-triphenyl-1'H-[1,4']-bipyrazole (160 mg), phenol (220 mg), and cyclopentyl methyl ether (3 mL) were added 2,2,3,3,3-pentafluoropropylamine (350 mg) and potassium tert-butoxide (240 mg). The reaction mixture was heated at 100° C. for 2 hours. To the resulting reaction mixture was added water, and the mixture was extracted with ethyl acetate. The resulting organic layers were sequentially washed with a saturated aqueous solution of sodium hydrogen carbonate and saturated brine, dried over anhydrous sodium sulfate, and concentrated under reduced pressure. The resulting residues were subjected to silica gel chromatography to give the Present compound 12 represented by the following formula (430 mg).

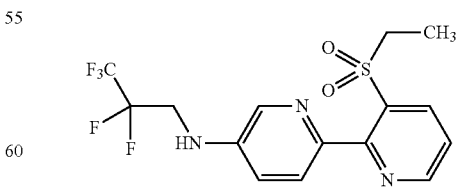

Present compound 12: ¹H-NMR (CDCl₃) δ: 8.84 (1H, dd), 8.47 (1H, dd), 8.12-8.09 (1H, m), 7.79 (1H, d), 7.48 (1H, dd), 7.16-7.10 (1H, m), 4.23 (1H, br s), 3.96-3.83 (4H, m), 1.37 (3H, t).

Preparation Example 6(2)

The compounds prepared according to the process described in the Preparation Example 6(1) and the physical properties thereof are shown below.

The compound represented by formula (I-11)

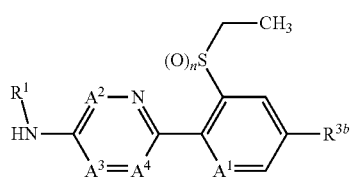
(I-11)

wherein $A^1$, $A^2$, $A^3$, $A^4$, $R^1$, $R^{3b}$, and n represent any one combination indicated in Table 21.

TABLE 21

| Present compound | $R^1$ | $A^1$ | $A^2$ | $A^3$ | $A^4$ | $R^{3b}$ | n |
|---|---|---|---|---|---|---|---|
| 14 | $CH_2CF_3$ | N | CH | CH | CH | H | 2 |
| 16 | $CH_2CF_2CF_2CF_3$ | N | CH | CH | CH | H | 2 |
| 17 | $CH_2CF_2CF_3$ | N | N | CH | CH | H | 2 |

Present compound 14: $^1$H-NMR (CDCl$_3$) δ: 8.86-8.82 (1H, m), 8.50-8.45 (1H, m), 8.08 (1H, s), 7.78 (1H, d), 7.51-7.46 (1H, m), 7.14-7.08 (1H, m), 4.42 (1H, t), 3.98-3.89 (2H, m), 3.87-3.75 (2H, m), 1.41-1.33 (3H, m).

Present compound 16: $^1$H-NMR (CDCl$_3$) δ: 8.84 (1H, dd), 8.47 (1H, dd), 8.10 (1H, d), 7.79 (1H, d), 7.48 (1H, dd), 7.12 (1H, dd), 4.29 (1H, t), 3.99-3.87 (4H, m), 1.37 (3H, t).

Present compound 17: $^1$H-NMR (CDCl$_3$) δ: 8.89 (1H, dd), 8.51 (1H, dd), 7.75 (1H, d), 7.57 (1H, dd), 6.91 (1H, d), 4.95 (1H, s), 4.40 (2H, td), 3.90 (2H, q), 1.39 (3H, t).

Preparation Example 7(1)

To a mixture of the Present compound 12 (230 mg), 60% sodium hydride (oily) (28 mg), and DMF (2 mL) was added iodomethane (89 mg). The reaction mixture was stirred at room temperature for 6 hours. To the resulting reaction mixture was added water, and the mixture was extracted with ethyl acetate. The resulting organic layers were sequentially washed with water and saturated brine, then dried over anhydrous sodium sulfate, and concentrated under reduced pressure. The resulting residues were subjected to silica gel chromatography to give the Present compound 13 represented by the following formula (44 mg).

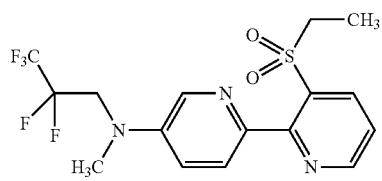

Present compound 13: $^1$H-NMR (CDCl$_3$) δ: 8.84 (1H, dd), 8.47 (1H, dd), 8.20 (1H, d), 7.83 (1H, d), 7.47 (1H, dd), 7.21 (1H, dd), 4.07-3.90 (4H, m), 3.18 (3H, s), 1.37 (3H, t).

Preparation Example 7(2)

The compound prepared according to the process described in the Preparation Example 7(1) and the physical property thereof are shown below.

The compound represented by formula (I-12)

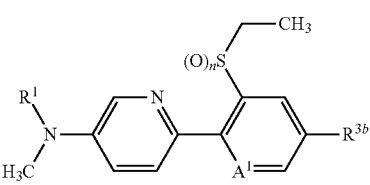
(I-12)

wherein $A^1$, $R^1$, $R^{3b}$, and n represent the combination indicated in Table 22.

TABLE 22

| Present compound | $A^1$ | $R^1$ | $R^{3b}$ | n |
|---|---|---|---|---|
| 15 | N | $CH_2CF_3$ | H | 2 |

Present compound 15: $^1$H-NMR (CDCl$_3$) δ: 8.84 (1H, dd), 8.48 (1H, dd), 8.21 (1H, d), 7.83 (1H, d), 7.47 (1H, dd), 7.23 (1H, dd), 4.01-3.92 (4H, m), 3.18 (3H, s), 1.38 (3H, t).

Preparation Example 8

The Present compound 18 represented by the following formula was prepared by using the Intermediate compound 13 instead of the Intermediate compound 4 according to the process described in the Preparation Example 6(1).

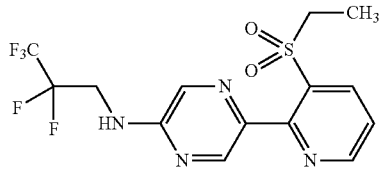

Present compound 18: $^1$H-NMR (CDCl$_3$) δ: 8.87 (1H, dd), 8.68 (1H, d), 8.48 (1H, dd), 7.98 (1H, d), 7.52 (1H, dd), 4.97 (1H, t), 4.29 (2H, td), 3.87 (2H, q), 1.37 (3H, t).

Preparation Example 9(1)

To a mixture of the Intermediate compound 18 (200 mg), 1-ethyl-3-(3-dimethylaminopropyl)carbodiimide hydrochloride (160 mg), 1-hydroxybenzotriazole (9 mg), and pyridine (3.4 mL) was added 2,2,2-trifluoroethylamine (81 mg). The reaction mixture was stirred at room temperature for 3 days. To the resulting reaction mixture was added a saturated aqueous solution of sodium hydrogen carbonate, and the mixture was extracted with ethyl acetate. The resulting organic layers were dried over anhydrous sodium sulfate, and concentrated under reduced pressure. The resulting residues were subjected to silica gel chromatography to give the Present compound 24 represented by the following formula (170 mg).

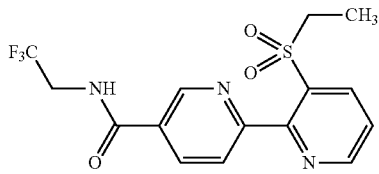 [SMILES: CCS(=O)(=O)c1cccnc1-c1ccc(C(=O)NCC(F)(F)F)cn1]

Present compound 24: $^1$H-NMR (CDCl$_3$) δ: 9.04 (1H, d), 8.91 (1H, dd), 8.51 (1H, dd), 8.25 (1H, dd), 7.94 (1H, d), 7.61 (1H, dd), 6.60-6.53 (1H, br m), 4.22-4.11 (2H, m), 3.90 (2H, q), 1.39 (3H, t).

Preparation Example 9(2)

The compounds prepared according to the process described in the Preparation Example 9(1) and the physical properties thereof are shown below.

The compound represented by formula (I-13)

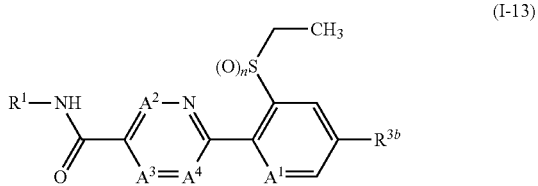

(I-13)

wherein $A^1$, $A^2$, $A^3$, $A^4$, $R^1$, $R^{3b}$, and n represent any one combination indicated in Table 23.

TABLE 23

| Present compound | $R^1$ | $A^1$ | $A^2$ | $A^3$ | $A^4$ | $R^{3b}$ | n |
|---|---|---|---|---|---|---|---|
| 25 | CH$_2$CF$_2$CF$_3$ | N | CH | CH | CH | H | 2 |
| 26 | CH$_2$CF$_3$ | N | N | CH | CH | H | 2 |
| 28 | CH$_2$CF$_2$CF$_3$ | N | N | CH | CH | H | 2 |

Present compound 25: $^1$H-NMR (CDCl$_3$) δ: 9.03 (1H, d), 8.91 (1H, dd), 8.51 (1H, dd), 8.24 (1H, dd), 7.94 (1H, d), 7.61 (1H, dd), 6.61 (1H, br s), 4.26-4.16 (2H, m), 3.90 (2H, q), 1.39 (3H, t).

Present compound 26: $^1$H-NMR (CDCl$_3$) δ: 8.98 (1H, dd), 8.57 (1H, dd), 8.50 (1H, d), 8.47 (1H, t), 8.17 (1H, d), 7.70 (1H, dd), 4.27-4.17 (2H, m), 3.91 (2H, q), 1.44 (3H, t).

Present compound 28: $^1$H-NMR (CDCl$_3$) δ: 8.97 (1H, dd), 8.56 (1H, dd), 8.50 (1H, d), 8.46 (1H, t), 8.17 (1H, d), 7.69 (1H, dd), 4.33-4.21 (2H, m), 3.91 (2H, q), 1.43 (3H, t).

Preparation Example 10

To a mixture of the Present compound 26 (100 mg), potassium carbonate (56 mg), and acetone (1.5 mL) was added iodomethane (25 μL). The reaction mixture was heated with stirring at 50° C. for 9 hours. To the resulting mixture was added water, and the mixture was extracted with ethyl acetate. The resulting organic layers were dried over anhydrous sodium sulfate, and concentrated under reduced pressure. The resulting residues were subjected to silica gel chromatography to give the Present compound 27 represented by the following formula (58 mg).

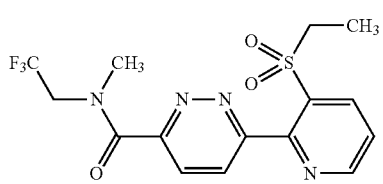 [SMILES: CCS(=O)(=O)c1cccnc1-c1ccc(C(=O)N(C)CC(F)(F)F)nn1]

Present compound 27: $^1$H-NMR (CDCl$_3$) δ: 8.96 (1H, dd), 8.55 (1H, dd), 8.16-8.01 (2H, m), 7.68 (1H, dd), 4.64-4.26 (2H, m), 3.94-3.83 (2H, m), 3.38-3.33 (3H, m), 1.44-1.37 (3H, m).

Preparation Example 11(1)

To a mixture of the Intermediate compound 21 (340 mg), 60% sodium hydride (oily) (66 mg), and NMP (3 mL) was added 1,2-dibromo-1,1,2,2-tetrafluoroethane (500 μL). The reaction mixture was stirred at room temperature for 12 hours. To the resulting reaction mixture was added water, and the mixture was extracted with ethyl acetate. The resulting organic layers were dried over anhydrous sodium sulfate, and concentrated under reduced pressure. The resulting residues were subjected to silica gel chromatography to give the Present compound 21 represented by the following formula (30 mg).

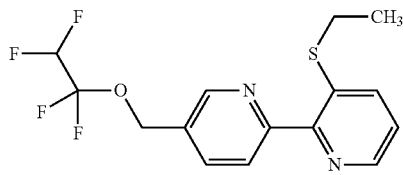 [SMILES: CCSc1cccnc1-c1ccc(COC(F)(F)C(F)F)cn1]

Present compound 21: $^1$H-NMR (CDCl$_3$) δ: 8.73 (1H, d), 8.46 (1H, dd), 8.05 (1H, d), 7.84 (1H, dd), 7.73 (1H, dd), 7.28 (1H, dd), 5.78 (1H, tt), 5.11 (2H, s), 2.91 (2H, q), 1.32 (3H, t).

Preparation Example 11(2)

The compounds prepared according to the process described in the Preparation Example 11(1) and the physical properties thereof are shown below.

The compound represented by formula (I-14)

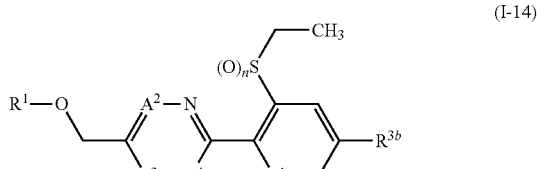

(I-14)

wherein $A^1$, $A^2$, $A^3$, $A^4$, $R^1$, $R^{3b}$, and n represent any one combination indicated in Table 24.

TABLE 24

| Present compound | R¹ | A¹ | A² | A³ | A⁴ | R³ᵇ | n |
|---|---|---|---|---|---|---|---|
| 19 | CH₂CF₃ | N | CH | CH | CH | H | 0 |
| 22 | CH₂CF₂CF₂H | N | CH | CH | CH | H | 0 |

Present compound 19: ¹H-NMR (CDCl₃) δ: 8.69 (1H, d), 8.46 (1H, dd), 8.02 (1H, d), 7.85 (1H, dd), 7.72 (1H, dd), 7.28 (1H, dd), 4.78 (2H, s), 3.90 (2H, q), 2.91 (2H, q), 1.32 (3H, t).

Present compound 22: ¹H-NMR (CDCl₃) δ: 8.68 (1H, d), 8.46 (1H, dd), 8.02 (1H, d), 7.81 (1H, dd), 7.72 (1H, dd), 7.28 (1H, dd), 5.96 (1H, tt), 4.73 (2H, s), 3.90 (2H, tt), 2.91 (2H, q), 1.32 (3H, t).

Preparation Example 12

The Present compound 20 represented by the following formula was prepared by using the Present compound 19 instead of the Intermediate compound 9 according to the process described in the Reference Preparation Example 7.

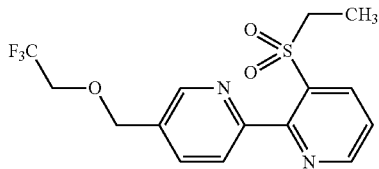 [SMILES: CCS(=O)(=O)c1cccnc1-c1ccc(COCC(F)(F)F)cn1]

Present compound 20: ¹H-NMR (CDCl₃) δ: 8.89 (1H, dd), 8.60 (1H, s), 8.50 (1H, dd), 7.94-7.79 (2H, m), 7.57 (1H, dd), 4.80 (2H, s), 3.98-3.85 (4H, m), 1.38 (3H, t).

Preparation Example 13

The Present compound 23 represented by the following formula was prepared by using the Present compound 22 instead of the Intermediate compound 9 according to the process described in the Reference Preparation Example 7.

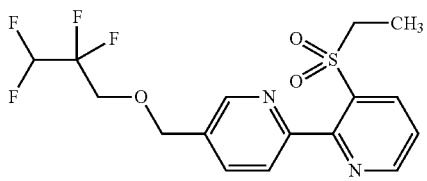 [SMILES: CCS(=O)(=O)c1cccnc1-c1ccc(COCC(F)(F)C(F)F)cn1]

Present compound 23: ¹H-NMR (CDCl₃) δ: 8.89 (1H, dd), 8.58 (1H, s), 8.50 (1H, dd), 7.85 (2H, s), 7.57 (1H, dd), 5.97 (1H, tt), 4.75 (2H, s), 3.96-3.87 (4H, m), 1.38 (3H, t).

Preparation Example 14(1)

To a mixture of the Intermediate compound 22 (100 mg), diisopropylethylamine (94 μL), and chloroform (1 mL) was added trifluoroacetic anhydride (110 μL) under ice-cooling. The reaction mixture was stirred at room temperature for 5 hours, water was added thereto, and the mixture was extracted with chloroform. The resulting organic layers were dried over anhydrous sodium sulfate, and concentrated under reduced pressure. The resulting residues were subjected to silica gel chromatography to give the Present compound 29 represented by the following formula (160 mg).

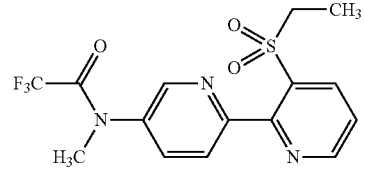 [SMILES: CCS(=O)(=O)c1cccnc1-c1ccc(N(C)C(=O)C(F)(F)F)cn1]

Present compound 29: ¹H-NMR (CDCl₃) δ: 8.91 (1H, dd), 8.56 (1H, s), 8.51 (1H, dd), 7.96 (1H, d), 7.80 (1H, d), 7.61 (1H, dd), 3.86 (2H, q), 3.45 (3H, s), 1.38 (3H, t).

Preparation Example 14(2)

The compounds prepared according to the process described in the Preparation Example 14(1) and the physical properties thereof are shown below.

The compound represented by formula (I-15)

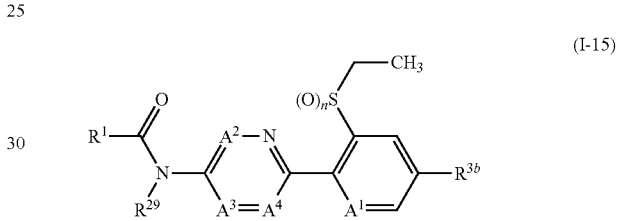

wherein A¹, A², A³, A⁴, R¹, R³ᵇ, R²⁹, and n represent any one combination indicated in Table 25.

TABLE 25

| Present compound | R¹ | R²⁹ | A¹ | A² | A³ | A⁴ | R³ᵇ | n |
|---|---|---|---|---|---|---|---|---|
| 30 | CF₂CF₃ | CH₃ | N | CH | CH | CH | H | 2 |
| 31 | CF₂CF₃ | H | N | N | CH | CH | H | 2 |

Present compound 30: ¹H-NMR (CDCl₃) δ: 8.91 (1H, dd), 8.56 (1H, s), 8.52 (1H, dd), 7.96 (1H, d), 7.80 (1H, dd), 7.61 (1H, dd), 3.86 (2H, q), 3.45 (3H, s), 1.38 (3H, t).

Present compound 31: ¹H-NMR (CDCl₃) δ: 8.95 (1H, dd), 8.63 (1H, d), 8.55 (1H, dd), 8.13 (1H, d), 7.67 (1H, dd), 3.86 (2H, q), 1.42 (3H, t).

Next, the Formulation Examples of the Present compound are shown below. The "part(s)" represents "part(s) by weight" unless otherwise specified.

Formulation Example 1

Any one of the Present compounds 1 to 31 (10 parts) is mixed with a mixture of xylene (35 parts) and DMF (35 parts), and then polyoxyethylene styryl phenyl ether (14 parts) and calcium dodecylbenzene sulfonate (6 parts) are added thereto, followed by mixing them to obtain each formulation.

Formulation Example 2

Sodium lauryl sulfate (4 parts), calcium lignin sulfonate (2 parts), synthetic hydrated silicon oxide fine powder (20 parts), and diatomaceous earth (54 parts) are mixed, and further any one of the Present compounds 1 to 31 (20 parts) is added thereto, followed by mixing them to obtain each wettable powder.

Formulation Example 3

To any one of the Present compounds 1 to 31 (2 parts) are added synthetic hydrated silicon oxide fine powder (1 part), calcium lignin sulfonate (2 parts), bentonite (30 parts), and kaolin clay (65 parts), followed by mixing them to obtain a mixture. To the mixture is then added an appropriate amount of water, the resulting mixture is additionally stirred, and subjected to granulation with a granulator and forced-air drying to obtain each granule.

Formulation Example 4

Any one of the Present compounds 1 to 31 (1 part) is mixed with an appropriate amount of acetone, and then synthetic hydrated silicon oxide fine powder (5 parts), acidic isopropyl phosphate (0.3 part), and kaolin clay (93.7 parts) are added thereto, followed by mixing with stirring thoroughly and removal of acetone from the mixture by evaporation to obtain each dust formulation.

Formulation Example 5

A mixture of polyoxyethylene alkyl ether sulfate ammonium salt and white carbon (weight ratio of 1:1) (35 parts), any one of the Present compounds 1 to 31 (10 parts), and water (55 parts) are mixed, followed by finely grounding by a wet grinding method to obtain each flowable.

Formulation Example 6

Any one of the Present compounds 1 to 31 (0.1 part) is mixed with a mixture of xylene (5 parts) and trichloroethane (5 parts), and the resulting mixture is then mixed with kerosene (89.9 parts) to obtain each oil solution.

Formulation Example 7

Any one of the Present compounds 1 to 31 (10 mg) is mixed with acetone (0.5 mL), and the solution is added dropwise to a solid feed powder for an animal (solid feed powder for rearing and breeding CE-2, manufactured by CLEA Japan, Inc.) (5 g), followed by mixing the resulting mixture uniformly, and then by drying it by evaporation of acetone to obtain each poison bait.

Formulation Example 8

Any one of the Present compounds 1 to 31 (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, followed by shaking and further mounting an actuator to obtain each oily aerosol.

Formulation Example 9

A mixture of any one of the Present compounds 1 to 31 (0.6 part), BHT (2,6-di-tert-butyl-4-methylphenol) (0.01 part), xylene (5 parts), kerosene (3.39 parts) and an emulsifier {Rheodol MO-60 (manufactured by Kao Corporation)} (1 part), and distilled water (50 parts) are filled into an aerosol container, and a valve part is attached. Then, a propellant (LPG) (40 parts) is filled therein through the valve under pressure to obtain each aqueous aerosol.

Formulation Example 10

Any one of the Present compounds 1 to 31 (0.1 g) is mixed with propylene glycol (2 mL), and the resulting solution is impregnated into a ceramic plate having a size of 4.0 cm×4.0 cm and a thickness of 1.2 cm to obtain each thermal fumigant.

Formulation Example 11

Any one of the Present compounds 1 to 31 (5 parts) and ethylene-methyl methacrylate copolymer (the ratio of the methyl methacrylate in the copolymer: 10% by weight, Acryft (registered trademark) WD 301, manufactured by Sumitomo Chemical Co. Ltd.) (95 parts) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 12

Any one of the Present compounds 1 to 31 (5 parts) and flexible vinyl chloride resin (95 parts) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 13

Any one of the Present compounds 1 to 31 (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 14

Any one of the Present compounds 1 to 31 (25 mg), lactose (60 mg), corn starch (25 mg), carmellose calcium (6 mg), and an appropriate amount of a 5% hydroxypropyl methylcellulose are mixed, and the resulting mixture is filled into a hard shell gelatin capsule or a hydroxypropyl methylcellulose capsule to obtain each capsule.

Formulation Example 15

To any one of the Present compounds 1 to 31 (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum K (manufactured by Vanderbilt Co.) (100 mg), perfume (35 mg), and a colorant (500 mg) is added distilled water so that the final volume is set to be 100 mL, followed by mixing them to obtain each suspension for oral administration.

Formulation Example 16

Any one of the Present compounds 1 to 31 (5% by weight) is mixed with an emulsifier (5% by weight), benzyl alcohol (3% by weight), and propylene glycol (30% by weight), and phosphate buffer is added thereto so that the pH of the solution is set to be 6.0 to 6.5, and then water is added thereto as the rest parts to obtain each solution for oral administration.

Formulation Example 17

To fractional distillated palm oil (57% by weight) and polysorbate 85 (3% by weight) is added aluminum distearate (5% by weight), and the mixture is dispersed by heating. The resulting mixture is cooled to room temperature, and saccharin (25% by weight) is dispersed in the oil vehicle. Any one of the Present compounds 1 to 31 (10% by weight) is divided thereto to obtain each paste-like formulation for oral administration.

Formulation Example 18

Any one of the Present compounds 1 to 31 (5% by weight) is mixed with a limestone filler (95% by weight), followed by a wet granulation of the resulting mixture to obtain each granule for oral administration.

Formulation Example 19

Any one of the Present compounds 1 to 31 (5 parts) is mixed with diethylene glycol monoethyl ether (80 parts), propylene carbonate (15 parts) is added thereto, and the resulting mixture is mixed to obtain each spot-on solution.

Formulation Example 20

Any one of the Present compounds 1 to 31 (10 parts) is mixed with diethylene glycol monoethyl ether (70 parts), 2-octyldodecanol (20 parts) is added thereto, and the resulting mixture is mixed to obtain each pour-on solution.

Formulation Example 21

To any one of the Present compounds 1 to 31 (0.5 part) are added Nikkol (registered trademark) TEALS-42 (manufactured by Nikko Chemicals Co., Ltd.: a 42% aqueous solution of triethanolamine lauryl sulfate) (60 parts) and propylene glycol (20 parts), the resulting mixture is mixed with stirring thoroughly to obtain a homogeneous solution, water (19.5 parts) is then added thereto, and the resulting mixture is further mixed with stirring thoroughly to obtain each homogeneous solution of shampoo formulation.

Formulation Example 22

Any one of the Present compounds 1 to 31 (0.15% by weight), animal feed (95% by weight), and a mixture (4.85% by weight) consisting of dibasic calcium phosphate, diatomaceous earth, Aerosil, and carbonate (or chalk) are mixed with stirring thoroughly to obtain each premix for animal feed.

Formulation Example 23

Any one of the Present compounds 1 to 31 (7.2 g) and Hosco (registered trademark) S-55 (manufactured by Maruishi Pharmaceuticals) (92.8 g) are mixed at 100° C., and the resulting mixture is poured into a suppository mold, followed by performing a cooling solidification to obtain each suppository.

Next, Test Examples are used to show efficacies of the Present compounds on controlling harmful arthropods. In the following Test Examples, the tests were carried out at 25° C. with preventing insects from escape.

Test Example 1

Each test compound is formulated according to the process described in the Formulation Example 5 to obtain each formulation, and water containing a spreader (0.03% by volume) is added thereto to prepare a diluted solution containing a prescribed concentration of each test compound.

Cucumber (*Cucumis sativus*) seedlings (on the developmental stage of the second true leaf) are planted in a container and approximately 30 cotton aphids (*Aphis gossypii*) (all stages of life) are released onto the cucumber seedlings. After 1 day, each of said diluted solutions is sprayed into the seedlings in a ratio of 10 mL/seedling. After additional 5 days, the number of the surviving insects is examined and the controlling value is calculated by the following equation.

Controlling value (%)=$\{1-(Cb \times Tai)/(Cai \times Tb)\} \times 100$ wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where a similar treatment procedure to that of the treated group except not using each test compound is done.

When the prescribed concentration was 500 ppm and each of the following Present compounds was used as a test compound to carry out a test according to the Test Example 1, each of the following Present compounds showed 90% or greater as the controlling value.

Present compounds: 1, 3, 5, 7, 8, 12, 14, 16, 17, 18, 23, 24, 25, 28, 29, 30, and 31

When the prescribed concentration was 200 ppm and each of the following Present compounds was used as a test compound to carry out a test according to the Test Example 1, each of the following Present compounds showed 90% or greater as the controlling value.

Present compounds: 5, 6, 7, 8, 9, 10, 12, 13, 15, 16, 17, 18, 20, 23, 24, 25, 26, and 28

Test Example 2

Each test compound is formulated according to the process described in the Formulation Example 5 to obtain each formulation, and water is added thereto to prepare a diluted solution containing a prescribed concentration of each test compound.

Cucumber seedlings (on the developmental stage of the second true leaf) are planted in a container, and each of said diluted solutions is irrigated into the plant foot in a ratio of 5 mL/seedling. After 7 days, approximately 30 cotton aphids (*Aphis gossypii*) (all stages of life) are released onto the surfaces of leaves of the cucumber seedlings. After additional 6 days, the number of the surviving insects is examined and the controlling value is calculated by the following equation.

Controlling value (%)={1−(Cb×Tai)/(Cai×Tb)}×100 wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where a similar treatment procedure to that of the treated group except not using each test compound is done.

When the prescribed concentration was 200 ppm and each of the following Present compounds was used as a test compound to carry out a test according to the Test Example 2, each of the following Present compounds showed 90% or greater as the controlling value.

Present compounds: 5, 6, 7, 8, 12, 13, 17, and 18

Test Example 3

Each test compound is formulated according to the process described in the Formulation Example 5 to obtain each formulation, and water containing a spreader (0.03% by volume) is added thereto to prepare a diluted solution containing a prescribed concentration of each test compound.

Rice (*Oryza sativa*) seedlings (on the developmental stage of the second true leaf) are planted in a container, and each of said diluted solutions is sprayed into the seedlings in a ratio of 10 mL/seedling. Thereafter, 20 the 3rd instar larvae of brown planthopper (*Nilaparvata lugens*) are released onto the rice seedlings. After 6 days, the number of the surviving insects is examined and the mortality of insects is calculated by the following equation.

Mortality (%)={1−Number of surviving insects/20}×100

When the prescribed concentration was 500 ppm and each of the following Present compounds was used as a test compound to carry out a test according to the Test Example 3, each of the following Present compounds showed 90% or greater as the mortality.
Present Compounds: 5, 7, and 8

When the prescribed concentration was 200 ppm and each of the following Present compounds was used as a test compound to carry out a test according to the Test Example 3, each of the following Present compounds showed 90% or greater as the mortality.
Present Compounds: 5, 6, 7, 8, 9, and 10

Test Example 4

Each test compound is formulated according to the process described in the Formulation Example 5 to obtain each formulation, and water is added thereto to prepare a diluted solution containing a prescribed concentration of each test compound.

Each of said diluted solutions (5 mL) is added to a container, and therein are installed Rice seedlings (on the developmental stage of the second true leaf) planted in a container having a hole in the bottom. After 7 days, 20 the 3rd instar larvae of brown planthopper (*Nilaparvata lugens*) are released onto the rice seedlings. After additional 6 days, the number of the surviving insects is examined and the mortality of insects is calculated by the following equation.

Mortality (%)={1−Number of surviving insects/20}×100

When the prescribed concentration was 200 ppm and each of the following Present compounds was used as a test compound to carry out a test according to the Test Example 4, each of the following Present compounds showed 90% or greater as the mortality.
Present Compounds: 6, 7, 9, and 10

Test Example 5

Each test compound is formulated according to the process described in the Formulation Example 5 to obtain each formulation, and water is added thereto to prepare a diluted solution containing a prescribed concentration of each test compound.

An artificial diet (Insecta LF, manufactured by Nosan Corporation) (7.7 g) is placed in a container, and thereto is irrigated each of said diluted solutions (2 mL). Five(5) the 4th instar larvae of tobacco cutworm (*Spodoptera litura*) are released onto the artificial diet. After 5 days, the number of the surviving insects is counted, and the mortality of insects is calculated by the following equation.

Mortality (%)=(1−Number of surviving insects/5)×100

The results of the test that was carried out according to the Test Example 5 are shown below.

When the prescribed concentration was 500 ppm and each of the following Present compounds was used as a test compound to carry out a test according to the Test Example 5, each of the following Present compounds showed 80% or greater as the mortality.
Present Compounds: 7, 8, and 18

Test Example 6

Each test compound is formulated according to the process described in the Formulation Example 5 to obtain each formulation, and water containing a spreader (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedling. Thereafter, the stem and leaf of the seedlings are cut out, and placed into a container lined with a filter paper. Five(5) the 2nd instar larvae of cabbage moth (*Plutella xylostella*) are released into the container. After 5 days, the number of the surviving insects is counted, and the mortality of insects is calculated by the following equation.

Mortality (%)=(1−Number of surviving insects/5)×100

When the prescribed concentration was 500 ppm and each of the following Present compounds was used as a test compound to carry out a test according to the Test Example 6, each of the following Present compounds showed 80% or greater as the mortality.
Present Compounds: 5, 7, 8, 12, 14, 16, 18, 23, 28, and 31

Test Example 7

Each test compound is formulated according to the process described in the Formulation Example 5 to obtain each formulation, and water containing a spreader (0.03% by volume) is added thereto to prepare a diluted solution containing a prescribed concentration of each test compound.

Cabbage seedlings (on the developmental stage of the third to fourth true leaf) are planted in a container, and each of said diluted solutions is sprayed into the seedlings in a ratio of 20 mL/seedling. Thereafter, 10 the 3rd instar larvae of cabbage moth (*Plutella xylostella*) are released into the cabbage seedlings. After 5 days, the number of the surviving insects is counted, and the mortality of insects is calculated by the following equation.

Mortality (%)=(1−Number of surviving insects/10)×100

When the prescribed concentration was 200 ppm and each of the following Present compounds was used as a test compound to carry out a test according to the Test Example 7, each of the following Present compounds showed 90% or greater as the mortality.
Present Compounds: 5, 6, 7, 8, 9, 10, 18, and 28

Test Example 8

Each test compound is dissolved into a mixed solution (50 μL) of polyoxyethylene sorbitan mono-cocoate:acetone (at a volume ratio of polyoxyethylene sorbitan mono-cocoate: acetone=5:95) per 1 mg of the test compound, and water containing a spreader (0.03% by volume) is added thereto to prepare a diluted solution containing a prescribed concentration of each test compound.

Corns (*Zea mays*) are inoculated onto a tray lined with wet Kimwipes. After the corns are grown for 5 days, the entire seedlings of the corns are immersed into each of said diluted solutions for 30 seconds. Thereafter, two seedlings are placed into a petri dish (diameter: 90 mm), and 10 the 2nd instar larvae of western corn rootworm (*Diabrotica virgifera virgifera*) are released into the dish. After 5 days, the number of the dead insects is counted, and the mortality of insects is calculated by the following equation.

Mortality (%)=(Number of dead insects/10)×100

When the prescribed concentration was 500 ppm and each of the following Present compounds was used as a test compound to carry out a test according to the Test Example 8, each of the following Present compounds showed 80% or greater as the mortality.
Present Compounds: 5, 6, 7, 8, 12, 14, 17, and 21

Test Example 9

Each test compound is dissolved into a mixed solution (10 μL) of xylene, DMF, and a surfactant (at a volume ratio of xylene:DMF:surfactant=4:4:1) per 1 mg of the test compound, and water containing a spreader (0.03% by volume) is added thereto to prepare a diluted solution containing a prescribed concentration of each test compound.

Cucumber seedlings (on the developmental stage of the second to third true leaf) are planted in a container, and each of said diluted solutions is sprayed into the seedlings in a ratio of 10 mL/seedling. Thereafter, the second leaves are cut out and placed into a container, and 10 the 2nd instar larvae of cucurbit leaf beetle (*Aulacophora femoralis*) are released into the container. After 5 days, the number of the dead insects is counted, and the mortality of insects is calculated by the following equation.

Mortality (%)=(Number of dead insects/10)×100

When the prescribed concentration was 50 ppm and each of the following Present compounds was used as a test compound to carry out a test according to the Test Example 9, each of the following Present compounds showed 80% or greater as the mortality.
Present Compounds: 9 and 10

Test Example 10

Each test compound is formulated according to the process described in the Formulation Example 5 to obtain each formulation, and water is added thereto to prepare a diluted solution containing a prescribed concentration of each test compound.

A filter paper having a diameter of 5.5 cm is lined with a container, sucrose (30 mg) is placed on the filter paper, and then each of said diluted solutions (0.7 mL) is added dropwise thereto. Ten(10) female adult houseflies (*Musca domestica*) are released into said container. After 24 hours, the number of the dead insects is counted, and the mortality of insects is calculated by the following equation.

Mortality (%)=(Number of dead insects/Number of test insects)×100

When the prescribed concentration was 500 ppm and each of the following Present compounds was used as a test compound to carry out a test according to the Test Example 10, each of the following Present compounds showed 100% as the mortality.
Present Compounds: 1, 3, 17, 24, and 28

INDUSTRIAL APPLICABILITY

The Present compounds have excellent control efficacies against harmful arthropods.

The invention claimed is:
1. A compound represented by formula (I):

(I)

[chemical structure]

or an N-oxide compound thereof, wherein:
$A^1$ represents a nitrogen atom;

[chemical structure]

hereinafter referred to as "Het", represents Het-1:

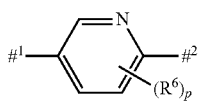

wherein #¹ represents the binding position of Het and T, and #² represents the binding position of Het and

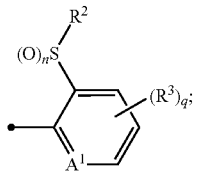

T represents T-1, T-2, T-3, T-4, T-5, T-6, or T-7:

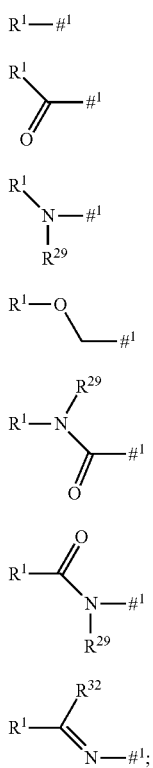

R¹ represents a C1-C10 chain hydrocarbon group having one or more halogen atoms, a (C1-C5 alkoxy) C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

R² represents an ethyl group;
q represents 0, 1, 2, or 3;
R³ represents a C1-C6 chain hydrocarbon group optionally having one or more substituents selected from Group B; a phenyl group optionally having one or more substituents selected from Group D; a 5 or 6 membered aromatic heterocyclic group optionally having one or more substituents selected from Group D; a $OR^{12}$; a $NR^{11}R^{12}$; a $NR^{11a}R^{12a}$; a $NR^{24}NR^{11}R^{12}$; a $NR^{24}OR^{11}$; a $NR^{11}C(O)R^{13}$; a $NR^{24}NR^{11}C(O)R^{13}$; a $NR^{11}C(O)OR^{14}$; a $NR^{24}NR^{11}C(O)OR^{14}$; a $NR^{11}C(O)NR^{15}R^{16}$; a $NR^{24}NR^{11}C(O)NR^{15}R^{16}$; a $N=CHNR^{15}R^{16}$; a $N=S(O)_xR^{15}R^{16}$; a $S(O)_yR^{15}$; a $C(O)OR^{17}$; a $C(O)NR^{11}R^{12}$; a cyano group; a nitro group; or a halogen atom, wherein when q represents 2 or 3, two or three R³ may be identical to or different from each other;
p represents 0 or 1;
R⁶ represents a halogen atom;
$R^{11}$, $R^{17}$, $R^{24}$, and $R^{29}$ represent each independently a hydrogen atom or a C1-C6 chain hydrocarbon group optionally having one or more halogen atoms;
$R^{32}$ represents a hydrogen atom, a halogen atom, a $OR^{33}$, a $NR^{34}R^{35}$, or a C1-C6 chain hydrocarbon group optionally having one or more halogen atoms;
$R^{33}$ represents a C1-C6 chain hydrocarbon group optionally having one or more halogen atoms;
$R^{34}$ and $R^{35}$ represent each independently a hydrogen atom or a C1-C6 chain hydrocarbon group optionally having one or more halogen atoms;
$R^{12}$ represents a hydrogen atom, a C1-C6 chain hydrocarbon group optionally having one or more halogen atoms, a C1-C6 alkyl group having one substituent selected from Group F, or a $S(O)_2R^{23}$;
$R^{23}$ represents a C1-C6 chain hydrocarbon group optionally having one or more halogen atoms or a phenyl group optionally having one or more substituents selected from Group D;
$R^{11a}$ and $R^{12a}$ are combined with the nitrogen atom to which they are attached to represent a 3-7 membered nonaromatic heterocyclic group optionally having one or more substituents selected from Group E wherein said 3-7 membered nonaromatic heterocyclic group represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, or a 1,4-thiazepane ring;
$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl) C1-C3 alkyl group optionally having one or more halogen atoms, a phenyl group optionally having one or more substituents selected from Group D, or a 5 or 6 membered aromatic heterocyclic group optionally having one or more substituents selected from Group D;
$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group wherein the phenyl moiety in the phenyl C1-C3 alkyl group may optionally have one or more substituents selected from Group D;

$R^{15}$ and $R^{16}$ represent each independently a C1-C6 alkyl group optionally having one or more halogen atoms;

n represents 2;

y represents 0, 1, or 2; and x represents 0 or 1;

Group B represents a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C represents a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D represents a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$ group, a $OC(O)R^{21}$ group, a $C(O)OR^{21}$ group, a cyano group, a nitro group, and a halogen atom wherein $R^{21}$ and $R^{22}$ represent each independently a C1-C6 alkyl group optionally having one or more halogen atoms;

Group E represents a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F represents a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3-7 membered non-aromatic heterocyclic group optionally having one or more substituents selected from Group C; and Group G represents a group consisting of a halogen atom and a C1-C6 haloalkyl group.

2. The compound according to claim 1, wherein
T represents T-1, T-3, or T-4; and
$R^1$ represents a C1-C10 chain hydrocarbon group having one or more halogen atoms or a (C1-C5 alkoxy)C2-C5 alkyl group having one or more halogen atoms.

3. The compound according to claim 1, wherein $R^3$ represents a C1-C6 chain hydrocarbon group optionally having one or more halogen atoms, or a halogen atom.

4. The compound according to claim 1, wherein
T represents T-1, T-3, or T-4;
$R^3$ represents a C1-C6 chain hydrocarbon group optionally having one or more substituents selected from Group B; a phenyl group optionally having one or more substituents selected from Group G; a 5 membered aromatic heterocyclic group having 1 to 4 nitrogen atoms optionally having one or more substituents selected from the group consisting of a C1-C6 alkyl group having one or more halogen atoms, and a halogen atom; a 6 membered aromatic heterocyclic group having 1 to 2 nitrogen atoms; a $NR^{11}R^{12}$; a $NR^{11a}R^{12a}$; a $NR^{24}NR^{11}R^{12}$; or a halogen atom; wherein said 6 membered aromatic heterocyclic group may optionally have one or more substituents selected from the group consisting of a C1-C6 alkyl group having one or more halogen atoms, and a halogen atom; and
q represents 0, 1, or 2, wherein when q represents 2, two $R^3$ may be identical to or different from each other.

5. The compound according to claim 1, wherein
T represents T-1;
$R^3$ represents a C1-C6 chain hydrocarbon group optionally having one or more halogen atoms, or a halogen atom; and
q represents 0 or 1.

6. The compound according to claim 1, wherein
T represents T-3;
$R^3$ represents a C1-C6 chain hydrocarbon group optionally having one or more halogen atoms, or a halogen atom; and
q represents 0 or 1.

7. The compound according to claim 1, wherein
T represents T-4;
$R^3$ represents a C1-C6 chain hydrocarbon group optionally having one or more halogen atoms, or a halogen atom; and
q represents 0 or 1.

8. A composition for controlling a harmful arthropod comprising the compound according to claim 1 and an inert carrier.

9. A method for controlling a harmful arthropod which comprises applying an effective amount of the compound according to claim 1 to a harmful arthropod or a habitat where a harmful arthropod lives.

10. A composition comprising one or more ingredients selected from the group consisting of Group (a), Group (b), Group (c), Group (d), and Group (e), and the compound according to claim 1;
Group (a) represents a group consisting of an insecticidal active ingredient, an acaricidal active ingredient, and a nematicidal active ingredient;
Group (b) represents a fungicidal active ingredient;
Group (c) represents a plant growth regulatory ingredient;
Group (d) represents a phytotoxicity-reducing ingredient; and
Group (e) represents a synergist.

* * * * *